US012704506B2

(12) United States Patent
Straus

(10) Patent No.: US 12,704,506 B2
(45) **Date of Patent: *Aug. 11, 2026**

(54) MICROBIAL ANALYSIS WITHOUT CELL PURIFICATION

(71) Applicant: First Light Diagnostics, Inc., Chelmsford, MA (US)

(72) Inventor: Don Straus, Cambridge, MA (US)

(73) Assignee: First Light Diagnostics, Inc., Chelmsford, MA (US)

( * ) Notice: Subject to any disclaimer, the term of this patent is extended or adjusted under 35 U.S.C. 154(b) by 1426 days.

This patent is subject to a terminal disclaimer.

(21) Appl. No.: 17/282,633

(22) PCT Filed: Oct. 4, 2019

(86) PCT No.: PCT/US2019/054885

§ 371 (c)(1),
(2) Date: Apr. 2, 2021

(87) PCT Pub. No.: WO2020/073016

PCT Pub. Date: Apr. 9, 2020

(65) Prior Publication Data

US 2023/0235411 A1 Jul. 27, 2023

Related U.S. Application Data

(60) Provisional application No. 62/741,253, filed on Oct. 4, 2018.

(51) Int. Cl.

| | |
|---|---|
| ***C12Q 1/689*** | (2018.01) |
| ***C12Q 1/6841*** | (2018.01) |
| ***G01N 33/543*** | (2006.01) |

(52) U.S. Cl.

CPC ..... *G01N 33/54333* (2013.01); *C12Q 1/6841* (2013.01); *C12Q 1/689* (2013.01)

(58) Field of Classification Search

CPC .......... G01N 33/54333; G01N 35/0098; B01L 3/502715; B01L 3/502761; C12Q 1/18; C12Q 1/6841; C12Q 1/689

See application file for complete search history.

(56) References Cited

U.S. PATENT DOCUMENTS

| | | | |
|---|---|---|---|
| 2,672,431 | A | 3/1954 | Goetz |
| 2,761,813 | A | 9/1956 | Goetz |
| 3,694,317 | A | 9/1972 | Scher |
| 3,981,776 | A | 9/1976 | Saxholm |
| 4,097,586 | A | 6/1978 | Gross |
| 4,098,876 | A | 7/1978 | Piasio et al. |
| 4,115,535 | A | 9/1978 | Giaever |
| 4,125,375 | A | 11/1978 | Hunter |
| 4,129,419 | A | 12/1978 | Hermann, Jr. |
| 4,141,687 | A | 2/1979 | Forrest et al. |
| 4,157,323 | A | 6/1979 | Yen et al. |
| 4,177,253 | A | 12/1979 | Davies et al. |
| 4,222,744 | A | 9/1980 | McConnell |
| 4,436,826 | A | 3/1984 | Wang |
| 4,438,068 | A | 3/1984 | Forrest |
| 4,454,233 | A | 6/1984 | Wang |
| 4,455,370 | A | 6/1984 | Bartelsman et al. |
| 4,477,578 | A | 10/1984 | Miles et al. |
| 4,537,861 | A | 8/1985 | Elings et al. |
| 4,562,157 | A | 12/1985 | Lowe et al. |
| 4,565,783 | A | 1/1986 | Hansen et al. |
| 4,582,810 | A | 4/1986 | Rosenstein |
| 4,587,213 | A | 5/1986 | Malecki |
| 4,614,585 | A | 9/1986 | Mehra et al. |
| 4,693,972 | A | 9/1987 | Mansour et al. |
| 4,731,337 | A | 3/1988 | Luotola et al. |
| 4,745,077 | A | 5/1988 | Holian et al. |
| 4,750,820 | A | 6/1988 | Pareigat |
| 4,777,137 | A | 10/1988 | Lemonnier |
| 4,777,145 | A | 10/1988 | Luotola et al. |
| 4,912,037 | A | 3/1990 | Lemonnier |
| 4,922,092 | A | 5/1990 | Rushbrooke et al. |
| 4,959,301 | A | 9/1990 | Weaver et al. |
| 4,981,783 | A | 1/1991 | Augenlicht |
| 4,988,302 | A | 1/1991 | Smith et al. |
| 4,988,618 | A | 1/1991 | Li et al. |
| 5,073,497 | A | 12/1991 | Schwartz |
| 5,089,413 | A | 2/1992 | Nelson et al. |

(Continued)

FOREIGN PATENT DOCUMENTS

| | | |
|---|---|---|
| AU | 760425 B2 | 5/2003 |
| CN | 2486557 Y | 4/2002 |

(Continued)

OTHER PUBLICATIONS

Al-Hakiem, 1982, Development of Fluoroimmunoassays for the Determination of Individual or Combined Levels of Procainamide and N-Acetylprocainamide in Serum, J Immunoassay 3(1):91-110.

Allman, 1981, Fluoroimmunoassay of Progesterone in Human Serum of Plasma, Clin Chem 27:1176-1176.

Batchelor, 2012, Light and Optics, Machine Vision Handbook, Springer-Verlag, 157-258.

Catalogue of Becton, 2003, Dickinson and Company, p. 28, 29, 32-35, 150 and 151, Japan.

(Continued)

*Primary Examiner* — Sarae L Bausch

(74) *Attorney, Agent, or Firm* — Flener IP & Business Law

(57) ABSTRACT

The invention provides systems and methods for rapid automated identification of microbes and antimicrobial susceptibility testing (AST) directly from a patient specimen, without specimen preparation. Specimens are loaded into an analytical cartridge for processing. Analytical cartridges are preloaded with species-specific labels that are used to identify and enumerate microbes in the specimen. Instruments, such as analyzers can be used to interact with analytical cartridges to carry out methods of the invention all within the cartridge.

18 Claims, 57 Drawing Sheets

(56) References Cited

U.S. PATENT DOCUMENTS 5,130,733 A 7/1992 Taniguchi et al.
5,137,812 A 8/1992 Matner
5,190,666 A 3/1993 Bisconte
5,232,838 A 8/1993 Nelson et al.
5,238,810 A 8/1993 Fujiwara et al.
5,258,284 A 11/1993 Morris, Jr. et al.
5,262,526 A 11/1993 Sasamoto et al.
5,292,644 A 3/1994 Berg
5,306,420 A 4/1994 Bisconte
5,321,545 A 6/1994 Bisconte
5,348,885 A 9/1994 Labarthe
5,355,215 A 10/1994 Schroeder et al.
5,366,867 A 11/1994 Kawakami et al.
5,464,749 A 11/1995 Schwarzberg et al.
5,474,910 A 12/1995 Alfano
5,510,246 A 4/1996 Morgan
5,538,857 A 7/1996 Rosenthal et al.
5,541,069 A 7/1996 Mortensen et al.
5,552,272 A 9/1996 Bogart
5,558,839 A 9/1996 Matte et al.
5,582,982 A 12/1996 Cubbage et al.
5,585,241 A 12/1996 Lindmo
5,604,351 A 2/1997 Bisconte
5,606,413 A 2/1997 Bellus et al.
5,624,850 A 4/1997 Kumar et al.
5,648,274 A 7/1997 Chandler
5,652,939 A 7/1997 Verlinden et al.
5,653,939 A 8/1997 Hollis et al.
5,663,057 A 9/1997 Drocourt et al.
5,672,880 A 9/1997 Kain
5,681,530 A 10/1997 Kuster et al.
5,681,712 A 10/1997 Nelson
5,694,478 A 12/1997 Braier et al.
5,705,402 A 1/1998 Leland et al.
5,736,405 A 4/1998 Alfano et al.
5,744,322 A 4/1998 Krejcarek et al.
5,766,868 A 6/1998 Seto
5,792,617 A 8/1998 Rotman
5,814,454 A 9/1998 Ju
5,821,066 A 10/1998 Pyle et al.
5,828,716 A 10/1998 Bisconte de Saint Julien
5,852,498 A 12/1998 Youvan et al.
5,861,251 A 1/1999 Park et al.
5,861,270 A 1/1999 Nelis
5,861,306 A 1/1999 Pugh et al.
5,891,394 A 4/1999 Drocourt et al.
5,914,245 A 6/1999 Bylina et al.
5,958,790 A 9/1999 Cerny
5,968,766 A 10/1999 Powers
5,976,892 A 11/1999 Bisconte
5,981,180 A 11/1999 Chandler et al.
5,985,675 A 11/1999 Charm et al.
5,989,835 A 11/1999 Dunlay et al.
5,993,740 A 11/1999 Niiyama et al.
6,048,723 A 4/2000 Banes
6,051,393 A 4/2000 Jones et al.
6,051,395 A 4/2000 Rocco
6,121,055 A 9/2000 Hargreaves
6,122,396 A 9/2000 King et al.
6,130,931 A 10/2000 Laurila et al.
6,140,653 A 10/2000 Che
6,165,742 A 12/2000 Øfjord et al.
6,171,780 B1 1/2001 Pham et al.
6,200,762 B1 3/2001 Zlokarnik et al.
6,214,560 B1 4/2001 Yguerabide et al.
6,258,326 B1 7/2001 Modlin
6,259,807 B1 7/2001 Ravkin
6,268,222 B1 7/2001 Chandler et al.
6,274,384 B1 8/2001 Starzl et al.
6,287,849 B1 9/2001 McNerney et al.
6,306,589 B1 10/2001 Muller et al.
6,309,822 B1 10/2001 Fodor et al.
6,345,115 B1 2/2002 Ramm et al.
6,358,730 B1 3/2002 Kane
6,472,166 B1 10/2002 Wardlaw et al.
6,582,912 B1 6/2003 Rousseau et al.
6,602,704 B1 8/2003 Maxwell et al.
6,623,983 B1 9/2003 Terstappen et al.
6,649,418 B1 11/2003 Geisberg
6,664,528 B1 12/2003 Cartlidge et al.
6,710,879 B1 3/2004 Hansen et al.
6,727,071 B1 4/2004 Dunlay et al.
6,764,648 B1 7/2004 Roach et al.
6,790,655 B2 9/2004 Lyman et al.
6,792,132 B1 9/2004 Hara et al.
6,852,527 B2 2/2005 Chan et al.
6,919,960 B2 7/2005 Hansen et al.
6,969,607 B2 11/2005 Minton
7,068,365 B2 6/2006 Hansen et al.
7,110,585 B2 9/2006 Cork et al.
7,160,687 B1 1/2007 Kapur et al.
7,582,415 B2 9/2009 Straus
7,763,405 B2 7/2010 Wu et al.
7,763,455 B2 7/2010 Cima et al.
7,820,430 B2 10/2010 Weng et al.
8,021,848 B2 9/2011 Straus
9,090,462 B2 7/2015 Straus
9,290,382 B2 3/2016 Straus
9,632,085 B2 4/2017 Super et al.
9,643,180 B2 5/2017 Abrams et al.
2001/0039032 A1 11/2001 Matsumura et al.
2001/0039060 A1 11/2001 Siiman et al.
2002/0028471 A1 3/2002 Oberhardt
2002/0055092 A1 5/2002 Hochman
2002/0137106 A1 9/2002 Leung et al.
2003/0036058 A1 2/2003 Becker et al.
2003/0068638 A1 4/2003 Cork et al.
2003/0082516 A1 5/2003 Straus
2003/0143580 A1 7/2003 Straus
2003/0170613 A1 9/2003 Straus
2004/0048395 A1 3/2004 Lee et al.
2004/0171121 A1 9/2004 Leppla et al.
2004/0172000 A1 9/2004 Roe et al.
2004/0246483 A1 12/2004 Hansen et al.
2005/0013737 A1 1/2005 Chow et al.
2005/0053942 A1 3/2005 Kauppinen et al.
2005/0148085 A1 7/2005 Larsen
2005/0152955 A1 7/2005 Akhave et al.
2005/0153430 A1 7/2005 Ohtaka
2005/0191687 A1 9/2005 Wang et al.
2005/0220670 A1 10/2005 Palmieri et al.
2005/0221403 A1 10/2005 Gazenko
2005/0225766 A1 10/2005 Hansen et al.
2005/0226779 A1 10/2005 Oldham et al.
2006/0006067 A1 1/2006 Unger
2006/0046246 A1 3/2006 Zeng et al.
2006/0051816 A1 3/2006 Hsieh et al.
2006/0121055 A1 6/2006 Campbell et al.
2006/0129327 A1 6/2006 Kim et al.
2006/0188967 A1 8/2006 Nalin et al.
2006/0210435 A1 9/2006 Alavie et al.
2006/0216696 A1 9/2006 Goguen
2006/0256340 A1 11/2006 Hansen et al.
2006/0292552 A1 12/2006 Haquette et al.
2007/0014695 A1 1/2007 Yue et al.
2007/0172899 A1 7/2007 Graham et al.
2007/0184546 A1 8/2007 Farrelly et al.
2007/0202681 A1 8/2007 Wang
2007/0212681 A1 9/2007 Shapiro et al.
2007/0212747 A1 9/2007 Browne et al.
2008/0003571 A1 1/2008 McKernan et al.
2008/0014576 A1 1/2008 Jovanovich et al.
2008/0032328 A1 2/2008 Cline et al.
2008/0038738 A1 2/2008 Weigum et al.
2008/0200343 A1 8/2008 Clemens et al.
2008/0206099 A1 8/2008 Aruga et al.
2009/0075274 A1 3/2009 Slepnev et al.
2009/0137029 A1 5/2009 Breidenthal et al.
2009/0315987 A1 12/2009 Straus
2010/0028986 A1 2/2010 Hanafusa
2010/0248281 A1 9/2010 Straus
2011/0028563 A1 2/2011 Found
2012/0045826 A1 2/2012 Yantz et al.
2012/0046203 A1 2/2012 Walsh et al.

(56) References Cited

U.S. PATENT DOCUMENTS

| | | | |
|---|---|---|---|
| 2012/0149007 | A1 | 6/2012 | Abrams et al. |
| 2013/0011566 | A1 | 1/2013 | Colin et al. |
| 2013/0216454 | A1 | 8/2013 | Blecka et al. |
| 2015/0152467 | A1 | 6/2015 | Ingber et al. |
| 2016/0152694 | A1 | 6/2016 | Ambrosino et al. |
| 2016/0289729 | A1 | 10/2016 | Richards et al. |
| 2017/0029864 | A1 | 2/2017 | Straus |
| 2018/0088141 | A1 | 3/2018 | Vacic et al. |
| 2019/0324034 | A1 | 10/2019 | Bowers et al. |
| 2019/0366338 | A1 | 12/2019 | Yantz et al. |

FOREIGN PATENT DOCUMENTS

| | | | |
|---|---|---|---|
| CN | 101254482 | A | 9/2008 |
| DE | 19608320 | A1 | 8/1997 |
| DE | 19631997 | A1 | 2/1998 |
| DE | 19940810 | A1 | 5/2000 |
| EP | 0171174 | A2 | 2/1986 |
| EP | 0574977 | A1 | 12/1993 |
| EP | 0753732 | A2 | 1/1997 |
| EP | 1207394 | A2 | 5/2002 |
| EP | 1508374 | A2 | 2/2005 |
| JP | S62-501647 | A | 7/1987 |
| JP | H02-502405 | A | 8/1990 |
| JP | H02-278155 | A | 11/1990 |
| JP | H3-83598 | | 4/1991 |
| JP | H08-201391 | A | 8/1996 |
| JP | 10295362 | | 11/1998 |
| JP | H11-148901 | A | 6/1999 |
| JP | H11-346795 | A | 12/1999 |
| JP | 2000-508778 | A | 7/2000 |
| JP | 2000-509827 | A | 8/2000 |
| JP | 2000-275258 | A | 10/2000 |
| JP | 3102240 | B2 | 10/2000 |
| JP | 2001-224355 | A | 8/2001 |
| JP | 2001-512875 | A | 8/2001 |
| JP | 2002-125656 | A | 5/2002 |
| JP | 2003-294596 | A | 10/2003 |
| JP | 2004-070039 | A | 3/2004 |
| JP | 2004-125799 | A | 4/2004 |
| JP | 2005-502354 | A | 1/2005 |
| JP | 2006-087336 | A | 4/2006 |
| JP | 2006-162466 | A | 6/2006 |
| JP | 2007-526807 | A | 9/2007 |
| JP | 2008-96223 | A | 4/2008 |
| JP | 2008-513022 | A | 5/2008 |
| JP | 2009-513111 | A | 4/2009 |
| WO | 83/01581 | A1 | 5/1983 |
| WO | 86/04684 | A1 | 8/1986 |
| WO | 89/05456 | A1 | 6/1989 |
| WO | 92/05448 | A2 | 4/1992 |
| WO | 97/40181 | A1 | 10/1997 |
| WO | 9744664 | A1 | 11/1997 |
| WO | 98/38490 | A1 | 9/1998 |
| WO | 98/50577 | A1 | 11/1998 |
| WO | 99/08233 | A1 | 2/1999 |
| WO | 9920789 | A1 | 4/1999 |
| WO | 99/35483 | A1 | 7/1999 |
| WO | 99/36577 | A1 | 7/1999 |
| WO | 99/40176 | A1 | 8/1999 |
| WO | 9958948 | A2 | 11/1999 |
| WO | 0004382 | A1 | 1/2000 |
| WO | 0047766 | A1 | 8/2000 |
| WO | 01/57522 | A2 | 8/2001 |
| WO | 01/61348 | A1 | 8/2001 |
| WO | 03/022999 | A2 | 3/2003 |
| WO | 03/036290 | A1 | 5/2003 |
| WO | 03/073817 | A2 | 9/2003 |
| WO | 2005/082254 | A2 | 9/2005 |
| WO | 2006/032044 | A2 | 3/2006 |
| WO | 2006/106962 | A1 | 10/2006 |
| WO | 2007/038478 | A2 | 4/2007 |
| WO | 2007/145091 | A1 | 12/2007 |
| WO | 2008/005998 | A2 | 1/2008 |
| WO | 2008108027 | A1 | 9/2008 |
| WO | 2010/036808 | A1 | 4/2010 |
| WO | 2010/036827 | A1 | 4/2010 |
| WO | 2010/036829 | A1 | 4/2010 |
| WO | 2011/117545 | A1 | 9/2011 |
| WO | 2012/035302 | A1 | 3/2012 |
| WO | 2013/070730 | A2 | 5/2013 |
| WO | 2013/158666 | A1 | 10/2013 |
| WO | 2020/073015 | A1 | 4/2020 |
| WO | 2020/073018 | A2 | 4/2020 |

OTHER PUBLICATIONS

CCD detectors (http://www.astrosurf.com/re/chip.html) published online Feb. 22, 2001, from web archive http://web.archive.org/web/20010222014106/http://astrosurf.com/re/chip.html, retrieved Apr. 12, 2012, 5 pages.

Clean Technology, 1995, 5(8):60-61 (no english translation provided).

Colony Counter (http://www.topac.com/acolyte.html), retrieved Apr. 12, 2005, 3 pages.

Colony Counter Models and Specifications (http://biologics-inc.com/cc-models.htm), retreived Apr. 15, 2005, 3 pages.

Corkidi, 1998, COVASIAM: An Image Analysis Method That Allows Detection of Confluent Microbial Colonies and Colonies of Various Sizes for Automated Counting, Appl Environ Microbiol 64(4):1400-1404.

Crowther, 2000, Methods in Molecular Biology, The ELISA Guidebook, Humana Press, 425 pages.

Definition and Procedure for the Determination of the Method Detection Limit, Appendix B to 40 C.F.R. § 136, available at http://access.gpo.gov, retreived Nov. 20, 2007, pp. 343-346.

Digital Multi-Purpose High Resolution Colony and Plaque Counter, http://www.loats.com/mla.html, retreived Apr. 12, 2005, 3 pages.

Esteban, 1992, Improved Direct Epifluorescent Filter Technique for Rapid Bioburden Control in Intravenous Solutions, J. Parenter. Sci. Technol. 46146-149.

Findlay, 1993, Automated closed-vessel sstem for in vitro diagnostics based on polymerase chain reation, Clin Chem, 39(9):1927-1933.

Freydiere, 1991, Detection of Salmonellae by using Rambach agar and by a C8 esterase spot test, J. Clin Microbiol. 29(10):2357-2360.

Frost, 1921, Improved Technic for the Micro or Little Plate Method of Counting Bacteria in Milk, J. Infect. Dis. 28 (2):176-187.

Gite, 2018, A Rapid, Accurate, Single Molecule Counting Method Detects Clostridium difficile Toxin B in Stool Samples, Scientific Reports, 8:1-8.

Gray, 2011, Identification of micro-organisms after milliflex rapid detection—a possibility to Identify nonsterile findings in the milliflex rapid sterility test, Pda J Pharm Sci Technol. 65(1):42-54.

Graziani-Bowering, 1997, A quick, easy and inexpensive method for the isolation of human peripheral blood monocytes, J of Immunol Methods, 207(2):157-168.

Innovative Plate Holder for ProtoCOL, http://www.synbiosis.com retrieved Oct. 16, 2002, 2 pages.

Int Search Report and Written Op mailed Feb. 19, 2020, for Int Application No. PCT/US2019/054885, filed Oct. 4, 2019 (12 pages).

Int Search Report and Written Op mailed Jan. 13, 2010, for Int Application No. PCT/US2009/58237, filed Sep. 24, 2009, (10 pages).

Int Search Report and Written Op mailed Jan. 16, 2020, for Int Application No. PCT/US2019/054884, filed Oct. 4, 2019 (7 pages).

Int Search Report and Written Op mailed Jan. 17, 2020, for Int Application No. PCT/US2019/054887, filed Oct. 4, 2019 (12 pages).

Int Search Report and Written Op mailed Jan. 17, 2020, for Int Application No. PCT/US2019/054888, filed Oct. 4, 2019 (12 pages).

Int Search Report and Written Op mailed Jul. 10, 2019, for Int Application No. PCT/US2019/028397, filed Apr. 19, 2019 (11 pages).

Int Search Report and Written Op mailed Nov. 20, 2009, for Int Application No. PCT/US2009/058274, filed Sep. 24, 2009 (10 pages).

Kamentsky, 2001, Laser Scanning Cytometry, Methods Cell Biol. 63:51-87.

(56) References Cited

OTHER PUBLICATIONS

Kepner, 1994, Use of fluorochromes fo direct enumeration of total bacteria in environmental samples: past and present, Microbiol Rev. 58(4):603-615.
Kroll, 1989, A Laser-Light Pulse Counting Method for Automatic and Sensitive Counting Of Bacteria Stained with Acridine Orange, J. Appl. Bacteriol. 66:161-167.
Lamture, 1994, Direct Detection of Nucleic Acid Hybridization on the Surface of a Charge Coupled Device, Nucleic Acids Res. 22(11):2121-2125.
Loates Associates Inc., 1999, System Specifications http://www.loats.com/order_info.html, retrieved Apr. 12, 2005, 7 pages.
Loats, 1990, LAI High-Resolution Automated Colony Counting System-Mouse Lymphoma Assay: Performance Analysis, http://loats.com/docs/HRCCval/HRCCval.htm, pp. 1-11.
Logtenberg, 1985, Enumeration of (Auto) Antibody Producing Cells in Human Using the "Spot-ELISA," Immunol. Lett. 9:343-347.
London, 2010, An Automated System for Rapid Non-Destructive Enumeration of Growing Microbes, PLoS One 5(1): e8609, 16 pages.
Masuko, 1991, A Novel Method for Detection and Counting of Single Bacteria in a Wide Field Using an Ultra-High-Sensitivity TV Camera Without a Microscope, FEMS Microbiol. Lett. 81:287-290.
Masuko, 1991, Rapid Detection and Counting of Single Bacteria in a Wide Field Using a Photon-Counting TV Camera, FEMS Microbiol. Lett. 83:231-238.
Mignon-Godefroy, 1997, Solid Phase Cytometry for Detection of Rare Events, Cytometry 27, pp. 336-344.
Miraglia, 1999, Homogeneous Cell-and Bead-Based Assays for High Throughput Screening Using Fluorometric Microvolume Assay Technology, J. Biomol. Screen. 4:193-204.
Moore, 1998, Lymphocyte fractionation using immunomagnetic colloid and a dipole magnet flow sorter, J Biochem Biophys Methods, 37:11-33.
Nargessi, 1980, Magnetizable Sold-Phase Fluoroimmunoassay of Thyroxines by a Sequential Addition Technique. Clin Chem 26(12):1701-1703.
Nargessi, 1984, Immunoassays for Serum C-Reactive Protein Employing Fluorophore-Labelled Reactants, J. Immunol. Methods 71:17-24.
Nealson, 1978, Isolation, identification, and manipulation of luminous bacteria, Methods Enzymol. 57:153-166.
Nebe-von-Caron, 2000, Analysis of bacterial function by multi-colour fluorescence flow cytometry and single cell sorting, J. Microbiol Methods, 42(1):97-114.
Nelis, 2000, Enzymatic Detection of Coliforms and *Escherichia coli* Within 4 Hours, Water Air and Soil Pollut. 123:43-52.
Patterson, 1966, A wide angle camera for photographic search of the ocean bottom, SPIE, C-XII-1-8.
Perkinelmer, Inc., 2007, GeneScreenTM Hybridization Transfer Membranes: transfer and detection protocols, Application Notes, available at http://las.perkinelmer.com, retrieved Feb. 27, 2007.
Porter, 1980, The use of DAPI for identifying and counting aqquatic microflora, Limnol Oceanogr. 25(5):943-948.
Rousseau, 1999, New Miniaturized Highly Sensitive Immunassay Device for Quantitative Measurement of Soluble or Particular Antigen or Antibodies in a Liquid Sample, Clin. Chem. 45(9):1685-1687.
Schultz, 2000, Single Target Molecule Detection with Nonbleaching Multicolor Optical Immunolabels, Proc. Natl. Acad. Sci. USA 97(3):996-1001.
Sorcerer Automated Colony Counting, 2002, Perceptive Instruments, 2 pages.
Supplementary European Search Report and Written Opinion for European Application No. EP 09816857, date of mailing: Mar. 20, 2012, 8 pages.
Susa, 1998, Legionella pneumophila infection in intratracheally inoculated T cell-depleted or -nondepleted A/J mice, J Immunol, 160: 316-321.
Technical Specification http://www.perceptive.co.uk/products/_scc/techspec.html, retrieved Apr. 12, 2005, 2 pages.
Texas Instruments TC211 192×165 Pixel CCD Image Sensor description dated Jan. 1990, 13 pages.
Thomas, 2000, Making gold nanoparticles glow: enhanced emission from a surface-bound fluoroprobe, J Am Chem Soc, 122:2655-2656.
Tibbe, 1999, Optical Tracking and Detection of Immunomagnetically Selected and Aligned Cells, Nature Biotechnol. 17:1210-1213.
Van Pouche, 2000, A 210-min Solid Phase Cytometry Test for the Enumeration of *Escherichia coli* in Drinking Water, J. Appl. Microbiol. 89:390-396.
Van Poucke, 1999, Solid Phase Cytometry-Based Enzymatic Detection of Coliforms in Drinking Water Within 4 h, Water Supply 17:67-72.
Van Poucke, 2000, Rapid Detection of Fluorescent and Chemiluminescent Total Coliforms and *Escherichia coli* on Membrane Filters J. Microbiol. Methods 42:233-214.
Vidon, 2001, A Simple Chemiluminescence-Based Method for Rapid Enumeration of *Listeria* spp. Microcolonies, J. Appl. Microbiol. 90:988-993.
Viinikka, 1981, A Two-Site Immunofluorometric Assay for Human Placental Lactogen, Clin. Chim. Acta. 114:1-9.
Waggoner, 1990, Fluorescent Probes for Cytometry, Flow Cytometry and Sorting, Wiley-Liss, 209-225.
Wellman, 2006, Magenetically-Assisted Transport Evanescent Field Fluoroimmunoassay, Anal, Chem. 78:4450-4456.
Wilson, 1995, Use of the IUL Countermat Automatic Colony Counter for Spiral Plated Total Viable Counts, Appl. Environ. Microbiol. 61:3158-3160.
Wolniak, 2004, BSCI 427 Principles of Microscopy Fall 2004 Syllabus, http://www.life.umd.edu/cbmg/faculty/wolniak/wolniakmicro.html, retrieved Nov. 8, 2007, 8 pages.
Yasui, 1997, Imaging of Lactobacillus brevis Single Cells and Microcolonies Without a Microscope by an Ultrasensitive Chemiluminescent Enzyme Immunoassay with a Photon-counting Television Camera, Appl. Environ. Microbiol. 63:4528-4533.
Zhao, 2004, Competitive Immunoassay for Microliter Protein Samples with Magnetic Beads and Near-infared Fluorescence Detection, Anal Chem. 76:1871-1876.
EP Search Report and Supplementary Search Report issued on Dec. 15, 2022 by the EPO for application 19870007.2, filed on Apr. 9, 2020 and published as EP3861345 (Inventor—Straus, et al.; Applicant—First Light) (7 pages).
Brazelton de Cardenas et al. "Evaluation of rapid phenotypic identification and antimicrobial susceptibility testing in a pediatric oncology center" Diagnostic microbiology and infectious disease, vol. 89, No. 1, Jun. 23, 2017, pp. 52-57.

| Bacterial Target | FISH Probes | Labeled | Final Concentration | Sequence | Comments | |
|---|---|---|---|---|---|---|
| E. coli | Eco469 | Alexa647N | 0.3 μM | /5Alex647N/GTCAATGAGCAAAGG | Eco0649 H1 Went with Eco0649 | (SEQ ID NO: 1) |
| | Eco469 H1 | No label | 3 μM | ACTCCCTTCCTCCCCGCTG | | (SEQ ID NO: 2) |
| | Eco469 H2 | No label | 3 μM | GGTGCTTCTTCTGCGGGTAA | | (SEQ ID NO: 3) |
| | Eco649 | Alexa647 | 0.3 μM | /5Alex647N/TACGAGACTCAAGCT | Eco0649 H1 Went with Eco0649 | (SEQ ID NO: 4) |
| | Eco649 H1 | No label | 3 μM | AGTATCAGATGCAGTTCCCAG | | (SEQ ID NO: 5) |
| | Eco649 H2 | No label | 3 μM | TTCGCACCTGAGCGTCAGTC | | (SEQ ID NO: 6) |
| P. aeruginosa | Pae002 | Alexa647N | 0.2 μM | /5Alex647N/CTTCAAAGATCCTTT/3AlexF647N/ | All probes were used in same mixture | (SEQ ID NO: 7) |
| | Pae002 H1 | No label | 1.5 μM | CGCGTACGGGGCTATCACCCA | | (SEQ ID NO: 8) |
| | Pae002 H2 | No label | 1.5 μM | GCTCCGTCCTACTCGATTTCA | | (SEQ ID NO: 9) |
| | Pae004 H1 | No label | 1.5 μM | GGGCTAATCCCCGTTCGCTCG | | (SEQ ID NO: 10) |
| | Pae004 H2 | No label | 3 μM | ACTTTCCAGAGCGTTCCGCTA | | (SEQ ID NO: 11) |
| | Pae005 H2 | No label | 1.5 μM | CCAGTGAGATCTCATCTTGAG | | (SEQ ID NO: 12) |
| | Pae005 H3 | No label | 3 μM | CGTCGTAGTCTTCGACGGCCC | | (SEQ ID NO: 13) |
| K. pneumoniae | Kpn001 | Alexa647N | 0.6 μM | /5Alex647N/CACCTACACACCAGCG/3AlexF647N/ | All probes were used in same mixture | (SEQ ID NO: 14) |
| | Kpn003_2 | Alexa647 | 0.2 μM | /5Alex647N/CTTCGACTGGTCTCAGC/3AlexF647N/ | | (SEQ ID NO: 15) |
| | Kleb001 H1 | No label | 6 μM | TGCCTTCTCCCGAAGTTACGG | | (SEQ ID NO: 16) |
| | Kleb235 H3 | No label | 1.5 μM | GCCAGCTGGTATCTTCGACTG | | (SEQ ID NO: 17) |
| | Kpn003 H3 | No label | 6 μM | ACAGTTGCAGCCAGCTGGTAT | | (SEQ ID NO: 18) |
| E. faecalis | UTI 338 A | Alexa647N | 0.6 μM | /5Alex647N/ACTGCTGCCT | All probes were used in same mixture | (SEQ ID NO: 19) |
| | UTI 338 B | Alexa647N | 0.6 μM | CCCGTAGGAGT/3AlexF647N/ | | (SEQ ID NO: 20) |
| | Eco338 H1 | No label | 3 μM | CTGGACCGTGTCTCAGTTC | | (SEQ ID NO: 21) |
| | Eco338 H2 | No label | 3 μM | CCCATTGTGCAATATTCCCC | | (SEQ ID NO: 22) |
| | Entero338 H1 | No label | 3 μM | TGGGCCGTGTCTCAGTCC | | (SEQ ID NO: 23) |
| | Entero338 H2 | No label | 3 μM | TCCATTGCCGAAGATTCCCT | | (SEQ ID NO: 24) |
| | | | | | | (SEQ ID NO: 25) |

FIG. 17

| Target | Isolates detected at 600 CFU per assay |
| --- | --- |
| *E. coli* | 11/11 |
| *K. pneumoniae* | 11/11 |
| *P. aeruginosa* | 11/11 |
| *P. mirabilis* | 6/6 |
| *Enterococcus spp.* | 6/6 |

| Bacterial Target | FISH Probes | Labeled | Final Concentration | Sequence | |
|---|---|---|---|---|---|
| E. coli | Eco469 | Alexa647N | 0.6 µM | /5Alex647N/GTCAATGAGCAAAGG | (SEQ ID NO: 26) |
| | Eco469 H1 | No label | 3 µM | ACTCCCTTCCTCCCCGCTG | (SEQ ID NO: 27) |
| | Eco469 H2 | No label | 3 µM | GGTGCTTCTTCTGCGGGTAA | (SEQ ID NO: 28) |
| P. aeruginosa | Pae002 | Alexa647N | 0.4 µM | /5Alex647N/CTTCAAAGATCCTTT/3AlexF647N/ | (SEQ ID NO: 29) |
| | Pae002 H1 | No label | 1.5 µM | CGCGTACGGGGCTATCACCCA | (SEQ ID NO: 30) |
| | Pae002 H2 | No label | 1.5 µM | GCTCCGTCCTACTCGATTTCA | (SEQ ID NO: 31) |
| | Pae004 H1 | No label | 1.5 µM | GGGCTAATCCCCGTTCGCTCG | (SEQ ID NO: 32) |
| | Pae004 H2 | No label | 5 µM | ACTTTCCAGAGCGTTCCGCTA | (SEQ ID NO: 33) |
| | Pae005 H2 | No label | 1.5 µM | CCAGTGAGATCTCATCTTGAG | (SEQ ID NO: 34) |
| | Pae005 H3 | No label | 5 µM | CGTCGTAGTCTTCGACGGCCC | (SEQ ID NO: 35) |
| K. pneumoniae | Kpn003_2 | Alexa647N | 0.4 µM | /5Alex647N/CTTCGACTGGTCTCAGC/3AlexF647N/ | (SEQ ID NO: 36) |
| | Kleb001 H1 | No label | 6 µM | TGCCTTCTCCCGAAGTTACGG | (SEQ ID NO: 37) |
| | Kleb235 H3 | No label | 1.5 µM | GCCAGCTGGTATCTTCGACTG | (SEQ ID NO: 38) |
| | Kpn003 H3 | No label | 6 µM | ACAGTTGCAGCCAGCTGGTAT | (SEQ ID NO: 39) |
| E. faecalis | L1_Ent003 (LNA) | Alexa647N | 0.3 µM | /5Alex647N/CAAA+AAC+A+ACK+GG | (SEQ ID NO: 40) |
| | L2_Ent004 (LNA) | Alexa647N | 0.3 µM | /5Alex647N/TGC+ATT+CCTTA | (SEQ ID NO: 41) |
| | Ent003 H1 | No label | 5.6 µM | AGGAATATCAACCTGTTRTCC | (SEQ ID NO: 42) |
| | Ent003 H2_1 | No label | 5.6 µM | CTMCTGCGTCCCTCCATTGCTCA | (SEQ ID NO: 43) |
| | Ent003 H3 | No label | 5.6 µM | GTTTRCGGTACGGGCMGYTGT | (SEQ ID NO: 44) |
| | Ent003 H4 | No label | 5.6 µM | TTTCTCACTAGAAGCTTTTCT | (SEQ ID NO: 45) |
| | Ent004 H4_2 | No label | 5.6 µM | CAGGAACTTCGSTACTATTAT | (SEQ ID NO: 46) |
| | Ent004 H2 Efis | No label | 5.6 µM | GGACATGCACTTCCAATCGCA | (SEQ ID NO: 47) |
| P. mirabilis | Prot631 (LNA) | Alexa647N | 0.6 µM | /5Alex647N/C+TGACTTAATT+GACC | (SEQ ID NO: 48) |
| | Prot631 H1 | No label | 3 µM | CCTGCGTGCGCTTTACGCC | (SEQ ID NO: 49) |
| | Prot631 H2 | No label | 3 µM | TTAAGCTCGGGGCTTTCACA | (SEQ ID NO: 50) |

FIG. 21

| Bacteria Tested For Cross-reactivity | Reason for inclusion |
|---|---|
| *K. oxytoca* | UTI pathogen |
| *K. pneumoniae* | UTI pathogen, close relative |
| *P. aeruginosa* | UTI pathogen |
| *P. mirabilis* | UTI pathogen |
| *E. faecium* | UTI pathogen |
| *E. faecalis* | UTI pathogen |
| *S. aureus* | UTI pathogen, rare skin commensal |
| *S. saprophyticus* | UTI pathogen |
| *S. agalactiae* | UTI pathogen |
| *S. epidermidis* | Skin commensal |
| *A. baumanii* | UTI pathogen |
| *M. luteus* | Skin commensal |
| *S. enterica* | Close relative |
| *K. aerogenes* | Close relative, UTI pathogen |
| *C. fruendii* | Close relative, UTI pathogen |
| *S. marcescens* | UTI pathogen |

FIG. 22

| Bacterial Target | FISH Probes | Labeled | Final Concentration | Sequence | Comments | |
|---|---|---|---|---|---|---|
| E. coli | Eco649 | Alexa647N | 0.6 μM | /5Alex647N/GTCAATGAGCAAAGG | Eco0649 H1 Went with Eco0649 | (SEQ ID NO: 51) |
| | Eco649 H1 | No label | 3 μM | ACTCCCTTCCTCCCGCTG | | (SEQ ID NO: 52) |
| | Eco649 H2 | No label | 3 μM | GGTGCTTCTTCTGCGGGTAA | | (SEQ ID NO: 53) |
| | Eco649 | Alexa647N | 0.6 μM | /5Alex647N/TACGAGACTCAAGCT | Eco0649 H1 Went with Eco0649 | (SEQ ID NO :54) |
| | Eco649 H1 | No label | 3 μM | AGTATCAGATGCAGTTCCCAG | | (SEQ ID NO: 55) |
| | Eco649 H2 | No label | 3 μM | TTCGCACCTGAGCGTCAGTC | | (SEQ ID NO: 56) |
| P. aeruginosa | Pae002 | Alexa647N | 0.4 μM | /5Alex647N/CTTCAAAGATCCTTT/3AlexF647N/ | All probes were used in same mixture | (SEQ ID NO: 57) |
| | Pae002 H1 | No label | 1.5 μM | CGCGTACGGGGCTATCACCCA | | (SEQ ID NO: 58) |
| | Pae002 H2 | No label | 1.5 μM | GCTCCGTCCTACTCGATTTCA | | (SEQ ID NO: 59) |
| | Pae004 H1 | No label | 1.5 μM | GGGCTAATGCCCGTTCGCTCG | | (SEQ ID NO: 60) |
| | Pae004 H2 | No label | 5 μM | ACTTTCCAGAGCGTTCCGCTA | | (SEQ ID NO: 61) |
| | Pae005 H2 | No label | 1.5 μM | CCAGTGAGATCTCATCTTGAG | | (SEQ ID NO: 62) |
| | Pae005 H3 | No label | 5 μM | CGTCGTAGTCTTCGACGGCCC | | (SEQ ID NO: 63) |
| K. pneumoniae | Kpn001 | Alexa647N | 0.6 μM | /5Alex647N/CACCTACACACCAGCG/3AlexF647N/ | All probes were used in same mixture | (SEQ ID NO: 64) |
| | Kpn003_2 | Alexa647N | 0.2 μM | /5Alex647N/CTTCGACTGGTCTCAGC/3AlexF647N/ | | (SEQ ID NO: 65) |
| | Kleb001 H1 | No label | 6 μM | TGCCTTCTCCCGAAGTTACGG | | (SEQ ID NO: 66) |
| | Kleb235 H3 | No label | 1.5 μM | GCCAGCTGGTATCTTCGACTG | | (SEQ ID NO: 67) |
| | Kpn003 H3 | No label | 6 μM | ACAGTTGCAGCCAGCTGGTAT | | (SEQ ID NO: 68) |
| E. faecalis | L1_Ent003 (LNA) | Alexa647N | 0.3 μM | /5Alex647N/CAAA+AAC+A+ACX+GG | All probes were used in same mixture | (SEQ ID NO: 69) |
| | L2_Ent004 (LNA) | Alexa647N | 0.3 μM | /5Alex647N/TGC+ATT+CCTTA | | (SEQ ID NO: 70) |
| | Ent003 H1 | No label | 5.6 μM | AGGAATATCAACCTGTTRTCC | | (SEQ ID NO: 71) |
| | Ent003 H2_1 | No label | 5.6 μM | CTMCTGCGTCCCTCCATTGCTCA | | (SEQ ID NO: 72) |
| | Ent003 H3 | No label | 5.6 μM | GTTTRCGGTACGGGCMGYTGT | | (SEQ ID NO: 73) |
| | Ent003 H4 | No label | 5.6 μM | TTTCTCACTAGAAGCTTTTCT | | (SEQ ID NO: 74) |
| | Ent004 H4_2 | No label | 5.6 μM | CAGGAACTTCGSTACTATTAT | | (SEQ ID NO: 75) |
| | Ent004 H2 Efs | No label | 5.6 μM | GGACATGCACTTCCAATCGCA | | (SEQ ID NO: 76) |

FIG. 23

| Bacterial Target | FISH Probes | Labeled | Color Channel | Final Concentration | Sequence |
|---|---|---|---|---|---|
| E. coli | Eco469 | Alexa647N | Red | 0.8 μM | /5Alex647N/GTCAATGAGCAAAGG |
| | Eco469 H1 | No label | N/A | 3 μM | ACTCCCTTCCTCCCCGCTG |
| | Eco469 H2 | No label | N/A | 3 μM | GGTGCTTCTTCTGCGGGTAA |
| P. aeruginosa | Pae002 | Alexa532N | Yellow | 0.2 μM | /5Alex532N/CTTCAAAGATCCTTT/3Alex532N/ |
| | Pae002 H1 | No label | N/A | 1.5 μM | CGCGTACGGGGCTATCACCCA |
| | Pae002 H2 | No label | N/A | 1.5 μM | GCTCCGTCCTACTCGATTTCA |
| | Pae004 H1 | No label | N/A | 1.5 μM | GGGCTAATCCCCGTTCGCTCG |
| | Pae004 H2 | No label | N/A | 5 μM | ACTTTCCAGAGCGTTCCGCTA |
| | Pae005 H2 | No label | N/A | 1.5 μM | CCAGTGAGATCTCATCTTGAG |
| | Pae005 H3 | No label | N/A | 5 μM | CGTCGTAGTCTTCGACGGCCC |
| K. pneumoniae | Kpn003_2 | Alexa488N | Green | 0.2 μM | /5Alex488N/CTTCGACTGGTCTCAGC/3AlexF488N/ |
| | Kleb001 H1 | No label | N/A | 6 μM | TGCCTTCTCCCGAAGTTACGG |
| | Kleb235 H3 | No label | N/A | 1.5 μM | GCCAGCTGGTATCTTCGACTG |
| | Kpn003 H3 | No label | N/A | 6 μM | ACAGTTGCAGCCAGCTGGTAT |
| K. oxytoca | Koxy_1717 | Alexa568N | Orange | 0.6 μM | /5Alex568N/CTTCATGAGCAAGT/3Alex568N/ |
| | Koxy_1717 H1 | No label | N/A | 3 μM | ACTTACCATCAGCGTGCCTT |
| | Koxy_1717 H2 | No label | N/A | 3 μM | CTGGTATCTTCGACTGATTT |

(SEQ ID NO: 77)
(SEQ ID NO: 78)
(SEQ ID NO: 79)
(SEQ ID NO: 80)
(SEQ ID NO: 81)
(SEQ ID NO: 82)
(SEQ ID NO: 83)
(SEQ ID NO: 84)
(SEQ ID NO: 85)
(SEQ ID NO: 86)
(SEQ ID NO: 87)
(SEQ ID NO: 88)
(SEQ ID NO: 89)
(SEQ ID NO: 90)
(SEQ ID NO: 91)
(SEQ ID NO: 92)
(SEQ ID NO: 93)

FIG. 27

| Bacterial Target | FISH Probes | Labeled | Final Concentration | Sequence | # of Samples used the probe set | |
|---|---|---|---|---|---|---|
| E. coli | Eco469 | Alexa647N | 0.6 μM | /5Alex647N/GTCAATGAGCAAAGG | 19 | (SEQ ID NO: 94) |
| | Eco469 H1 | No label | 3 μM | ACTCCCTTCCTCCCCGCTG | | (SEQ ID NO: 95) |
| | Eco469 H2 | No label | 3 μM | GGTGCTTCTTCTGCGGGTAA | | (SEQ ID NO: 96) |
| | Eco469 | Alexa647N | 0.3 μM | /5Alex647N/GTCAATGAGCAAAGG | 17 | (SEQ ID NO: 97) |
| | Eco469 H1 | No label | 3 μM | ACTCCCTTCCTCCCCGCTG | | (SEQ ID NO: 98) |
| | Eco469 H2 | No label | 3 μM | GGTGCTTCTTCTGCGGGTAA | | (SEQ ID NO: 99) |
| | Eco649 | Alexa647N | 0.3 μM | /5Alex647N/TACGAGACTCAAGCT | 12 | (SEQ ID NO: 100) |
| | Eco649 H1 | No label | 3 μM | AGTATCAGATGCAGTTCCCAG | | (SEQ ID NO: 101) |
| | Eco649 H2 | No label | 3 μM | TTCGCACCTGAGCGTCAGTC | | (SEQ ID NO: 102) |

FIG. 32

| Target | Antibiotic | Essential Agreement |
|---|---|---|
| *E. coli* | Ciprofloxacin | 100% |
| | Trimethoprim/ sulfamethoxazole | 100% |
| | Meropenem | 100% |
| | Ceftazidime | 100% |
| | Nitrofurantoin | 75% (3/4) |
| *P. aeruginosa* | Ciprofloxacin | 100% |
| | Meropenem | 100% |
| | Ceftazidime | 100% |
| *Klebsiella spp. (K. pneumoniae and K. oxytoca)* | Ciprofloxacin | 100% |
| | Trimethoprim/ sulfamethoxazole | 89% (8/9) |
| | Meropenem | 100% |
| | Ceftazidime | 100% |
| | Nitrofurantoin | 100% |
| *P. mirabilis* | Ciprofloxacin | 100% |
| | Trimethoprim/ sulfamethoxazole | 100% |
| | Meropenem | 100% |
| | Ceftazidime | 100% |

FIG. 35

| Bacterial Target | FISH Probes | Labeled | Final Concentration | Sequence | |
|---|---|---|---|---|---|
| E. coli | Eco649 | Alexa647N | 0.3 µM | /5Alex647N/GTCAATGAGCAAAGG | (SEQ ID NO: 103) |
| | Eco649 H1 | No label | 3 µM | ACTCCCTTCCTCCCCGCTG | (SEQ ID NO: 104) |
| | Eco649 H2 | No label | 3 µM | GGTGCTTCTTCTGCGGGTAA | (SEQ ID NO: 105) |
| P. aeruginosa | Pae002 | Alexa647N | 0.2 µM | /5Alex647N/CTTCAAAGATCCTTT/3AlexF647N/ | (SEQ ID NO: 106) |
| | Pae002 H1 | No label | 1.5 µM | CGCGTACGGGGCTATCACCCA | (SEQ ID NO: 107) |
| | Pae002 H2 | No label | 1.5 µM | GCTCCGTCCTACTCGATTTCA | (SEQ ID NO: 108) |
| | Pae004 H1 | No label | 1.5 µM | GGGCTAATCCCCGTTCGCTCG | (SEQ ID NO: 109) |
| | Pae004 H2 | No label | 5 µM | ACTTTCCAGAGCGTTCCGCTA | (SEQ ID NO: 110) |
| | Pae005 H2 | No label | 1.5 µM | CCAGTGAGATCTCATCTTGAG | (SEQ ID NO: 111) |
| | Pae005 H3 | No label | 5 µM | CGTCGTAGTCTTCGACGGCCC | (SEQ ID NO: 112) |
| K. pneumoniae | Kpn003_2 | Alexa647N | 0.2 µM | /5Alex647N/CTTCGACTGGTCTCAGC/3AlexF647N/ | (SEQ ID NO: 113) |
| | Kleb001 H1 | No label | 6 µM | TGCCTTCTCCCGAAGTTACGG | (SEQ ID NO: 114) |
| | Kleb235 H3 | No label | 1.5 µM | GCCAGCTGGTATCTTCGACTG | (SEQ ID NO: 115) |
| | Kpn003 H3 | No label | 6 µM | ACAGTTGCAGCCAGCTGGTAT | (SEQ ID NO: 116) |
| K. oxytoca | Kox001_3 | Alexa647N | 0.6 µM | /5Alex647N/TCACYTACCATCAG/3AlexF647N/ | (SEQ ID NO: 117) |
| | Kleb001 H1 | No label | 3 µM | TGCCTTCTCCCGAAGTTACGG | (SEQ ID NO: 118) |
| | Kleb235 H3 | No label | 3 µM | GCCAGCTGGTATCTTCGACTG | (SEQ ID NO: 119) |
| P. mirabilis | Prot631- 2 dye | Alexa647N | 0.6 µM | /5Alex647N/C+TGACTTAATT+GACC | (SEQ ID NO: 120) |
| | Prot631 H1 | No label | 3 µM | CCTGCGTGCGCTTTACGCC | (SEQ ID NO: 121) |
| | Prot631 H2 | No label | 3 µM | TTAAGCTCGGGGCTTTCACA | (SEQ ID NO: 122) |

FIG. 36

| Antibiotics | Concentration 1 (μg/mL) | Concentration 2 (μg/mL) |
|---|---|---|
| Ciprofloxacin (CIP) | 0.25 | 0.5 |
| Nitrofurantoin (NIT) | 32 | 64 |
| Cefazolin (CFZ) | 8 | 16 |
| Trimethoprim/ Sulfamethoxazole (TMP/SXT) | 1/19 | 2/38 |

| Bacteria / Target | FISH Probes | Labeled | Final Concentration | Sequence | |
|---|---|---|---|---|---|
| E. coli | Eco469 | Alexa647 N | 0.3 μM | /5Alex647N/GTCAATGAGCAAAGG | (SEQ ID NO: 123) |
| | Eco469 H1 | No label | 3 μM | ACTCCCTTCCTCCCCGCTG | (SEQ ID NO: 124) |
| | Eco469 H2 | No label | 3 μM | GGTGCTTCTTCTGCGGGTAA | (SEQ ID NO: 125) |

FIG. 39

| | CIP Conc. (µg/mL) | NIT Conc. (µg/mL) |
|---|---|---|
| MultiPath call | R | S |
| CLSI call | R | S |

| | TMP/SXT Conc. (μg/mL) | CEF Conc. (μg/mL) |
|---|---|---|
| MultiPath call | R | R |
| CLSI call | R | R |

| Target | Antibiotic | Essential Agreement | Categorical Agreement |
|---|---|---|---|
| *E. coli* | CIP | 100% | 100% |
| | CFZ | 100% | 100% |
| | NIT | 100% | 100% |
| | TMP/SXT | 100% | 100% |
| *P. aeruginosa* | CIP | 100% | 100% |
| | NIT | 100% | 100% |
| *Klebsiella spp.* | CIP | 100% | 100% |
| | CFZ | 100% | 100% |
| | NIT | 100% | 60% |
| | TMP/SXT | 100% | 100% |

FIG. 42

| Inoculum (CFU/mL) | MIC (µg/mL of NIT) |
|---|---|
| 2.E+03 | 8 |
| 2.E+04 | 8 |
| 1.E+05 | 8 |
| 2.E+05 | 16 |
| 3.E+05 | 16 |
| 5.E+05 | 8 |
| 2.E+06 | 16 |
| 6.E+06 | 16 |
| 6.E+07 | 16 |

| Bacterial Target | FISH Probes | Labeled | Final Concentration | Sequence | Comment | |
|---|---|---|---|---|---|---|
| E. coli | P2 Coli Dye-10 | Alexa647N | 0.3 µM | /5Alex647N/GTCAATGAGCAAAGG | Not specific to E. coli | (SEQ ID NO: 126) |
| | P1 Universal Dye | No label | 3 µM | ACTCCCTTCCTCCCCGCTG | Not specific to E. coli | (SEQ ID NO: 127) |
| | P1 coli Helper 1 | No label | 3 µM | GGTGCTTCTTCTGCGGGTAA | Not specific to E. coli | (SEQ ID NO: 128) |
| | Eco001 | Alexa647N | 1.2 µM | /5Alex647N/GTATTAACTTTACTCC/3AlexF647N/ | Specific to E. coli | (SEQ ID NO: 129) |
| | Eco001 H1 | No label | 1.5 µM | GGGTAACGTCAATGAGCAAAG | Specific to E. coli | (SEQ ID NO: 130) |
| | Eco001 H2 | No label | 1.5 µM | CTTCCTCCCCGCTGAAAGTAC | Specific to E. coli | (SEQ ID NO: 131) |
| P. aeruginosa | Pae002 | Alexa647N | 600nM | /5Alex647N/CTTCAAAGATCCTTT/3AlexF647N/ | Specific to P. aeruginosa | (SEQ ID NO: 132) |
| | Pae004 | Alexa647N | 600nM | /5Alex647N/AAATCAATGAAGCTTAA/3AlexF647N/ | Specific to P. aeruginosa | (SEQ ID NO: 133) |
| | Pae002 H1 | No label | 3 µM | CGCGTACGGGGCTATCACCCA | Specific to P. aeruginosa | (SEQ ID NO: 134) |
| | Pae002 H2 | No label | 3 µM | GCTCCGTCCTACTCGATTTCA | Specific to P. aeruginosa | (SEQ ID NO: 135) |
| | Pae004 H1 | No label | 3 µM | GGGCTAATCCCCGTTCGCTCG | Specific to P. aeruginosa | (SEQ ID NO: 136) |
| | Pae004 H2 | No label | 3 µM | ACTTTCCAGAGCGTTCCGCTA | Specific to P. aeruginosa | (SEQ ID NO: 137) |
| K. pneumoniae | Kpn001 | Alexa647N | 1 µM | /5Alex647N/CACCTACACACCAGCG/3AlexF647N/ | Specific to K. pneumoniae | (SEQ ID NO: 138) |
| | Kpn003_2 | Alexa647N | 0.4 µM | /5Alex647N/CTTCGACTGGTCTCAGC/3AlexF647N/ | Specific to K. pneumoniae | (SEQ ID NO: 139) |
| | Kleb008 H1 | No label | 6 µM | TGCCTTCTCCGAAGTTACGG | Specific to K. pneumoniae | (SEQ ID NO: 140) |
| | Kleb235 H3 | No label | 6 µM | GCCAGCTGGTATCTTCGACTG | Specific to K. pneumoniae | (SEQ ID NO: 141) |
| | Kpn008 H3 | No label | 6 µM | ACAGTTGCAGCCAGCTGGTAT | Specific to K. pneumoniae | (SEQ ID NO: 142) |

FIG. 45

| Target | Off-target microbe added | Essential Agreement | Categorical Agreement |
|---|---|---|---|
| 1E+05 CFU per assay for E. coli | 1e+05 CFU per assay | 100% | 100% |
| | 1E+06 CFU per assay | 100% | 100% |
| | 1E+07 CFU per assay | 96% | 100% |

| Fold Growth threshold of 4.5 | | | MIC in ug/ml according to | | Resistance profile | | |
|---|---|---|---|---|---|---|---|
| | Bug | ABX | MultiPath | CLSI Compliant BMD | MP | BMD | Agree/Disagree |
| E.coli with S.aureus | 1e5E.coli | LVX | 16 | 16 | R | R | Agree |
| | with 1e5 | CIP | 256 | 256 | R | R | Agree |
| | S.aureus | NIT | 8 | 8 | S | S | Agree |
| | 1e5E.coli | LVX | 16 | 16 | R | R | Agree |
| | with 1e6 | CIP | 256 | 256 | R | R | Agree |
| | S.aureus | NIT | 8 | 8 | S | S | Agree |
| | 1e5E.coli | LVX | 16 | 16 | R | R | Agree |
| | with 1e7 | CIP | 256 | 256 | R | R | Agree |
| | S.aureus | NIT | 8 | 8 | S | S | Agree |
| E.coli with S.epidermis | 1e5E.coli | LVX | 16 | 16 | R | R | Agree |
| | with 1e5 | CIP | 256 | 256 | R | R | Agree |
| | S.epiderm | NIT | 8 | 8 | S | S | Agree |
| | 1e5E.coli | LVX | 16 | 16 | R | R | Agree |
| | with 1e6 | CIP | 256 | 256 | R | R | Agree |
| | S.epiderm | NIT | 4 | 8 | S | S | Agree |
| | 1e5E.coli | LVX | 16 | 16 | R | R | Agree |
| | with 1e7 | CIP | 256 | 256 | R | R | Agree |
| | S.epiderm | NIT | 16 | 8 | S | S | Agree |
| E.coli with Citrobacter | 1e5E.coli | LVX | 16 | 16 | R | R | Agree |
| | with 1e5 | CIP | 256 | 256 | R | R | Agree |
| | Citro | NIT | 8 | 8 | S | S | Agree |
| | 1e5E.coli | LVX | 16 | 16 | R | R | Agree |
| | with 1e6 | CIP | 256 | 256 | R | R | Agree |
| | Citro | NIT | 4 | 8 | S | S | Agree |
| | 1e5E.coli | LVX | 16 | 16 | R | R | Agree |
| | with 1e7 | CIP | 256 | 256 | R | R | Agree |
| | Citro | NIT | <1 | 8 | S | S | Agree |

FIG. 48

| Fold growth threshold of 1.5 | | | MIC in ug/ml According to: | | Resistance profile | | |
|---|---|---|---|---|---|---|---|
| | Bug | ABX | MultiPath | CLSI Compliant BMD | MP | BMD | Agree/Disagree |
| E.coli with M.luteus | 1e5E.coli with 1e5 M.lut | LVX | 32 | 16 | R | R | Agree |
| | | CIP | 256 | 256 | R | R | Agree |
| | | NIT | 8 | 8 | S | S | Agree |
| | 1e5E.coli with 1e6 M.lut | LVX | 16 | 16 | R | R | Agree |
| | | CIP | 256 | 256 | R | R | Agree |
| | | NIT | 8 | 8 | S | S | Agree |
| | 1e5E.coli with 1e7 M.lut | LVX | 32 | 16 | R | R | Agree |
| | | CIP | 256 | 256 | R | R | Agree |
| | | NIT | 4 | 8 | S | S | Agree |
| E.coli with A.baumannii | 1e5E.coli with 1e5 Abaum | LVX | 16 | 16 | R | R | Agree |
| | | CIP | 256 | 256 | R | R | Agree |
| | | NIT | 8 | 8 | S | S | Agree |
| | 1e5E.coli with 1e6 Abaum | LVX | 16 | 16 | R | R | Agree |
| | | CIP | 256 | 256 | R | R | Agree |
| | | NIT | 4 | 8 | S | S | Agree |
| | 1e5E.coli with 1e7 Abaum | LVX | 16 | 16 | R | R | Agree |
| | | CIP | 256 | 256 | R | R | Agree |
| | | NIT | 4 | 8 | S | S | Agree |
| E.coli with Corynebacteria | 1e5E.coli with 1e5 Corny | LVX | 16 | 16 | R | R | Agree |
| | | CIP | 256 | 256 | R | R | Agree |
| | | NIT | 8 | 8 | S | S | Agree |
| | 1e5E.coli with 1e6 Corny | LVX | 16 | 16 | R | R | Agree |
| | | CIP | 256 | 256 | R | R | Agree |
| | | NIT | 4 | 8 | S | S | Agree |
| | 1e5E.coli with 1e7 Corny | LVX | 16 | 16 | R | R | Agree |
| | | CIP | 256 | 256 | R | R | Agree |
| | | NIT | 4 | 8 | S | S | Agree |

FIG. 49

| Fold Growth threshold of 4.5 | | | MIC in ug/ml according to | | Resistance profile | | |
|---|---|---|---|---|---|---|---|
| | Bug | ABX | MP | CLSI Compliant BMD | MP | BMD | Agree/Disagree |
| Polymicrobial with Klebsiella | E.coli 2469 control (no Klebsiella) | NIT | 8 | 8 | S | S | Agree |
| | | CFZ | >128 | >128 | R | R | Agree |
| | | CIP | >128 | >128 | R | R | Agree |
| | | TMP/SXT | >128 | >128 | R | R | Agree |
| | | LVX | 16 | 16 | R | R | Agree |
| | E.coli 2469 with 5e3 K. pneumoniae | NIT | 8 | 8 | S | S | Agree |
| | | CFZ | >128 | >128 | R | R | Agree |
| | | CIP | >128 | >128 | R | R | Agree |
| | | TMP/SXT | >128 | >128 | R | R | Agree |
| | | LVX | 16 | 16 | R | R | Agree |
| | E.coli 2469 with 5e4 K. pneumoniae | NIT | 16 | 8 | S | S | Agree |
| | | CFZ | >128 | >128 | R | R | Agree |
| | | CIP | >128 | >128 | R | R | Agree |
| | | TMP/SXT | >128 | >128 | R | R | Agree |
| | | LVX | 16 | 16 | R | R | Agree |
| | E.coli 2469 with 5e5 K. pneumoniae | NIT | 16 | 8 | S | S | Agree |
| | | CFZ | >128 | >128 | R | R | Agree |
| | | CIP | >128 | >128 | R | R | Agree |
| | | TMP/SXT | >128 | >128 | R | R | Agree |
| | | LVX | 16 | 16 | R | R | Agree |
| | E.coli 2469 with 5e6 K. pneumoniae | NIT | 4 | 8 | S | S | Agree |
| | | CFZ | >128 | >128 | R | R | Agree |
| | | CIP | >128 | >128 | R | R | Agree |
| | | TMP/SXT | >128 | >128 | R | R | Agree |
| | | LVX | 16 | 16 | R | R | Agree |
| | E.coli 2469 with 1.5e7 K. pneumoniae | NIT | 8 | 8 | S | S | Agree |
| | | CFZ | >128 | >128 | R | R | Agree |
| | | CIP | >128 | >128 | R | R | Agree |
| | | TMP/SXT | >128 | >128 | R | R | Agree |
| | | LVX | 16 | 16 | R | R | Agree |

FIG. 50

| Bacterial Target | FISH Probes | Labeled | Final Concentration | Sequence | |
|---|---|---|---|---|---|
| E. coli | Eco001 | Alexa647N | 0.8 μM | /5Alex647N/GTATTAACTTTACTCC/3AlexF647N/ | (SEQ ID NO: 143) |
| | Eco002 | Alexa647N | 0.4 μM | /5Alex647N/ACACACACTGATTCA/3AlexF647N/ | (SEQ ID NO: 144) |
| | Eco001 H1 | No label | 3 μM | GGGTAACGTCAATGAGCAAAG | (SEQ ID NO: 145) |
| | Eco0001 H2 | No label | 3 μM | CTTCCTCCCCGCTGAAAGTAC | (SEQ ID NO: 146) |
| | Eco002 H6 | No label | 3 μM | TTTCCAGACGCTTCCACTAAC | (SEQ ID NO: 147) |
| | Eco002 H7 | No label | 3 μM | GGCTCTGGGCTCCTCCCCGT | (SEQ ID NO: 148) |

FIG. 51

| Bacterial Target | FISH Probes | Labeled | Final Concentration | Sequence | |
|---|---|---|---|---|---|
| *E. coli* | Eco001 | Alexa647N | 0.7 μM | /5Alex647N/GTATTAACTTTACTCC/3AlexF647N/ | (SEQ ID NO: 149) |
| | Eco002 | Alexa647N | 0.4 μM | /5Alex647N/ACACACACTGATTCA/3AlexF647N/ | (SEQ ID NO: 150) |
| | Eco001 H1 | No label | 3 μM | GGGTAACGTCAATGAGCAAAG | (SEQ ID NO: 151) |
| | Eco0001 H2 | No label | 3 μM | CTTCCTCCCCGCTGAAAGTAC | (SEQ ID NO: 152) |
| | Eco002 H6 | No label | 3 μM | TTTCCAGACGCTTCCACTAAC | (SEQ ID NO: 153) |
| | Eco002 H7 | No label | 3 μM | GGCTCTGGGCTCCTCCCCGT | (SEQ ID NO: 154) |

FIG. 54

| Urine Sample | Essential Agreement Across 5 Antibiotics* | Categorical Agreement Across 5 Antibiotics* |
|---|---|---|
| Urine A | 100% | 100% |
| Urine B | 100% | 100% |
| Urine C | 100% | 100% |
| Urine D | 100% | 100% |
| Urine E | 100% | 100% |
| Urine F | 100% | 100% |
| Urine G | 100% | 100% |
| Urine H | 100% | 100% |
| Urine I | 100% | 100% |
| Urine J | 100% | 100% |
| Urine K | 100% | 100% |
| Urine L | 100% | 100% |
| Urine M | 100% | 100% |
| Urine N | 100% | 100% |
| Urine O | 100% | 100% |

FIG. 56

| Antibiotics | *LVX* | *CIP* | *CFZ* | *TMP/SXT* | *NIT* |
|---|---|---|---|---|---|
| **CLSI Compliant** | 16 | 128 | >128 | >128 | 8 |
| **Urine A** | 16 | 128 | >128 | >128 | 8 |
| **Urine B** | 16 | >128 | >128 | >128 | 8 |
| **Urine C** | 32 | >128 | >128 | >128 | 4 |
| **Urine D** | 8 | 128 | >128 | >128 | 4 |
| **Urine E** | 16 | 128 | >128 | >128 | 8 |
| **Urine F** | 32 | >128 | >128 | >128 | 8 |
| **Urine G** | 16 | 128 | >128 | >128 | 8 |
| **Urine H** | 16 | >128 | >128 | >128 | 8 |
| **Urine I** | 16 | >128 | >128 | >128 | 8 |
| **Urine J** | 16 | 128 | >128 | >128 | 8 |
| **Urine K** | 8 | 128 | >128 | >128 | 8 |
| **Urine L** | 16 | 128 | >128 | >128 | 8 |
| **Urine M** | 16 | 128 | >128 | >128 | 8 |
| **Urine N** | 8 | 128 | >128 | >128 | 8 |
| **Urine O** | 16 | >128 | >128 | >128 | 8 |

FIG. 57

| Bacterial Target | FISH Probes | Labeled | Final Concentration | Sequence | Comment | |
|---|---|---|---|---|---|---|
| E. coli | P1 Universal Dye 647 | Cy3 | 300 nM | CCGTACTCCCCA/iCy3/GGC | Not specific to E. coli | (SEQ ID NO: 155) |
| | P2 Coli Dye-10 647 | Cy5 | 300 nM | GGT/iCy5/CGACTTA | Not specific to E. coli | (SEQ ID NO: 156) |
| | Helper-1 Coli | No label | 6 µM | 5'ACGCGTTAGCTCCGGAAGCCA | Not specific to E. coli | (SEQ ID NO: 157) |

FIG. 58

| Bacteria | Strain ID | Susceptibility to Ciprofloxacin |
|---|---|---|
| E. coli | ATCC 25922 | Sensitive |
| E. coli | BAA 2469 | Resistant |
| K. pneumoniae | CDC 0076 | Sensitive |
| K. pneumoniae | CDC 0043 | Resistant |
| P. aeruginosa | CDC 0233 | Sensitive |
| P. aeruginosa | CDC 0236 | Resistant |
| E. faecalis | ATCC 29212 | Sensitive |
| E. faecium | ATCC 19434 | Resistant |

FIG. 59

| Bacterial Target | FISH Probes | Labeled | Final Concentration | Sequence | |
|---|---|---|---|---|---|
| E. coli | Eco001 | Alexa647N | 1.2 μM | /5Alex647N/GTATTAACTTTACTCC | (SEQ ID NO: 158) |
| | Eco002 | Alexa647N | 0.6 μM | /5Alex647N/ACACACACTGATTCA/3AlexF647N/ | (SEQ ID NO: 159) |
| | Eco002 H6 | No label | 3 μM | TTTCCAGACGCTTCCACTAAC | (SEQ ID NO: 160) |
| | Eco002 H7 | No label | 3 μM | GGCTCTGGGCTCCTCCCCGT | (SEQ ID NO: 161) |
| | Eco001 H2 | No label | 3 μM | CTTCCTCCCCGCTGAAAGTAC | (SEQ ID NO: 162) |
| | Eco001 H1 | No label | 3 μM | GGGTAACGTCAATGAGCAAAG | (SEQ ID NO: 163) |
| P. aeruginosa | Pae002 2 dye | Alexa647N | 0.4 μM | /5Alex647N/CTTCAAAGATCCTTT/3AlexF647N/ | (SEQ ID NO: 164) |
| | Pae004 2 dye | Alexa647N | 0.5 μM | /5Alex647N/AAATCAATGAAGCTTAA/3AlexF647N/ | (SEQ ID NO: 165) |
| | Pae005_1 2 dye | Alexa647N | 1.1 μM | /5Alex647N/TTCAGGGGAATCAAGTTC/3AlexF647N/ | (SEQ ID NO: 166) |
| | Pae002 H1 | No label | 1.5 μM | CGCGTACGGGGCTATCACCCA | (SEQ ID NO: 167) |
| | Pae002 H2 | No label | 1.5 μM | GCTCCGTCCTACTCGATTTCA | (SEQ ID NO: 168) |
| | Pae004 H1 | No label | 1.5 μM | GGGCTAATCCCCGTTCGCTCG | (SEQ ID NO: 169) |
| | Pae004 H2 | No label | 5 μM | ACTTTCCAGAGCGTTCCGCTA | (SEQ ID NO: 170) |
| | Pae005_1 H2 | No label | 1.5 μM | CCAGTGAGATCTCATCTTGAG | (SEQ ID NO: 171) |
| | Pae005_1 H3 | No label | 3 μM | CGTCGTAGTCTTCGACGGCCC | (SEQ ID NO: 172) |

FIG. 60

| | | | | | |
|---|---|---|---|---|---|
| *K. pneumoniae* | Kpn003_2 | Alexa647N | 0.4 µM | /5Alex647N/CTTCGACTGGTCTCAGC/3AlexF647N/ | (SEQ ID NO: 173) |
| | Kpn001-A | Alexa647N | 1 µM | /5Alex647N/CACCTACACACCAGCG/3AlexF647N/ | (SEQ ID NO: 174) |
| | Kleb001 H1 | No label | 6 µM | TGCCTTCTCCCGAAGTTACGG | (SEQ ID NO: 175) |
| | Kleb23S H3 | No label | 1.5 µM | GCCAGCTGGTATCTTCGACTG | (SEQ ID NO: 176) |
| | Kpn003 H3 | No label | 6 µM | ACAGTTGCAGCCAGCTGGTAT | (SEQ ID NO: 177) |
| *Enterococcus spp.* | Ent001- 2 dye | Alexa647N | 0.8 µM | /5Alex647N/TTGTACTTCCCA/3AlexF647N/ | (SEQ ID NO: 178) |
| | Ent003- 2 dye | Alexa647N | 0.8 µM | /5Alex647N/AACAAAAACAACKGGTAC/3AlexF647N/ | (SEQ ID NO: 179) |
| | Ent004- 2 dye | Alexa647N | 0.8 µM | /5Alex647N/TGCATTCCTTAGC/3AlexF647N/ | (SEQ ID NO: 180) |
| | Ent006- 2 dye | Alexa647N | 0.8 µM | /5Alex647N/CATCATTCTCAATTC/3AlexF647N/ | (SEQ ID NO: 181) |
| | Ent003H1 | No label | 2.85 µM | AGGAATATCAACCTGTTRTCC | (SEQ ID NO: 182) |
| | Ent003H3 | No label | 2.85 µM | GTTTRCGGTACGGGCMGYTGT | (SEQ ID NO: 183) |
| | Ent003H4 | No label | 2.85 µM | TTTCTCACTAGAAGCTTTTCT | (SEQ ID NO: 184) |
| | Ent003H2_1 | No label | 2.85 µM | CTMCTGCGTCCCTCCATTGCTCA | (SEQ ID NO: 185) |
| | Ent004H2fls | No label | 2.85 µM | GGACATGCACTTCCAATCGCA | (SEQ ID NO: 186) |
| | Ent004H2fum | No label | 2.85 µM | TTGGACAGACATTTCCGATCG | (SEQ ID NO: 187) |
| | Ent004H4_2 | No label | 2.85 µM | CAGGAACTTCGSTACTATTAT | (SEQ ID NO: 188) |
| | Ent006H1 | No label | 2.85 µM | GTCCAAACAGTGCTCTACCTC | (SEQ ID NO: 189) |
| | Ent006H2 | No label | 2.85 µM | TCGGTAACCCGAGATGGGCCCCTA | (SEQ ID NO: 190) |
| | Ent006H3 | No label | 2.85 µM | CGAGGCTAGCCCTAAAGCTAT | (SEQ ID NO: 191) |
| | Ent001H1 | No label | 2.85 µM | TTGTAGCACGTGTGTAGCCC | (SEQ ID NO: 192) |
| | Ent001H4 | No label | 2.85 µM | TGAGAGAAGCTTTAAGAGATT | (SEQ ID NO: 193) |

FIG. 61

Labeled Target ↓ / Unlabeled Second Target

| Labeled Target | Sensitive *E. coli* | Resistant *E. coli* | Sensitive *P. aeruginosa* | Resistant *P. aeruginosa* | Sensitive *K. pneumoniae* | Resistant *K. pneumoniae* | Sensitive *Enterococcus* | Resistant *Enterococcus* |
|---|---|---|---|---|---|---|---|---|
| Sensitive *E. coli* | | | 100% | 100% | 100% | 100% | 100% | 100% |
| Resistant *E. coli* | | | 100% | 100% | 100% | 100% | 100% | 100% |
| Sensitive *P. aeruginosa* | 100% | 100% | | | 100% | 100% | 100% | 100% |
| Resistant *P. aeruginosa* | 100% | 100% | | | 100% | 100% | 100% | 100% |
| Sensitive *K. pneumoniae* | 100% | 100% | 100% | 100% | | | 100% | 100% |
| Resistant *K. pneumoniae* | 100% | 100% | 100% | 100% | | | 100% | 100% |
| Sensitive *Enterococcus* | 100% | 100% | 100% | 100% | 100% | 100% | | |
| Resistant *Enterococcus* | 100% | 100% | 100% | 100% | 100% | 100% | | |

FIG. 62

Labeled Target ↓ / Unlabeled Second Target

| Labeled Target | Sensitive *E. coli* | Resistant *E. coli* | Sensitive *P. aeruginosa* | Resistant *P. aeruginosa* | Sensitive *K. pneumoniae* | Resistant *K. pneumoniae* | Sensitive *Enterococcus* | Resistant *Enterococcus* |
|---|---|---|---|---|---|---|---|---|
| Sensitive *E. coli* | | | 100% | 100% | 100% | 100% | 100% | 100% |
| Resistant *E. coli* | | | 100% | 100% | 100% | 100% | 100% | 100% |
| Sensitive *P. aeruginosa* | 100% | 100% | | | 100% | 100% | 100% | 100% |
| Resistant *P. aeruginosa* | 100% | 100% | | | 100% | 100% | 100% | 100% |
| Sensitive *K. pneumoniae* | 100% | 100% | 100% | 100% | | | 100% | 100% |
| Resistant *K. pneumoniae* | 100% | 100% | 100% | 100% | | | 100% | 100% |
| Sensitive *Enterococcus* | 100% | 100% | 100% | 100% | 100% | 100% | | |
| Resistant *Enterococcus* | 100% | 100% | 100% | 100% | 100% | 100% | | |

FIG. 63

| Organisms Spiked into Culture Negative Urine | | Culture Negative Urine | Did probe detect organisms spiked into culture negative urine? | | |
|---|---|---|---|---|---|
| | | | E. coli Probe n=2 | K. pneumoniae Probe n=2 | P. aeruginosa Probe n=2 |
| E. coli | K. pneumoniae | 1 | Y | Y | N |
| | | 2 | Y | Y | N |
| | | 3 | Y | Y | N |
| | | 4 | Y | Y | N |
| | | 5 | Y | Y | N |
| | | 6 | Y | Y | N |
| | | 7 | Y | Y | N |
| | | 8 | Y | Y | N |
| | | 9 | Y | Y | N |
| | | 10 | Y | Y | N |
| E. coli | P. aeruginosa | 1 | Y | N | Y |
| | | 2 | Y | N | Y |
| | | 3 | Y | N | Y |
| | | 4 | Y | N | Y |
| | | 5 | Y | N | Y |
| | | 6 | Y | N | Y |
| | | 7 | Y | N | Y |
| | | 8 | Y | N | Y |
| | | 9 | Y | N | Y |
| | | 10 | Y | N | Y |
| K. pneumoniae | P. aeruginosa | 1 | N | Y | Y |
| | | 2 | N | Y | Y |
| | | 3 | N | Y | Y |
| | | 4 | N | Y | Y |
| | | 5 | N | Y | Y |
| | | 6 | Invalid | | |
| | | 7 | N | Y | Y |
| | | 8 | N | Y | Y |
| | | 9 | N | Y | Y |
| | | 10 | N | Y | Y |

FIG. 67

| Bacterial Target | FISH Probes | Labeled | Final Concentration | Sequence | |
|---|---|---|---|---|---|
| E. coli | Eco469 | Alexa647N | 0.8 μM | /5Alex647N/GTCAATGAGCAAAGG | (SEQ ID NO: 193) |
| | Eco469 H1 | No label | 3 μM | ACTCCCTTCCTCCCCGCTG | (SEQ ID NO: 194) |
| | Eco469 H2 | No label | 3 μM | GGTGCTTCTTCTGCGGGTAA | (SEQ ID NO: 195) |
| P. aeruginosa | Pae002 | Alexa647N | 0.2 μM | /5Alex647N/CTTCAAAGATCCTTT/3AlexF647N/ | (SEQ ID NO: 196) |
| | Pae002 H1 | No label | 1.5 μM | CGCGTACGGGGCTATCACCCA | (SEQ ID NO: 197) |
| | Pae002 H2 | No label | 1.5 μM | GCTCCGTCCTACTCGATTTCA | (SEQ ID NO: 198) |
| | Pae004 H1 | No label | 1.5 μM | GGGCTAATCCCCGTTCGCTCG | (SEQ ID NO: 199) |
| | Pae004 H2 | No label | 5 μM | ACTTTCCAGAGCGTTCCGCTA | (SEQ ID NO: 200) |
| | Pae005 H2 | No label | 1.5 μM | CCAGTGAGATCTCATCTTGAG | (SEQ ID NO: 201) |
| | Pae005 H3 | No label | 5 μM | CGTCGTAGTCTTCGACGGCCC | (SEQ ID NO: 202) |
| K. pneumoniae | Kpn003_2 | Alexa647N | 0.2 μM | /5Alex647N/CTTCGACTGGTCTCAGC/3AlexF647N/ | (SEQ ID NO: 203) |
| | Kleb001 H1 | No label | 6 μM | TGCCTTCTCCCGAAGTTACGG | (SEQ ID NO: 204) |
| | Kleb235 H3 | No label | 1.5 μM | GCCAGCTGGTATCTTCGACTG | (SEQ ID NO: 205) |
| | Kpn003 H3 | No label | 6 μM | ACAGTTGCAGCCAGCTGGTAT | (SEQ ID NO: 206) |

FIG. 68

MICROBIAL ANALYSIS WITHOUT CELL PURIFICATION

GOVERNMENT SUPPORT

This invention was made with government support under grant numbers R43 AI080016, R01 AI117058, and R44 AI080016 awarded by the National Institutes of Health as well as contract number HHSO100201500022C awarded by the Biomedical Advanced Research and Development Authority. The government has certain rights in the invention.

TECHNICAL FIELD

The disclosure relates to the detection of infections, identification of the infectious microbial pathogens, and determination of effective antimicrobial treatments for the infections.

BACKGROUND

The epidemic of life-threatening infections caused by antibiotic-resistant bacteria is fueling a global healthcare crisis. The problem is driven, in part, by the fact that current diagnostic methods require days to determine the optimal antimicrobial treatments to treat an infection. The delay caused by slow testing leads to suboptimal treatment, poor outcomes, and overuse of powerful broad-spectrum antibiotics that cause the spread of antibiotic resistance. The mortality due to infections caused by resistant bacteria is increasing precipitously. A 2014 report by the Review on Antimicrobial Resistance estimates that by the year 2050, antimicrobial resistance will be responsible for more than 10 million fatalities per year.

Early treatment with an optimally effective antibiotic targeted for the particular pathogen causing the infection can dramatically improve the medical outcomes including preventing death. Unfortunately, current methods to identify the effective targeted antibiotics, called antimicrobial susceptibility testing (AST) methods, require days to deliver results. One reason that current antimicrobial susceptibility testing takes so long is that the tests require a large number—on the order of millions—of purified pathogen cells. It requires a day or more using the more than 130-year-old colony purification method that is used to purify this number of cells by culturing in petri dishes. Once the purified cells are available it generally takes one or more days to identify the pathogens and determine which antibiotics will be effective for treating the patient.

In the meantime, patients are treated "empirically" with broad-spectrum antibiotics that kill a broad range of pathogens that might be causing the infection. Although these drugs can treat a broad range of pathogens, they are generally not the optimal therapy for a patient's particular pathogen but can also completely fail to effectively treat the infection. Empiric use of broad-spectrum antibiotics also causes the spread of antibiotic resistance. These broad-acting drugs cause resistance not only in the disease-causing pathogens but also in the trillions of benign microbes that populate the human body. Further exacerbating the spread of antibiotic resistance is the fact that, in the absence of rapid diagnostics to determine which patients actually have an infection, uninfected patients are frequently treated unnecessarily with the resistance-causing antibiotics.

Determining which antimicrobial treatments will be effective much sooner than possible using current methods not only can improve medical outcomes but it can lower the cost of healthcare. For example, common life-threatening hospital acquired infections, such as surgical site infections and ventilator-acquired pneumonia, are responsible for nearly $10B of healthcare costs in the U.S. Length of stay in the hospital largest cost attributable to these infections. Getting patients on the optimal antimicrobial therapy closer to the onset of symptoms can significantly accelerate patient recovery and reduce lengthy and costly hospitalizations.

In summary, current methods require days to determine if a patient has an infection, and if so which antimicrobial agents that are most likely to be effective. In large part, the delay is caused by the time-consuming cell purification steps the methods require. In the absence of timely diagnostic information when patients present with symptoms, they are treated empirically with broad-spectrum antibiotics, which may be sub-optimal and cause the spread of resistance. Because the antibiotics are prescribed before diagnostics results are available, even uninfected patients are unnecessarily treated and acquire resistance.

SUMMARY

The invention addresses the need for diagnostic tests that detect infections and determine the effective antimicrobial treatment much more rapidly than current methods. The invention eliminates the time-consuming steps needed by today's methods for generating large numbers of purified cells. The inventive methods can detect infections, identify the infectious pathogens, and the effective antimicrobial agents in several hours rather than the days required by current methods. By detecting infections and identifying effective targeted antimicrobial agents much closer to the onset of symptoms, the invention has the potential to dramatically improve medical outcomes and minimize empiric treatment with resistance-causing broad-spectrum antibiotics.

Treating patients near the onset of symptoms with effective antibiotics dramatically improves medical outcomes, saving both lives and healthcare costs. The systems and methods of the invention make it possible to deliver antimicrobial susceptibility testing results in several hours as compared to the days required by current methods. Administering an effective antibiotic days earlier can improve medical outcomes and help attenuate the overuse of empirically prescribed broad-spectrum antibiotics which causes the spread of resistance.

Conventional methods for determining effective treatment, called antimicrobial susceptibility testing methods, require days to deliver results, in part because these methods require millions purified pathogen cells. The process for generating these purified cells uses a time-consuming colony purification method for culturing the disease-causing pathogen cells on petri dishes. Colony purification typically takes one or more days to complete. After colony purification, another day or more is generally required to identify the pathogen species and for antimicrobial susceptibility testing to determine which antimicrobial agents should be used to treat the patient.

The invention provides methods for identifying pathogens or determining antimicrobial susceptibility from specimens without colony or cell purification. The significant improvement in time to results for the inventive methods compared to current methods come from the invention's ability to analyze patient specimens directly without requiring time-consuming steps for preparing of large numbers of purified pathogen cells.

Antimicrobial susceptibility testing can be viewed as a stepwise process. The goal is to determine which members of a panel of antimicrobial agents are effective for the particular pathogen strain that is causing a patient's infection. Typically, when an infection is detected, the species of pathogen is first identified. Identifying the species of the pathogen is useful for choosing the antimicrobials and dosing that can generally be used for treating that species. However, since the particular pathogen strain causing the infection may have become resistant to any of the antimicrobials, antimicrobial susceptibility testing must be done to determine to which of the potential treatments the pathogen is actually susceptible.

After species identification the pathogen cells from the patient's specimen are apportioned, or aliquoted, into a series of liquid solutions containing nutrient growth medium various antimicrobials at various concentrations. Then, the aliquots are allowed to incubate at a temperature conducive to microbial replication (generally 35-37 degrees C.). If the pathogen is susceptible to the antimicrobial it can replicate normally, that is, the number of pathogen cells increase as they do in microbiological growth medium the absence of antimicrobials. If the pathogen is susceptible to the antimicrobial, it fails to replicate, replicates to a much lesser extent, or shows morphological or other abnormalities, indicative of effectiveness of the antimicrobial agent. Finally, the replication of pathogen cells is assessed in the various aliquots to determine which antimicrobial agents are effective. We refer to the set of a pathogen's antimicrobial susceptibility/resistance results for a for a series of antimicrobials as its antimicrobial susceptibility profile.

Both conventional methods and the inventive method for antimicrobial susceptibility testing follow the steps above, but the inventive method determines a pathogen's antimicrobial susceptibility profile in several hours while conventional methods require several days. The rapid antimicrobial susceptibility testing results using the inventive method arise from the new method's ability to test patient specimens directly without time-consuming culture-based pre-enrichment growth to achieve high concentrations of pure cells. This enrichment and purification is most commonly done using colony purification on petri dishes.

For conventional methods, the cells recovered after colony purification are first identified using biochemical, microbiological, nucleic acid methods, or Matrix-Assisted Laser Desorption/Ionization-Time Of Flight (MALDI-TOF) mass spectrometry (MS). Once the identity of the pathogen species is known, appropriate antimicrobials and concentrations can be chosen that are appropriate for determining the antimicrobial susceptibility profile for pathogens of that species.

Several novel aspects of the inventive systems and methods enable its ability to rapidly deliver antimicrobial susceptibility results directly from patient specimens.

Firstly, patient specimens generally contain orders of magnitude fewer cells than are required for traditional antimicrobial susceptibility testing. The inventive methods, in contrast to current culture-pre-enrichment dependent methods, can enumerate small numbers of pathogen cells by sensitive single cell counting using non-magnified digital imaging. Furthermore, because the method enumerates small numbers of individual cells, it can very quickly—in only a few bacterial generations—determine whether the cells have increased in number in an aliquot containing an antimicrobial and growth medium.

Secondly, patient specimens contain sample matrix and commensal microbes unrelated to the infectious pathogens. Guidelines for conventional methods such as those from the Clinical Laboratories Standards Institute (CLSI) or the European Committee on Antimicrobial Susceptibility Testing (ECAST) require purified culture cells resulting from clonal growth of colonies on agar-based growth media in petri dishes. These cells contain only a single microbial species and no sample matrix.

As discussed above, the identity of the pathogen species must be known in order to interpret antimicrobial susceptibility testing results correctly for arriving at effective clinical treatment options. This is a key reason underlying why conventional and most emerging antimicrobial susceptibility testing methods require a pure culture of cells.

To determine the antimicrobial susceptibility profile, as described above, the conventional and most emerging methods assess the impact of different antimicrobials at different concentrations on the growth of the target pathogen. The reason why these methods require a pure population of identified cells to interpret the antimicrobial susceptibility testing results is that these methods use non-specific methods, for example light-scattering or microscopy, for assessing growth in the antimicrobial-containing aliquots. Consider the case if there were more than one species present, for example a pathogen and species of normal microbes that are part of the human microbiome—which is the case in most primary patient specimens. If growth were observed in an antimicrobial-containing aliquot, it would be impossible to tell, using a general method for detecting growth, whether the disease-causing pathogen or one or more of the commensal species was resistant and capable of growing.

In contrast, to conventional methods and others that require purified pathogen cells because they use non-specific methods for detecting whether the pathogen grows in the presence of antimicrobials, the inventive methods use pathogen-specific detection to assess growth of the pathogen in the presence of various antimicrobials. Because only the disease-causing pathogen cells are enumerated after the incubation step (any commensal microbes are not enumerated) the inventive method can be used to determine antimicrobial susceptibility directly in the non-sterile primary specimen containing one or many commensal microbial species.

Systems and methods of the invention for pathogen identification can be used to determine whether a specimen contains cells of pathogen species in sufficient numbers to be suspected of causing an infection.

Systems and methods of the invention for antimicrobial susceptibility testing can be used to determine which of one or more antimicrobial agents can prevent normal cellular replication of a pathogen that is suspected of causing an infection in a patient specimen. Such antimicrobial agents can potentially be used to effectively treat a patient's infection.

In a preferred embodiment of the inventive method for antimicrobial susceptibility testing, a specimen is into separate portions containing nutrient growth medium to promote microbiological cell replication or growth. One or more of said portions may be used as a reference or baseline portion which is directly processed and analyzed by the inventive method before incubation at a temperature that promotes growth to determine the number and quality of pathogen cells.

One or more of said portions may be incubated at a temperature that promotes growth of the pathogen cells to ascertain if the pathogen cells are viable. Other of said portions each contain, in addition, one or more antimicrobial agents at particular concentrations, are incubated to determine the impact of the antimicrobial agents on pathogen cellular replication.

The inventive systems and methods are then used to analyze pathogen cell number and quality in the incubated portions and to compare these results to the number and quality of the pathogen cells in the un-incubated reference portion. If the pathogen cells are significantly impaired in their ability to replicate normally in a portion containing a particular antimicrobial agent, the pathogen is scored as susceptible to the antimicrobial agent at the concentration in that portion by the analysis software. Alternatively, if normal growth in not impaired significantly in the portion, the pathogen scored as not susceptible to the antimicrobial agent at the concentration in that portion by the analysis software.

The inventive systems and methods include assessment criteria by which cellular replication is assessed for determination of a pathogen or microbial target's antimicrobial susceptibility or resistance in a portion containing antimicrobial agent(s). These criteria may be determined for specific combinations of parameters including but not limited to the species of the target microbe, specimen type, antimicrobial agents, growth medium composition, temperature, and incubation time.

The assessment criteria are preferably determined empirically by correlation with an accepted reference method for antimicrobial susceptibility testing. One standard reference method is broth microdilution (BMD), a method described fully elsewhere (See Patel, 2015, M07-A10, CLSI 35(2), incorporated by reference) and understood by those familiar with the art. Broth microdilution is a method by which the antimicrobial susceptibility of a microbial strain to an antimicrobial agent is assessed under standard conditions. Purified cells of the target microbe are added at a defined concentration to a series of portions or aliquots of a defined nutrient growth medium containing serial 2-fold dilutions of various antimicrobial agents. The antimicrobial susceptibility of the microbial strain is determined after visually assessing the turbidity of the various portions after a defined period of growth incubation. The lowest concentration of an antimicrobial agent in which turbidity is visually absent or significantly lowered compared to a portion containing no antimicrobial agent is called the minimum inhibitory concentration (MIC). Organizations that determine standards for antimicrobial susceptibility testing (for example, CLSI or EUCAST) have correlated MIC values for combinations of particular microbial species and particular antimicrobial agents with the efficacy of particular therapeutic doses of the antimicrobial agent in clinical practice. The MIC values are generally binned into categorical ranges: Susceptible, Intermediate Resistant, and Resistant. These are called SIR or categorical antimicrobial susceptibility testing results In this way, the MIC for a of a particular strain of a particular species for a particular antimicrobial agent can be reported as an SIR or categorical result. Other standard methods used for determining include the -Bauer or disk-diffusion and agar-dilution. These methods are described in CLSI and EUCAST documents and known to those familiar with the art.

Assessment criteria for determining antimicrobial susceptibility testing results using the inventive methods and systems are determined empirically by using the invention to assess the degree and quality of cellular replication of various strains of a particular species in various concentrations of a particular antimicrobial agent, similar to the broth microdilution method. Criteria for assigning an antimicrobial susceptibility testing result (generally, an MIC or a SIR categorical result) to a strain of a particular species for a particular antimicrobial agent are chosen such that the results for the various strains, using the invention, correlate consistently with the results of the reference broth microdilution method. For example, a criterion that can be used by the inventive systems and methods for determining antimicrobial susceptibility testing results is assessment of the fold-growth (the fold-increase in number of target cells) of target microbes of a certain species over a certain period of incubation in the presence of various concentrations of a certain antimicrobial agent in nutrient growth medium at a certain temperature. In this case the empirical studies to determine effective criteria to use for the inventive systems and methods to assess the antimicrobial susceptibility would assess the fold-growth of various strains of the species in various concentrations of the antimicrobial agent. A threshold value for fold-growth can be chosen such that if the fold-growth measured for a strain using the invention correlates with the results of the broth microdilution for the same strain grown in the presence of the same antimicrobial agent. The threshold is chosen empirically using various strains of the target species such that if the fold-growth of the strain exceeds the threshold, the strain is categorized by the invention as having grown significantly in the presence of the antimicrobial agent at that concentration. If the fold-growth of the strain is less than the fold-growth threshold, the strain is categorized by the invention as not having grown significantly. Thus, the threshold value for fold-growth, in this example, is chosen such that the both the reference broth microdilution method and the inventive method return the same result as to whether or not the various strains are determined to have grown significantly or not in the various antimicrobial agent concentrations.

Other assessment criteria can also be used by the systems and methods of the invention to determine antimicrobial susceptibility testing results. For example, assessment of morphological characteristics reflecting perturbation of normal cellular replication caused by incubation in an antimicrobial agent. As another example, the degree of growth inhibition, in a portion containing an antimicrobial agent, compared to a portion containing no antibiotic after the incubation step can be assessed. Multiple assessment criteria can also be used in concert to determine whether or not an antimicrobial agent at a particular concentration causes a significant perturbation to normal cellular replication of target cells.

Thus, the inventive methods can detect infections, identify the infectious pathogens, and determine which antimicrobials will be effective for treatment directly from patient specimens.

Patient specimens such as urine, stool, respiratory, wound, cerebral spinal fluid, or blood are preferably transferred directly into an analytical cartridge for microbial analysis without any specimen preparation by the user. Thus, there is preferably no requirement for users to carry out colony purification to isolate large numbers of pure pathogen cells, nucleic acid purification, or other time- or labor-intensive specimen preparation protocols. Specimens are preferably loaded directly into test cartridges without any pre-enrichment or cleanup to, for example, remove biological detritus. The cartridge contains reagents for the microbial quantification and identification and the antimicrobial susceptibility tests of the disclosure. Steps such as species-specific labelling and imaging of microbes in the specimen all occur on the cartridge into which the specimen has been directly loaded. The cartridges include target cell-specific labels such as fluorescent probes that are used to identify microbes in the specimen by the systems and methods of the invention. To identify microbes, the analyzer preferably includes an imaging subsystem to image labelled microbes in the cartridge.

Rapidly detecting infections, identifying pathogens, and determining antimicrobial susceptibility using the systems and methods of the invention offer the potential for delivering actionable results for guiding effective treatment of patient infections much more quickly than convention methods requiring lengthy culture steps. Systems and methods of the invention can provide clinicians with the ability to detect infections and identify the infectious pathogens in about 30 minutes, and determine antimicrobial susceptibility testing results in several hours by simply transferring a patient specimen directly into an analytical cartridge and loading the cartridge into an instrument.

Embodiments of the invention include microbe detection and identification of effective treatment directly from patient specimens.

In certain aspects, the disclosure provides a method for antimicrobial susceptibility testing. The method includes: obtaining a polymicrobial specimen; dividing the specimen into wells wherein at least some of the wells include different agents or concentrations of one or more agents; incubating the specimen in the wells to allow differential growth in response to the different agents or concentrations of agents; and counting individual cells of a specific species in each well to identify an agent or concentration of an agent that inhibit growth of the specific species. The method may include counting cells in a control well containing no antimicrobial agent (e.g., after incubation of the control well for a defined period between 1-12 hours at a defined temperature between 30 and 40 degrees C.). The method may include comparing a number of cells counted in each well to a count from the control well to determine viability of the microbes when exposed to the different agents or concentrations of agents. The incubating step may include fluorescently labeling the microbes in a species-specific manner, and the counting step may include imaging each well and counting fluorescent spots in an image. The labeling may use a target-specific fluorophore-labeled nucleic acid or nucleic acid analog probe and the counting may rely on fluorescent in situ hybridization. Preferably the steps do not include nucleic acid amplification. The incubating step may last less than about an hour and may be performed at a temperature lower than about 40 degrees C. in a growth medium.

In certain embodiments, the dividing, incubating, and counting steps are performed using a cartridge that includes the wells. The method may include transferring a portion of the specimen into the cartridge and loading the cartridge into an analyzer. The cartridge may include microbe-binding magnetic beads and the analyzer may use a magnet to separate the microbes from other parts of the specimen and uses an imaging subsystem to perform the counting step. In some embodiments, the analyzer uses a pneumatic subsystem to perform the dividing step within the cartridge—the wells are within the cartridge and are preloaded with the different agents or concentrations of agents—and, after the dividing and the incubating steps, the analyzer transfers contents of the wells to corresponding reagent wells to therein expose the incubated specimen to the microbe-binding magnetic beads and to species-specific detectable labels. The analyzer may use a magnet to pull the microbe-binding magnetic beads and the bound, individual microbes to detection surfaces within the cartridge.

In some embodiments, the magnet pulls the microbe-binding magnetic beads through a dye cushion that excludes unbound detectable labels from the detection surface. The analyzer may use a carousel and/or a mechanical cartridge conveyance to transfer the cartridge to an imaging subsystem to perform the counting step. In some embodiments, the species-specific detectable labels include fluorescent nucleic acid probes that hybridize to target nucleic acids of specific species of microbes. The incubating and counting steps may accomplish fluorescent in situ hybridization (FISH) analysis substantially at physiological temperature within the analyzer.

Identifying the antimicrobial agent that inhibits growth of the microbe may involve comparing the number of complexes in the incubated specimen to the number of complexes in an un-incubated specimen. The analyzer may use the cartridge to perform species-specific counting of the individual microbes after the differential growth.

In certain embodiments, the wells are within a cartridge, and the method includes transferring some of the specimen into the cartridge, and loading the cartridge into the analyzer. The analyzer manipulates the cartridge to perform the dividing, incubating, and counting steps. The specimen does not require any chemical or molecular sample preparation techniques by a user before the transferring step. The transferring step may be done by pipetting some of the specimen from a collection vessel into a sample well on the cartridge In some aspects, the disclosure provides a microbial analysis method. The method includes: obtaining a specimen comprising microbes; transferring, without any colony or cell purification or culturing steps, a portion of the specimen into a well, the well comprising species-specific detectable labels and microbe-binding magnetic beads; collecting, using a magnet, the beads on an imaging surface; and imaging the detectable labels on the imaging surface to thereby determine the presence of cells of the species in the portion of the specimen. The specimen does not require any chemical or molecular sample preparation techniques by a user before the transferring step. The method may further include labelling target microbes with the species specific detectable labels in the well and binding microbes to the microbe-binding magnetic beads, wherein the observing step comprises imaging—without washing away unbound detectable label—labeled, magnet-bound cells. The method may further include counting individual ones of the labeled, magnet-bound cells.

In certain embodiments, the well is provided within a cartridge and the collecting and imaging steps occur while the beads and the cells are within the cartridge. The method may include loading the cartridge into an analyzer that performs the collecting and imaging steps. The analyzer may include a plurality of subsystems that include at least an imaging subsystem to image the labelled microbe and a carousel operable to transport test cartridges between subsystems.

The transferring step may include transferring the specimen into a receiving well of the cartridge, after which the analyzer may divide the specimen into a plurality of division wells within the cartridge (the well is one of the division wells). The species-specific detectable labels may include a fluorescently-labelled oligonucleotide probe that specifically hybridizes to nucleic acid of the cells of the species. The imaging step may include fluorescent in situ hybridization (FISH) analysis at constant physiological temperature within the cartridge.

In some embodiments, collecting the beads on the imaging surface includes magnetically pulling the beads through a dye cushion in the well while the dye cushion excludes unbound detectable labels from the imaging surface. Preferably, the cells of the species are determined to be present in the specimen within about 30 minutes of the transferring step.

In certain aspects, the invention provides for identifying a microorganism. Microbial identification is accomplished directly from patient specimens, such as whole blood, plasma, serum, urine, sputum, saliva, stool, cerebrospinal fluid, amniotic fluid, peritoneal fluid, pus, lymph, vaginal secretions, nasal secretions, vomit, sweat, and tissue with no specimen preparation steps. For example, the method may involve transferring a urine specimen directly into an analytical cartridge device for microbe identification. In some embodiments, the method includes transferring a patient specimen directly into a sample well of an analytical cartridge and operating the cartridge to label a microbe in species-specific manner, image the labelled microbe and identify the labelled microbe. Labelling microbes includes exposing the specimen to species-specific labels. The labels may comprise target-specific magnetic tags and detectable labels. The detectable labels may comprise species-specific fluorescent probes. The probe may be complimentary only to nucleic acid of the species of microbe. When exposed to a specific species of microbe, the probe hybridizes only to that species allowing for detection of the species of microbe. As such, multiple species of microbes in a specimen can be identified and susceptibility to different antimicrobials or other treatments can be tested in a single analytical cartridge. In some embodiments, operating the cartridge may include loading the cartridge into an instrument to identify a microbe in the patient specimen within the cartridge. The invention provides analytical cartridges and instruments capable of directly receiving and processing a patient specimen to identify microbes and/or to determine therapeutic susceptibility and efficacy all within the cartridge.

Systems and methods of the invention include instruments or analyzers that can be used to interact with analytical cartridges to carry out methods of the invention. The instrument may include a plurality of subsystems to perform methods of the invention. The analytical cartridge may be loaded into the instrument having a plurality of subsystems to process the specimen within the cartridge. In a preferred embodiment, one of the plurality of subsystems may be an imaging subsystem to image a labelled microbe within the cartridge. Subsystems of the instrument may also include a pneumatic subsystem, a magnetic subsystem, and a waste subsystem. The instrument may also include a carousel, a mechanical cartridge conveyance and a task scheduler to move and manipulate the cartridge within the instrument. The instrument is capable of performing all of the processing steps at a constant temperature.

Systems and methods of the invention, including instruments and devices, can perform a broad range of diagnostic functions including detecting infections; detecting, identifying, and quantifying pathogen cells of all types; determining antimicrobial susceptibility; detecting and quantifying toxins, viruses, and biomarkers including host-response factors; and detecting and quantifying diagnostically informative human or host cells. The systems and methods of the invention are capable of simultaneously performing such diagnostic functions alone or in combination on a single specimen in a in a single device (e.g., an analytical cartridge). The systems and methods of the invention include the capability of random access processing, such that multiple such devices performing different types diagnostic tests (e.g., for urinary tract infections, blood infections, and respiratory infections) can be simultaneously processed on a single instrument. As such, the instruments and cartridges described herein provide such functionality and can be manipulated to process the specimens within a device accordingly.

Methods and systems of the invention can include transporting analytical cartridges to the plurality of subsystems of the instrument via a carousel within an instrument. In some embodiments of the invention, a mechanical conveyance mechanism within the instrument transfers each of the analytical cartridges between the carousel and various subsystems of the instrument. The mechanical cartridge conveyance applies a pushing force to transfer cartridges onto and off of the carousel. In some embodiments, the instrument includes a task scheduler for managing the transport and transfer of each of the analytical cartridges amongst the plurality of subsystems.

In some embodiments, managing the movement of each of the analytical cartridges within the instrument, including the time each cartridge spends in a subsystem may be performed by a task scheduler within the instrument. The method may include reserving time on various subsystems as needed for each of the cartridges. The method may also include operating the mechanical cartridge conveyance to transfer the cartridge from one of the subsystems to the carrousel and to rotate the carousel to position the cartridge adjacent another one of the subsystems. In some embodiments of the invention, a task scheduler may manage the movement of an analytical cartridge (i.e., the steps/parameters of the analysis to be performed) by identifying the contents of the cartridge. The contents of a cartridge and the required processing may be associated with a tag on the cartridge. In some embodiments of the invention, each of the analytical cartridges include a tag readable by the instrument. The instrument may read the tag via a barcode analyzer and associate the tag with a particular set of instructions for the task scheduler to execute. The tag may be a barcode and may be specific/unique to the specimen in the instrument.

Systems and methods of the invention include pneumatically distributing the specimen within the cartridge. In some embodiments, methods include distributing the specimen from a sample well to a plurality of wells within the cartridge. The method further involves controlling the distribution of the specimen by operation of a plurality of valves within the cartridge. In certain embodiments of the invention, methods include transporting the cartridge to a pneumatic subsystem of the instrument and operating the subsystem to distribute the specimen from the sample well to a plurality of wells within the cartridge.

Systems and methods of the invention are used to label microbes. Methods of labelling microbes include loading specimens directly into analytical cartridges containing reagents specific for processing specimens according to methods of the invention. The reagents may include, for example, species-specific labels, growth medium, antimicrobial agents, and dyes. The reagents may be in liquid form, or, preferably lyophilized and may be loaded in certain of the wells within the analytical cartridge (e.g., testing device). The reagents may be specific for a test, as such, the cartridge may be test specific. Methods of the invention include labelling a microbe by exposing a specimen to species-specific magnetic tags and detectable labels preloaded within the cartridge. The specimen may be exposed to the magnetic tags and detectable labels within the wells of the cartridge by pneumatic distribution. Detectable labels may include fluorescent oligonucleotide or antibody probes, specific and nonspecific ligands, lectins, stains, and dyes that bind targets. In certain embodiments, magnetic tags are used in combination with the detectable labels to bind to target microbes before magnetically selecting and imaging the target microbes. In some embodiments, the detectable labels may be fluorescent probes that specifically hybridize to nucleic acid of a species of microbe. In preferred embodiments, the detectable label is a fluorescently rRNA-targeted fluorescently-oligonucleotide probe that hybridizes to a specific species of microbe. In certain embodiments, methods of labelling and imaging include fluorescent in situ hybridization (FISH) for labeling cellular targets and magnetic selection of labeled cellular targets to deposit the labeled targets on an detection surface for imaging and analysis. In certain embodiments the labeling and magnetic selection steps occur at a constant temperature. In some preferred embodiments, these steps are all performed at temperatures between about 36 and 39 degrees Celsius.

In certain embodiments of the invention, methods include transporting the cartridge to a magnetic subsystem of the instrument and operating the magnetic subsystem to draw the labelled microbe to a detection surface within the cartridge through an opaque, dense, aqueous dye-cushion layer. The dye-cushion layer can be designed to optically sequester the unbound fluorescent label and the specimen matrix from the detection surface. This can eliminate the need for wash steps to remove fluorescent label that has not been bound to target cells, increase signal to noise, and minimize or eliminate the need for sample preparation steps. The method includes drawing the labelled microbe through the dye-cushion layer prior to reaching the detection surface.

Systems and methods of the invention provide imaging analysis of specimens. Specimens are directly processed and imaged within the cartridge to determine the identity of the microbes present the specimen. Particularly, the detection surface of the cartridge is imaged and imaging analysis identifies microbes in the specimen. Methods of identifying microbes may also include quantifying the microbes. In certain embodiments of the invention, methods include transporting the cartridge to an imaging subsystem of the instrument by operating the carousel and operating the subsystem to image and analyze the detection surface of the cartridge. Digital, non-magnified techniques can be used to identify and quantify microbes.

Specimens may also be incubated in the presence of antimicrobial agents or other treatments of various types and at various concentrations before imaging. The incubation can occur in the same analytical cartridge or in different analytical cartridges. Regardless, specimens processed as described herein can be processed at constant a temperature, including incubation steps described herein. The constant temperature may be physiological temperature of a mammal. Physiological temperature may be a temperature below 40 degrees Celsius. In a preferred embodiment, the temperature is between 36 and 39 degrees Celsius.

Systems and methods of the invention can be used to identify microbes and to test for antimicrobial susceptibility of a microbe in a specimen. Methods of the invention may be performed in separate analytical cartridges or within the same cartridge. In a preferred embodiment of the invention, analytical cartridges directly receive a specimen and internally divide a specimen into separate portions, where one or more of the portions may be exposed to one or more species-specific detectable labels. The portions are processed and imaged to identify microbes in each of the portions. In certain embodiments, identification and antimicrobial susceptibility testing can be performed one the same specimen in the same device.

Methods of the invention include antimicrobial susceptibility testing of a polymicrobial specimen. Methods include, distributing a polymicrobial specimen from a subject into multiple partitions. One or more of the partitions may contain different antimicrobial agents and may be incubated in the presence of the different antimicrobial agents to determine differential growth in the incubated portions. One or more of the partitions may not be exposed to antimicrobial agents, so as to provide a baseline for determining changes in the other partitions. The partitions may also be incubated in the presence of growth medium. The partitions are exposed to species-specific detectable labels. The partitions are imaged to identify and quantify the microbes in each of the partitions. Analyzing the number of microbes in each of the partitions identifies the effectiveness of each antimicrobial agent in reducing, or even preventing, growth of a pathogenic agent. By counting and comparing the number of microbes in each of the partitions, the effectiveness of a treatment is determined. In some embodiments, methods include comparing the number of microbes in incubated partitions to the number of microbes in a baseline partition. In certain aspects, the method of antimicrobial susceptibility testing may be performed by depositing the specimen directly into the analytical cartridge. The analytical cartridge divides the specimen into multiple partitions within the cartridge to perform antimicrobial susceptibility testing. Methods of antimicrobial susceptibility testing are performed within hours of introducing the cartridge into the instrument and preferably within about 4 hours.

In certain aspects, the invention provides systems for identifying and determining antimicrobial susceptibility of a microbe in a specimen. Preferred systems include analytical cartridges and operable to receive a patient specimen and an instrument operable to receive analytical cartridges. In certain embodiments, analytical cartridges for identification, antimicrobial susceptibility testing are provided preloaded with reagents, such as species-specific labels, antimicrobial agents and growth medium specific to various microbes. In some embodiments, the analytical cartridges contain a plurality of wells (or partitions) within the cartridge. The plurality of wells within the cartridge may include at least a sample well, distribution wells, and imaging wells. In some embodiments, systems of the invention distribute a specimen from the sample well to a plurality of wells within the cartridge. In certain aspects, the specimen is distributed from the sample well to a plurality of distribution wells preloaded with antimicrobial agents and growth media for incubation. Incubated specimens may then be transferred from a distribution well to a reagent well to expose the incubated specimen to species-specific labels to form a complex.

Users may select an appropriate application-specific cartridge and directly transfer a patient specimen therein to perform specific diagnostic test and analysis. The cartridge may be loaded into an instrument to process the specimen according to the applicable analysis. The instrument may identify the required processing steps by scanning a tag, such as a barcode, on the cartridge, where the tag is specific to the analysis to be performed.

Results obtained using systems and methods of the invention may be used to inform treatment decisions. Methods may include administering a treatment to a patient identified as effective in reducing growth or viability of the microbe identified as a pathogenic agent.

BRIEF DESCRIPTION OF THE DRAWINGS

FIG. 17 is a table of Probe sequences used in this example.

FIG. 21 is a table giving Probe sequences used in this example.

FIG. 22 is a table showing challenge bacteria to test the specificity of detecting *E. coli*

FIG. 23 is a table showing Probe sequences used in this example.

FIG. 27 is a table of Probe sequences used in this example 4.

FIG. 32 is a table of Probe sequences used in this example 6.

FIG. 35 is a table of AST results for all bacteria and antibiotics tested in this example.

FIG. 36 is a table of Probe sequences used in this example 7.

FIG. 39 is a table of Oligonucleotides used in this example 8.

FIG. 42 is a Summary of the overall essential and categorical agreement for all organisms, antibiotics and inoculum levels.

FIG. 45 is a table of Probe sequences used in this example 9.

FIG. 48 shows agreement of *E. coli* with varying inoculum levels of off-target microbe (*S. aureus, Staphylococcus epidermidis*, and, *Citrobacter freundii*) standard BMD.

FIG. 49 shows agreement of *E. coli* with varying inoculum levels of off-target microbe (*Micrococcus luteus, Acinetobacter baumannii, Corynebacterium minutissimum*) standard BMD.

FIG. 50 shows agreement of *E. coli* with varying inoculum levels of off-target microbe (*K. pneumoniae*) standard BMD.

FIG. 51 is a table of Probe sequences used in this example 10.

FIG. 54 is a table of probe sequences used in this example 11.

FIG. 56 shows 100% essential agreement and 100% categorical agreement for each of the 15 spiked culture negative clinical UTI urine samples to standard BMD. *Cefazolin, Ciprofloxacin, Levofloxacin, Nitrofurantoin, and Trimethoprim-Sulfamethoxazole.

FIG. 57 shows the MIC for 15 urine samples spiked with *E. coli* as determined by the novel AST method compared to the standard BMD method ("CLSI Compliant"). Concentrations in μg/ml.

FIG. 58 is a table of probe sequences used in this example 12.

FIG. 59 shows Ciprofloxacin-sensitive and resistant strains used in this example FIG. 60 is a first half of a Table of probe sequences used in this example 13.

FIG. 61 is a second half of a Table of probe sequences used in this example 13.

FIG. 62 shows essential agreement for a polymicrobial infection with 2 target organisms. As seen below, the AST method described above yields 100% essential agreement to standard BMD FIG. 63 shows categorical agreement for a polymicrobial infection with 2 target organisms. As seen below the AST method described above yields 100% categorical agreement to standard BMD.

FIG. 67 is a table "Table A of Example 14", showing target pathogens were detected while other non-target pathogens were not.

FIG. 68 is a table, "Table B of Example 14", showing probe sequences used in this example 14.

DETAILED DESCRIPTION

The invention provides systems and methods for rapid automated analysis of microbes without specimen preparation. Systems and methods of the invention provide for microbial identification and for antimicrobial susceptibility testing (AST) directly from patient specimens. Microbes in specimens can be analyzed for differential growth in the presence of various antimicrobial agents. Specimen manipulation, incubation, processing, and analysis steps are all performed within a single analytical cartridge. Identification analyses can be completed in under about thirty minutes and antimicrobial susceptibility testing may be completed in under about four and a half hours. Systems and methods of the invention identify targets, such as microbes, using species-specific labels and non-magnified digital imaging and image analysis to accurately and quickly identify and quantify targets in a specimen. Systems and methods of the invention preferably enable microbe identification and antimicrobial susceptibility testing analysis on specimens that have not been processed to purify target pathogen cells and preferably without requiring manual specimen preparation by the user. Minimizing the need for user interaction with a specimen, systems and methods of the invention provide microbe identification and antimicrobial susceptibility testing analysis results directly from a patient specimen within minutes and hours, respectively, as compared to the multiple days conventional techniques require. Analytical cartridges can be automatically processed by an instrument to carry out each of the steps necessary to identify microbes and to perform antimicrobial susceptibility testing analysis.

Figure 1:
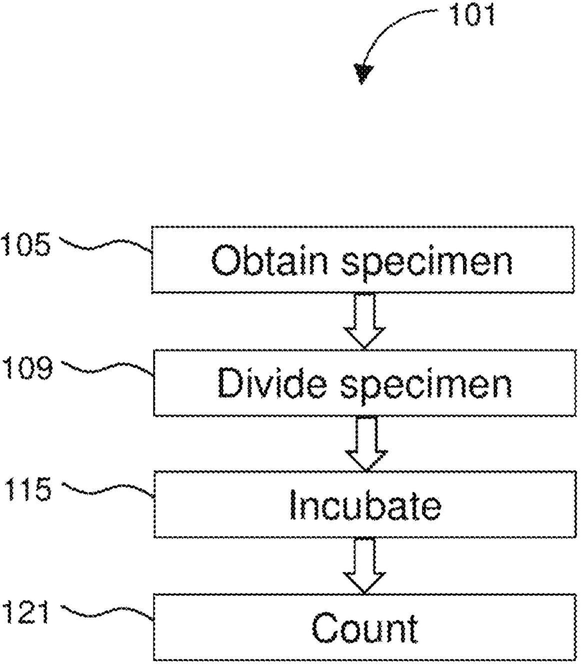
FIG. 1 diagrams a method for antimicrobial susceptibility testing.

FIG. 1 diagrams a method 101 for antimicrobial susceptibility testing. The method 101 includes obtaining 105 a polymicrobial specimen. Without any sample prep, colony purification, or other methods, the raw original specimen is divided 109 into wells. At least some of the wells include different agents or concentrations of one or more agents. The method 101 includes incubating 115 the specimen in the wells to allow differential growth in response to the different agents or concentrations of agents. Finally, individual cells of a specific species are counted 121 in each well to identify an agent or concentration of an agent that inhibit growth of the specific species. Important to the method for antimicrobial susceptibility testing are: (i) no cell/colony purification; (ii) polymicrobial samples; (iii) differential growth; (iv) species-specific detection; and (v) counting of individual cells. To say that no cell or colony purification is involved also means that specimen, be it blood or another bodily fluid, may be directly input into the method—that raw specimen is divided 109 into the wells and incubated 115 with the different agents or concentrations of one or more agents. The method 101 is indifferent to polymicrobial samples and will provide a species-specific result regardless of the presence of other microbes. Species specific detection operates via species-specific probes, such as fluorescently labeled oligos that hybridize to rRNA of a specific species. Differential growth means that the cells of the specific species will grow differently, in different wells, depending the presence of the different antimicrobials or concentrations thereof. Finally, after the labelling, methods and devices of the disclosure are useful for counting individual cells without magnification. The incubating 115 step may include fluorescently labeling the microbes in a species-specific manner, and the counting 121 step may include imaging each well and counting fluorescent spots in an image. The labeling may use a target-specific fluorophore-labeled nucleic acid or nucleic acid analog probe and the counting may rely on fluorescent in situ hybridization. Notably, the steps do not require nucleic acid extraction, purification, or amplification. In certain embodiments, the dividing 109, incubating 115, and counting 121 steps are performed within a cartridge that includes the wells.

Figure 2:
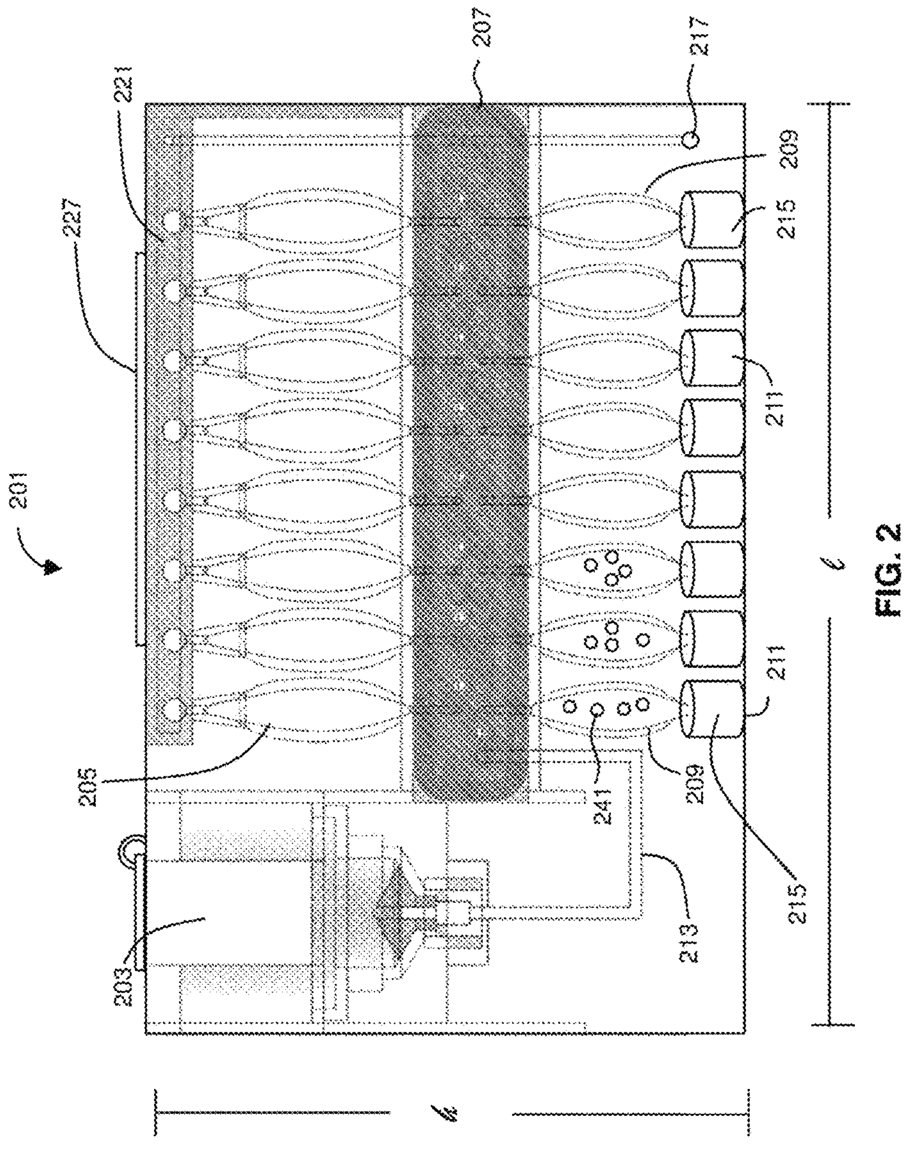
FIG. 2 shows a cartridge.

FIG. 2 shows an exemplary cartridge 201 (e.g., analytical cartridge, testing device). The cartridge 201 includes a sample well 203 connected to division wells 205 via channels 215. Each division well is connectable to a corresponding reagent well 209 by channels through sliding valve 207. The reagent wells 209 may include one or any number of reagents, which may be present in particles 241, which may be, for example, lyophilized beads. Each reagent well 209 may be fluidically connected to a corresponding imaging well 211. One or more of the imaging wells 211 may include a dye cushion 215. The cartridge optionally includes a diluent reservoir 221 which, when button 227 is pressed, flows a diluent (e.g., a growth medium such as trypticase soy broth or saline) into the division wells 205. The cartridge may generally be described according to length l, height h, and width w dimension, e.g., 1 about 6 cm, h about 4 cm and 2 about 2 cm. The analytical cartridge 201 is operable, manually or in conjunction with an instrument (e.g., analyzer) to expose the specimen to, for example, species-specific detectable labels, and magnetic tags that together can form ternary complexes with targets in the specimen for imaging. For example, species-specific detectable labels may be any suitable labels detection by imaging known in the art. In preferred embodiments, the detectable labels are fluorophore-labelled oligonucleotide probes complementary to ribosomal RNA sequences exclusive to a species of microbes. The complexes can be separated from the unbound labels by using a magnetic field on the analytical cartridge 201 to pull the complexes to a surface within the cartridge 201. The microbe complex can then be imaged and the image can be analyzed (manually or by computing device) to identify the microbe present in the specimen. A report may be generated. The report may give, for example, an identity of the microbial target and/or the image. The report may include a qualitative result ("Infection detected"). The report may state if a result is above or below a threshold level for a panel of pathogen targets. A report may give an antimicrobial susceptibility profile. In various embodiments, such as microbial identification embodiments, an analytical cartridge 201 may be pre-loaded with one or more species-specific labels such that a user having suspected a specimen to contain one or more microbes, can select a pre-packed analytical cartridge for microbe identification. In antimicrobial susceptibility testing embodiments, the specimen 105 may be distributed into portions within the cartridge 201, wherein each portion may contain different reagents such as different antimicrobials or different concentrations of one or more antimicrobials.

Detectable labels may include fluorescent molecules, radioactive isotopes, mass tags for mass spectrometry, or chemiluminescent molecules. The detectable label may comprise a species-specific portion to preferentially bind to a specific species of microbe. The species-specific binding molecule may include for example, an antibody to a target-specific molecule or antigen, or an oligonucleotide or polynucleotide probe complementary to a species-specific nucleic acid sequence. In preferred embodiments detectable labelling of microbes comprises fluorescent in situ hybridization (FISH). FISH analysis uses fluorescent probes comprising nucleic acid (or nucleic acid analog) probe moieties and fluorophore probe moieties to bind via re-association with species-specific nucleic acid sequences so that a species of microbe can then be detected optically. For example, probes targeting species-specific 16S rRNA can be used to selectively tag and detect microorganisms. See, Volkhard, et al., 2000, Fluorescent In Situ Hybridization Allows Rapid Identification of Microorganisms in Blood Cultures, J Clin Microbiol., 38(2):830-838, incorporated by reference. In a preferred embodiment, the detectable labels are fluorescently-labelled probe oligonucleotides complementary to ribosomal RNA exclusive to a species of microbe.

Species-specific probes are designed according to methods known in the art. For example, species-specific probes may be designed by using software such as ARB, PRIMROSE, and mathFISH, as well as publically available databases, such as probeBASE, RDP, and SILVA Embodiments of the invention related to identifying a microbe in a specimen may include a number of detectable labels, such as distinct species-specific fluorescent probes, to independently identify multiple distinct species of microbes in a single specimen. The distinct fluorescent probes can comprise distinct nucleic acid probe moieties designed such that under assay re-association conditions, the nucleic acid probe moieties of the fluorescent probes preferentially re-associate with species-specific nucleic acid sequences of distinct species of microbes.

The fluorophores on the distinct fluorescent probes can have distinct photonic signals so that the fluorescent signal for the different species of microbes in the assay can be differentiated by their distinct photonic signals. Imaging methods to distinguish multiple distinct photonic signals are known to those familiar with the art. For example, multiple images can be acquired using distinct pairs of excitation and emission optical filters that correspond to the action spectrum of the distinct fluorophores. Accordingly, a single specimen portion can be tested for the presence of multiple specific target cells or microbes in a single processing and imaging well. The magnetic tags may be any of those known in the art, including paramagnetic particles. Target-specific magnetic tags may specifically bind to a class of microbes, for example to bacteria only.

In certain embodiments, identification of a microbe in a specimen is performed using FISH analysis at constant temperature, where the analysis does not require cell fixation, a user to add additional reagents during the analysis, and does not require washing remove the unbound fluorescent labels, thus allowing for automatic specimen processing within an single cartridge in about 30 minutes or less between initiation of the reaction and obtaining imaging results.

The magnetic tags and detectable labels preferably form complexes with target cells present in the specimen. Magnetic fields can be applied to magnetic particles to physically separate bound detectable labels from unbound detectable labels, in solution, without a washing step. Dye-cushion layers, for example those as described in U.S. Pat. No. 9,643,180, incorporated herein by reference, can be used in conjunction with the magnetic particles and a magnetic field to pull microbes through a dense, opaque, aqueous dye-cushion layer and deposit them on a detection surface in a well of an analytical cartridge for imaging analysis. The dye in the dye-cushion layer is preferably chosen to absorb the excitation and emitted light used by the instrument for imaging. Thus, the signal from unbound detectable labels above the dye cushion layer (the "assay layer") does not significantly interfere with detecting the signal from the labelled target-cell or microbe complexes that are magnetically deposited on the detection surface. Similarly, the use of the dye-cushion may prevent auto-fluorescence from a specimen matrix, which may also be contained in the assay layer, from significantly interfering with detection of the signal from the deposited labelled target-cell or microbe complexes. These attributes of the dye-cushion can make it possible to detect microbes without specimen preparation by the user and without wash steps to remove the unbound label from the cartridge.

Non-magnified digital imaging is preferably used to detect the labeled target cells that have been deposited on the detection surface. In the preferred case of fluorescent labelling, various lenses, illumination sources, excitation light sources, and filters may be used. Imaging systems may include any device capable of producing a digital image of the detectably labelled target microbes in a solution or pulled to a detection surface in a well of a cartridge. Imaging systems may be contained in a subsystem of the instrument described herein. Imaging systems may include, for example, CCD cameras, CMOS cameras, line scan cameras, CMOS avalanche photodiodes (APD's), photodiode arrays, photomultiplier tube arrays, or other types of digital imaging detectors. Imaging can be carried out under a single set of conditions or light sources, filters, and/or lenses may be changed between images to detect different optically distinguishable labels (e.g., different fluorescent probes corresponding to different microbes). The imaging techniques, analyzers, and instruments described in U.S. Pat. Nos. 9,643,180 and 8,021,848, both incorporated by reference, may allow for identification and enumeration of individual bacterium or other target cells.

Figure 3:
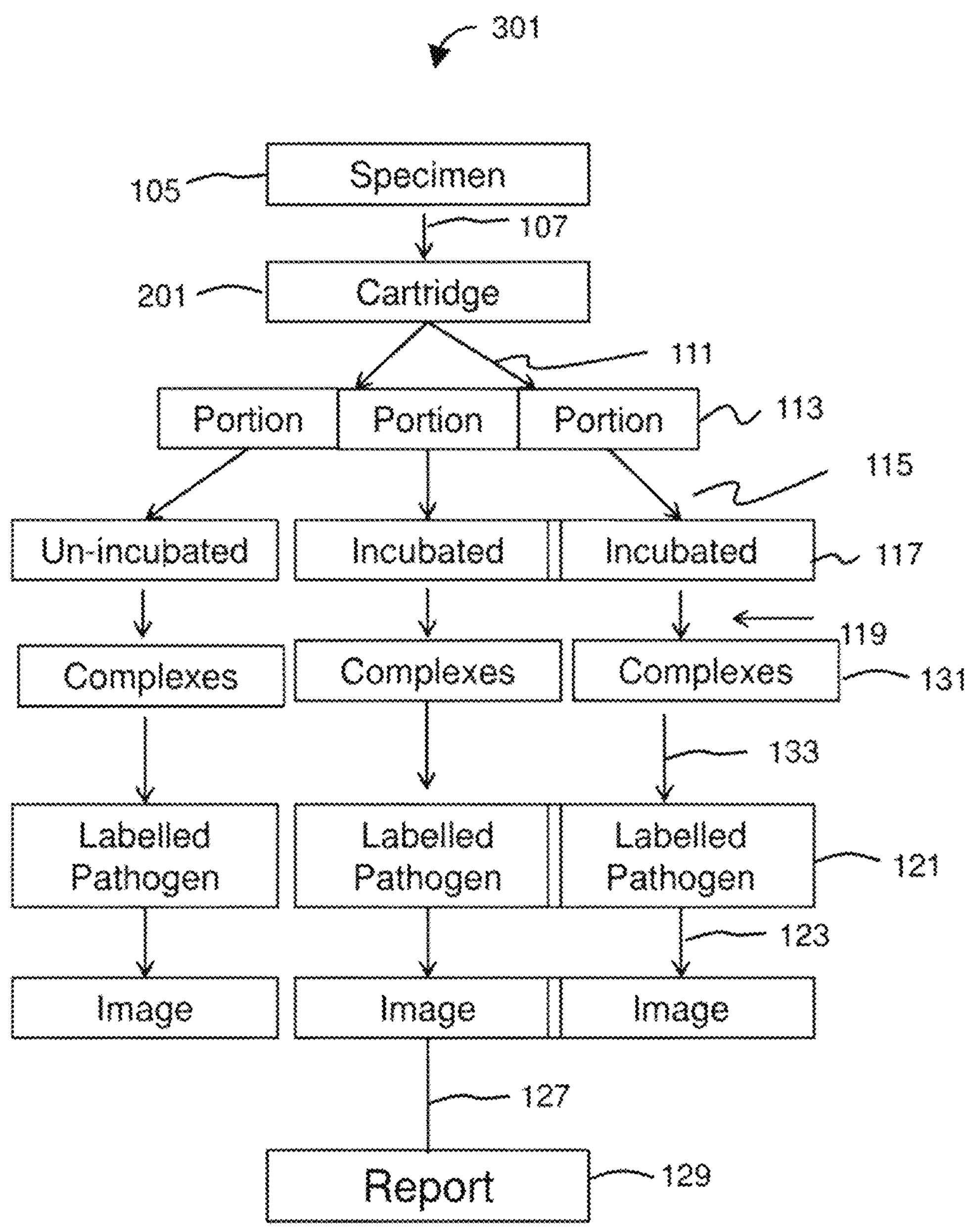
FIG. 3 diagrams steps of another exemplary method of the invention.

FIG. 3 diagrams steps of another exemplary method 301 of the invention. A patient specimen 105 (e.g., a polymicrobial specimen) may be introduced 107 directly into the analytical cartridge 201 and does not require any pre-processing steps. The analytical cartridge 201 is operable, manually, or in conjunction with an instrument, to divide 111 the specimen 105 into a plurality of portions 113 (e.g., partitions) within the analytical cartridge 201. One or more portions 113 may not be exposed to antimicrobial agents and or may be un-incubated. The left-most path shows a portion 113 of the specimen 150 that is unexposed to antimicrobial agents and/or un-incubated and imaged 123 to establish the number of target cells present in the portions before growth incubation (the "time 0 count"). The portions 113 can be incubated 117 in the presence of different antimicrobial agents which may be already present in the analytical cartridge 201 and may be selected based on a target cell or microbe suspected or known to present in the specimen 105. For example, species of bacteria, such as bacteria (e.g., of *Escherichia* spp. (e.g., *E. coli*), *Klebsiella* spp., *Enterococcus* spp., or *Pseudomonas* spp.) associated with urinary tract infections may be suspected to be present in the specimen.

The specimen 105 may be mixed with an amount of growth media within the cartridge 201 at any point between introduction 107 and incubation 115 of the specimen 105 to the analytical cartridge 201. The incubation 115 step may last a suitable amount of time such as about 4 hours to allow for measurable differential growth of the microbes in the specimen 105. The growth media and/or antimicrobial agents may be selected and included in the cartridge 201 based on the microbe to be analyzed in the specimen 105. For example, growth media known to support growth of an identified microbe and therapeutic or antimicrobial agents commonly used to treat the identified microbe may be selected. In preferred embodiments, an analytical cartridge may be pre-loaded with growth media and therapeutic agents for a certain target such that a user, having identified a microbe in a specimen (e.g., determined the source of a patient's infection) can select the appropriate pre-packaged analytical cartridge for antimicrobial susceptibility testing analysis of the identified target microbe.

After incubation 115, the incubated portions 117 can be exposed to, for example, species-specific magnetic tags and detectable labels that can form 119 complexes with a specific microbe in the portions for imaging 123. The microbe 121 complex can then be imaged 123 in the portions and the images 125 can be analyzed 127 (manually or by computing device) to quantify the amount of the microbe 121 present in each portion. By comparing the quantity of microbes in portions that had been incubated in the presence of various antimicrobial agents, one can determine which of those agents inhibits growth. Comparison preferably includes a target cell quantity from a "time zero count" growth reference portion that has been divided off of the original specimen, processed, and imaged without incubation. A report 129 may be generated with results of the analysis 127 and may include the image 125 and a recommendation for treatment.

Target microbes and cells contemplated for testing using systems and methods of the invention include viruses or bacteria. Target microbes are preferentially those that commonly cause the particular type of infection being investigates. For example, for urinary tract infections target pathogens could include *Bacillus antracis, Clostridium difficile, Neisseria gonorrhoeae, Mycobacterium tuberculosis, Acinetobacter baumannii, E. coli, Klebsiella pneumoniae*, or *Pseudomonas aeruginosa* to name a few.

In the case of bacterial targets, for example, specimens can be incubated in the presence of various antibacterial agents and the effects of those agents on target bacterial growth in the specimen can be analyzed to determine effectiveness. The systems and methods described herein can equally be applied to measuring cytotoxic effects of chemotherapeutic agents on cancer cells or to measure the effectiveness of various antiviral agents on viral load in a specimen. The only changes that may be required across various target cells and microbes are the target specific binding molecules (e.g., bacterial cell surface-specific antibodies, viral-specific oligonucleotide probes, or cell specific dyes), the treatments being tested (e.g., antivirals, antibacterial agents, or cancer therapies), incubation times, and, in some cases, the characteristic being analyzed in image analysis (e.g., CFU quantification, viral load, or cell number, morphology, or function).

The cartridge 201 includes an inlet or sample well 203 for receiving a specimen, distribution wells 205, reagent wells 209, imaging wells 211, and channels 213 for moving the specimen between the wells, as well as valves 207 for controlling that movement. The cartridge 201 is operable, when interfaced with an instrument, such as an analyzer, to receive the specimen in the sample well 203 and divide the specimen into portions in the distribution wells 205 through the channels 213. The valves 207 can control the movement of fluid between the distribution wells 205 and the reagent wells 209 and the imaging wells 211. In microbial identification applications of the invention, the valves 207 may be configured to allow one or more portions bypass the distribution wells 205 and proceed directly to one or more reagent wells 209 and imaging wells 211. The reagent wells 209 may be pre-filled with reagents for labelling a microbe for imaging. The labelling reagents may be lyophilized for storage and activated upon contact with the fluid specimen portion. The reagent wells 209, for example, may contain detectable labels and magnetic tags such that, as a specimen portion passes through the reagent well 209, the microbe-specific complexes are formed comprising the target microbe, detectable labels, and magnetic tags.

In other embodiments of the invention, the valves 207 may also be configured to allow one or more portions to bypass the distribution wells 205 and proceed directly to one or more reagent wells 209 and imaging wells 211 to provide a zero growth reference or baseline for antimicrobial susceptibility testing. The distribution wells 205 can be pre-filled with growth media and/or one or more antimicrobial agents. The valves 207 can hold the specimen portions in the distribution wells 205 to be incubated in the presence of the various antimicrobial agents for any period of time.

Figure 4:
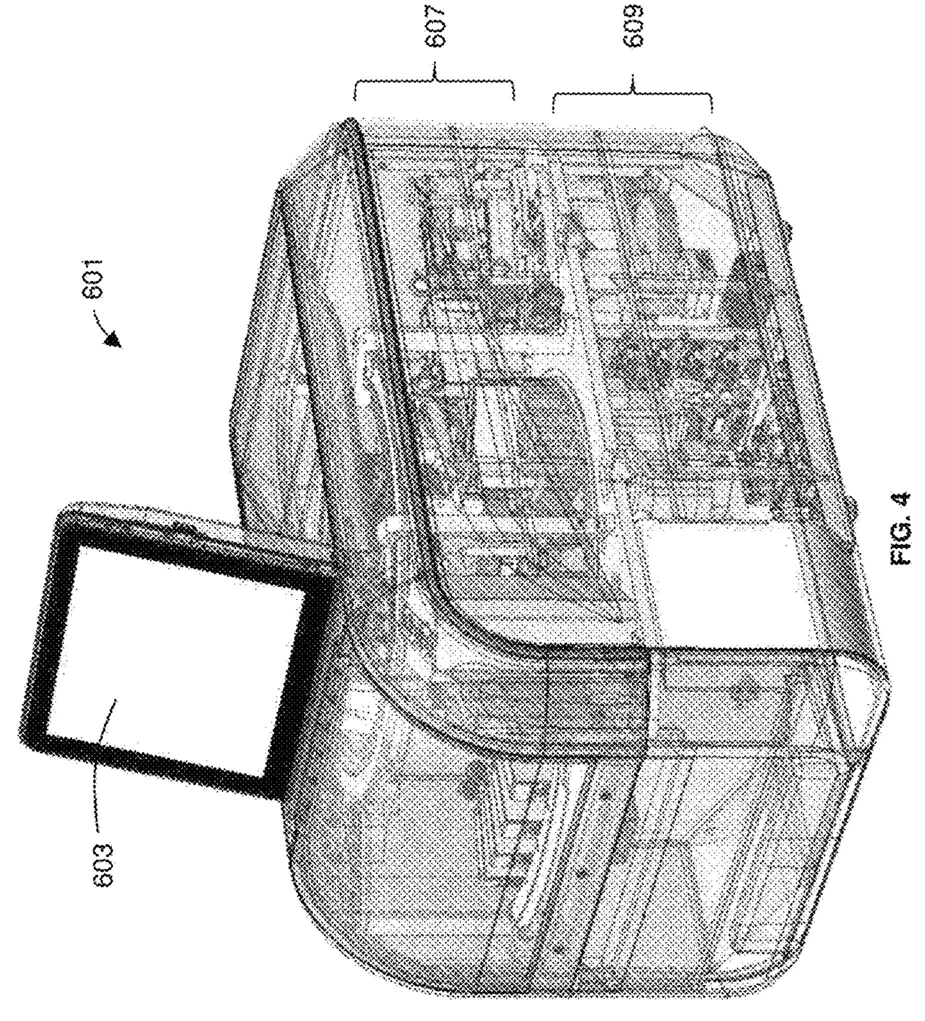
FIG. 4 shows an instrument.

FIG. 4 shows an exemplary instrument 601 (e.g., analyzer) for performing microbe identification and antimicrobial susceptibility testing of specimens within the cartridge 201. The instrument 601 may be used to interact with the cartridge 201 to carry out target cell identification and antimicrobial susceptibility testing of specimens. The instrument 601 includes at least one user interface 603 (e.g., a touch screen) to display prompts, results, reports and to receive commands. The instrument 601 can comprise different functional areas and subsystems. These may include a carousel for transporting and incubating analytical cartridges; a fluidics subsystem providing a pneumatic interface to the cartridge fluidics; a magnetic; an upper portion 607 for housing processing and incubation equipment; and a lower portion 609 for housing electronics, imaging and pneumatic equipment.

Figure 5:
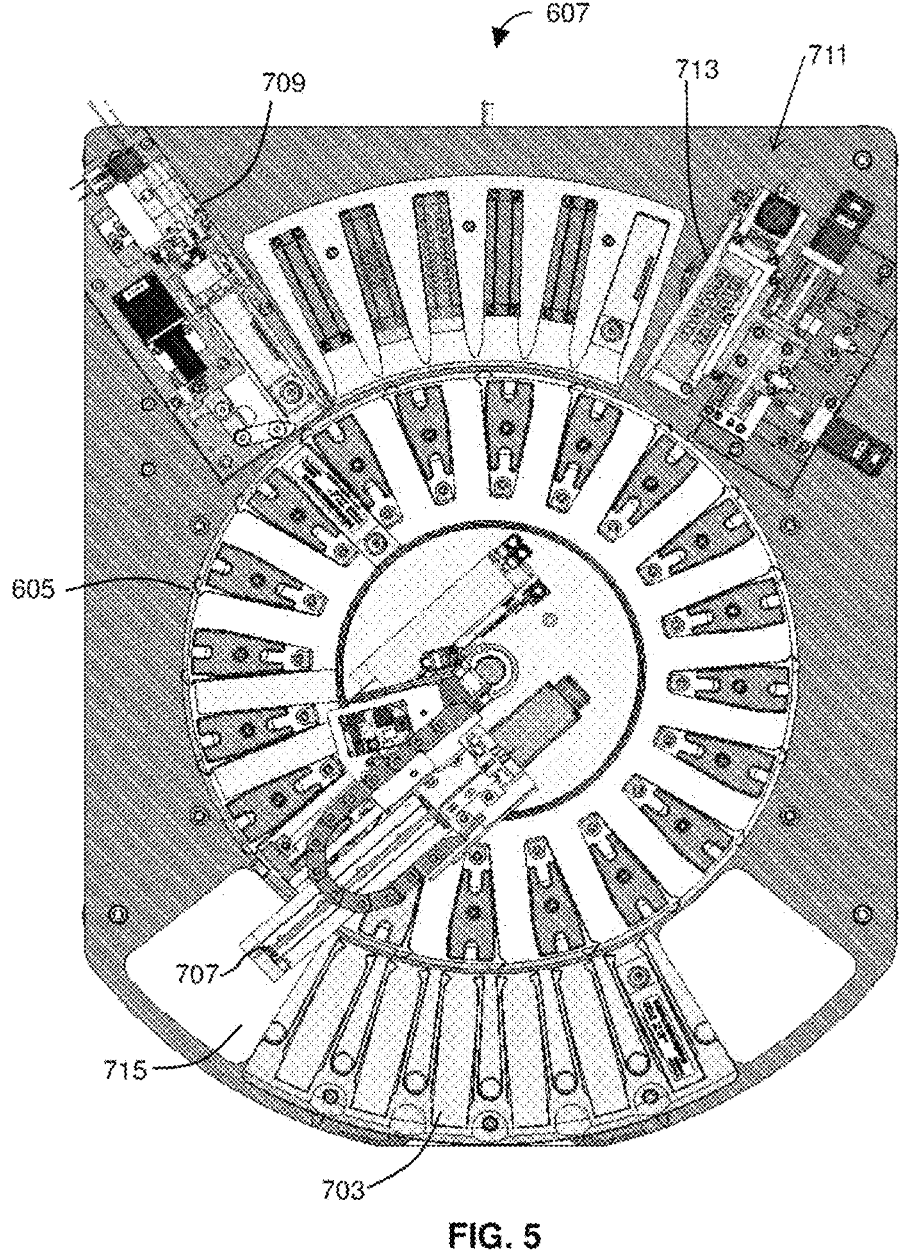
FIG. 5 is a top view of components within the instrument.

FIG. 5 is a top view of components within the upper portion 607 of the instrument 601, showing the carousel that aids in moving the cartridges 201 around the instrument 601.

The instrument 601 may include a loading tray 703 for accepting and cataloging a plurality of analytical cartridges 201.

The instrument 601 may also include a carousel 605 and a mechanical cartridge conveyance 707 to accept, move and manipulate analytical cartridges within the instrument 601. The instrument 601 may also include a task scheduler. The instrument 601 is preferably controlled by a computer to automate manipulation of analytical cartridges, performance of microbe identification and antimicrobial susceptibility testing, and generation of results. The instrument 601 may include a plurality of subsystems to perform methods of the invention.

Subsystems of the instrument 601 may include a pneumatic subsystem 709, a magnetic subsystem 711, an imaging subsystem 713 and a waste subsystem 715 (e.g., a disposable bin that spent cartridges 201 can be pushed into). The magnetic subsystem 711 may include, for example, a permanent magnet or an electro-magnet to provide a magnetic field to deposit complexes of magnetic particles and targets on the detection surface of the analytical cartridge for imaging. The imaging subsystem 713 may be such as those described in U.S. Pat. Nos. 9,643,180 and 8,021,848, both incorporated herein by reference, to capture images of microbes, and a stage to manipulate the detection surface of the analytical cartridge 201 relative to the imaging module of the instrument 601. The imaging subsystem 713 can be operably associated with the computer to provide image processing, analysis, and display capabilities. The pneumatic subsystem 709 may be operable to drive movement of the specimen 105 and reagents within the analytical cartridge 201 through, for example, manipulation of valves 207 (e.g., plungers and actuators) using functionality provided by pneumatic pressure or vacuum. In some embodiments, hydraulic or mechanical means may also be incorporated into the pneumatic subsystem 709 to effectuate movement of the specimen 105. The waste subsystem 715 may include a receptacle (e.g., a removable bin) for disposal of the cartridge 201 after use.

The instrument 601 may also include one or more incubation areas for holding (or storing) analytical cartridges during incubation for growth and/or assay incubation. The incubation area may include a heating and/or cooling element and a thermostat to control that element to maintain the incubation area at a desired temperature for growth of the target cells or microbes (e.g., 35 degrees C.) or for carrying out assay incubation.

In some embodiments the mechanical cartridge conveyance 707 (e.g., mechanical conveyor arm) may be operable to manipulate the analytical cartridge 201 amongst the various subsystems within the instrument 601. In some embodiments of the invention, the mechanical cartridge conveyance 707 transfers each of the the cartridge 201 between the carousel 605 and the various subsystems of the instrument. The mechanical cartridge conveyance 707 applies a pushing force to transfer the cartridge 201 onto and off of the carousel 605. The carousel 605 rotates to position an analytical cartridge 201 adjacent another one of the subsystems and the mechanical cartridge conveyance 707 may then apply force to slide the analytical cartridge 201 onto the subsystem. The cartridge 201 are never grabbed by the mechanical cartridge conveyance 707 or any other elements of the instrument 601. Sliding, or pushing the analytical cartridge 201 within the instrument 601 reduces exposure to debris.

In some embodiments, the instrument includes a task scheduler for managing the the cartridge 201 within the instrument 601. The task scheduler is operable to control the movement, such as the transport and transfer of each of the the cartridge 201 amongst the plurality of subsystems. In some embodiments, the time each analytical cartridge 201 spends in a subsystem may also be managed by the task scheduler. The task scheduler may reserve time on various subsystems as needed for analysis of each of the the cartridge 201. In some embodiments of the invention, the task scheduler may manage the movement of an analytical cartridge 201 (i.e., the steps/parameters of the analysis to be performed) by identifying the contents of the cartridge.

In some embodiments, the instrument 601 may also include a reader operable to analyze unique identifiers (e.g., barcodes) 219 located on an analytical cartridge 201. The contents of an analytical cartridge 201 and the required processing may be associated with a unique identifier 219 on the analytical cartridge 201. Each of the the cartridge 201 may include a unique identifier readable by the instrument 601. The instrument 601 may read the unique identifier 219 via a reader and associate the unique identifier 219 with a particular set of instructions for the task scheduler to execute. The reader may be located on the exterior of the instrument 601 and may read the unique identifier 219 before the analytical cartridge 201 is transferred from the loading rack 703 to the carousel 605. The unique identifier 219 may be a barcode and may be specific/unique to the specimen in the analytical cartridge 201.

A specimen may be directly inserted into the sample well 203. The pneumatic port 217 may be opened to apply pressure or vacuum to distribute the specimen to the wells within the analytical cartridge 201. The specimen may first be distributed from the sample well 203 to the distribution wells 203 and held there by valves 207 during incubation and released to the reagent wells 209 for labelling and then to the imaging wells 211 for imaging. The analytical cartridge 201 has a unique identifier 219 (e.g., barcode) that when analyzed or read by an instrument or a reader in the instrument, associates the cartridge with a set of instructions for processing within the instrument.

The cartridge 201 can then be subjected to a magnetic field (e.g., placed on a permanent magnet) to pull the complexes to the detection surface 215 on the bottom of the imaging well 211. The imaging wells 211 may contain a dye cushion that forms a dense opaque aqueous layer lying below the upper layer (containing biological matter, detectable labels, complexes, magnetic tags) in the imaging well 211 as described herein. The complexed magnetic particles are forced through the lower dye cushion layer and deposited on the detection surface 215 of the imaging well 211 by the magnetic field pulling the complexes and microbe complexes through the dye cushion layer to a detection surface 215 on the imaging well 211. The detection surface 215 may be optically clear to allow for optical detection of microbes. After processing and pull-down with the magnetic field, the cartridge 201 can be placed on an imaging system for image processing as described herein.

Species-specific, fluorescent oligonucleotide probes may be used to fluorescently label the target microbe such that imaging of the fluorescent labels provides identification and quantification of target microbe (e.g., a cell count for a target bacterium in the specimen). Analytical cartridges can have any number of distribution wells and corresponding reagent and imaging wells. In a preferred embodiment, analytical cartridges have a "time 0 count" reference portion, and differential growth analysis of one or more antimicrobial agent each present in at least two separate concentrations. The concentrations chosen in some embodiments should preferably correspond to the accepted antimicrobial susceptibility testing breakpoint concentrations established by CLSI and/or EUCAST for particular target species and antimicrobial agents.

While systems and methods of the invention are primarily described herein in the context of an analytical cartridge having interconnected wells for automated processing, the techniques can also be performed in any known fluidic platform including manual processing in the wells of microtiter plates or on substrates with droplets functioning as wells. In some embodiments, cartridges comprise at least eight wells and can be duplexed to include at least sixteen wells made up of two eight well sections. That said, the number of wells is preferably large (e.g., one hundred or more) and is limited only by the size constraints of the cartridge and instrument.

By quantifying the amount of target cell or microbe present in each specimen portion after incubation in the presence of various antimicrobial agents and comparison to a "time 0 count" reference determined before incubation, the effect of each antimicrobial agent on target cellular replication can be determined. By determining which antimicrobial agents best inhibited growth, an effective therapy can be determined to treat the patient's infection.

Figure 6:
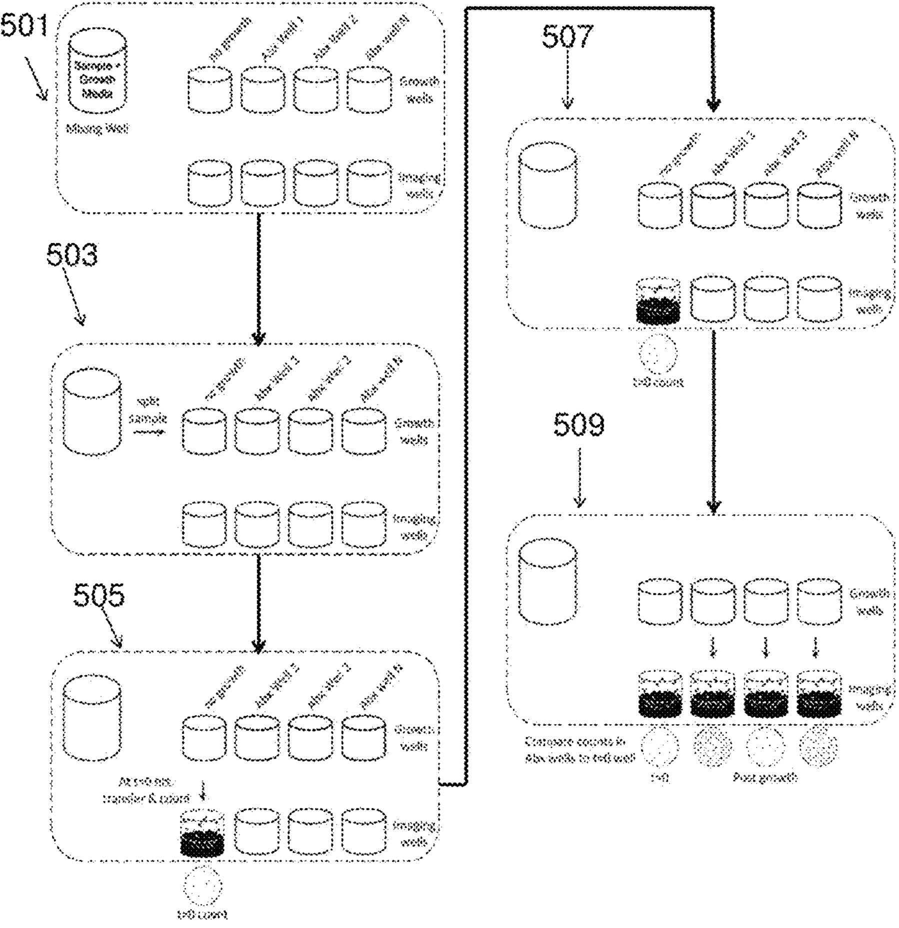
FIG. 6 is an example of a workflow for performing antimicrobial susceptibility testing.

FIG. 6 is an example of a workflow for performing antimicrobial susceptibility testing of a specimen comprising bacteria. The workflow is exemplary of the incubation and processing steps that may be performed in an analytical cartridge according to various methods of the invention. A specimen can be mixed with growth media 501 that may be selected based on knowledge of the target microbe present in the specimen (e.g., cation-adjusted Mueller Hinton broth selected for analysis of *E. coli* in a specimen). The specimen and growth media can then be divided 503 into a number (n) of distribution wells for incubation 507. One or more of the distribution wells may contain various antimicrobial agents. One or more portions may be analyzed without incubation (t0 specimens) 505 to quantify target microbes for subsequent comparison to specimen portions that have been analyzed following incubation in the presence or absence of antimicrobials. Incubation in the absence of therapeutic agents may provide important information including an indication of non-viable microbes which can happen, for example, if a patient is already being treated with an antimicrobial agent. Analysis of such incubated portions can also serve as an internal control for growth-inhibiting interferences and reagent stability.

Preferably, the bacteria or other target cell has already been identified and the various antimicrobials have been selected accordingly as, for example, antimicrobials commonly used to treat the identified bacteria. Each distribution well may contain a single antimicrobial agent or a unique combination of antimicrobial agents to assess combined effects on target cell growth. Different antimicrobial agents at different concentrations may be combined with the specimen portions or aliquots in different distribution wells and some distribution wells may be used for replicating treatment with the identical antimicrobial agents to strengthen results. Specimen portions or aliquots in some distribution wells may not be combined with antimicrobial agents to quantify uninhibited growth and/or to detect growth inhibition due to either non-antimicrobial inferences or reagent instability.

After incubation 507, the incubated specimen aliquots can be processed and imaged in a manner similar to the "time 0 count" specimen aliquot 505 and the counts of bacteria or other microbes can be compared to each other, the "time 0 count" specimen aliquot, or to other control counts 509 to determine effectiveness for the certain concentrations antimicrobial agents or combinations thereof. Preferably, an antibiotic is recommended for treatment at a concentration that does not permit growth.

Figure 7:
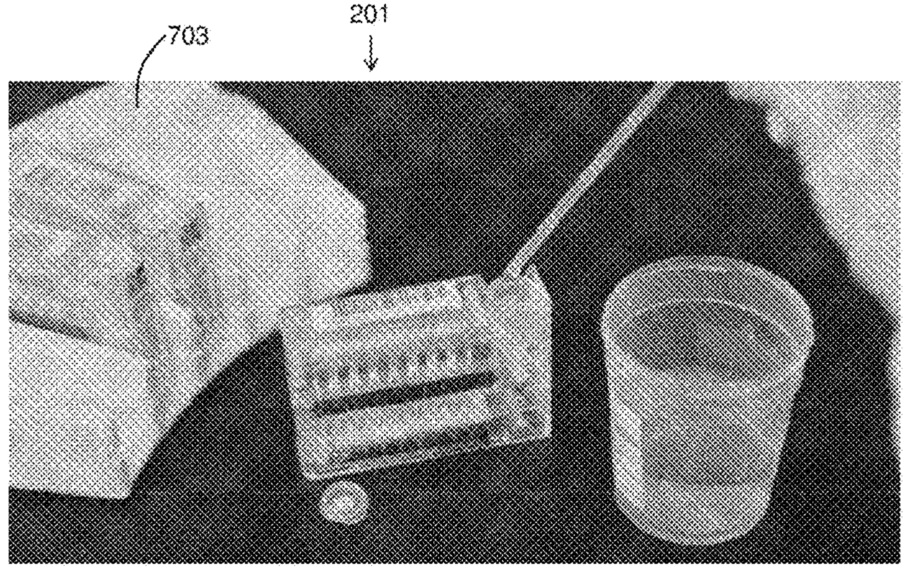
FIG. 7 shows transferring a specimen into the sample well of a cartridge.

FIG. 7 shows a user transferring a specimen 105 directly into the sample well 203 of an analytical cartridge 201. In this example, the specimen 105 is pipetted from a specimen collection device 1001 (e.g., a specimen collection container, a swab, etc.) into the sample well 203 of an analytical cartridge 201. In other embodiments, a specimen collection device 1001 (e.g., swab), may be directly inserted into the sample well 203 of an analytical cartridge 201.

Figure 8:
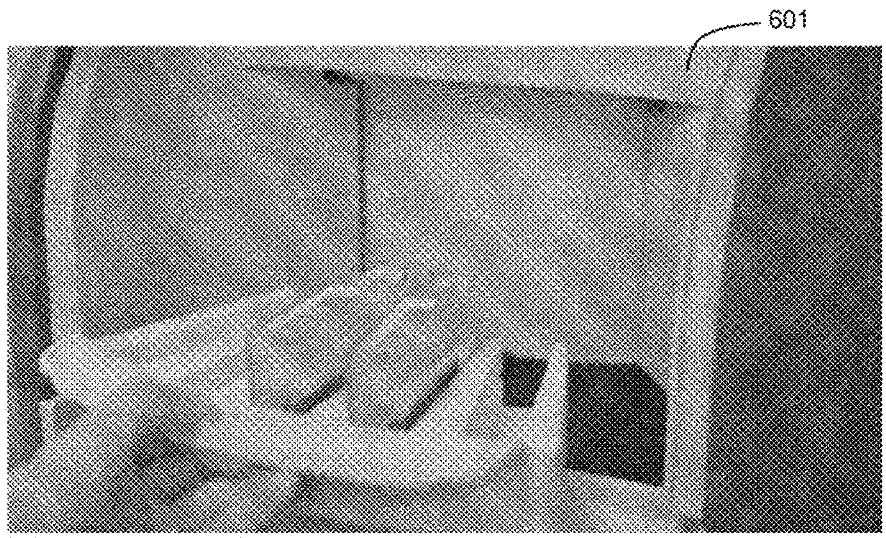
FIG. 8 shows cartridges being loaded into a loading tray.

FIG. 8 depicts a plurality of the cartridge 201 being loaded into the loading tray 703 before be transported into the instrument 601.

The instrument may include or be connected to a computer useful for performing steps of the methods. The computer may be operable to control the instrument 601 and the cartridge 201 and/or to process imaging results. The computer may comprise a processor coupled to a non-transitory memory device. The memory preferably stores instructions executable by the processor to cause the system to manipulate the cartridge 201 within the instrument 601 and to obtain and process images of labelled microbes.

Processor refers to any device or system of devices that performs processing operations. A processor will generally include a chip, such as a single core or multi-core chip, to provide a central processing unit (CPU). A process may be provided by a chip from Intel or AMD. A processor may be any suitable processor such as the microprocessor sold under the trademark XEON E7 by Intel (Santa Clara, CA) or the microprocessor sold under the trademark OPTERON 6200 by AMD (Sunnyvale, CA). In Memory refers a device or system of devices that store data or instructions in a machine-readable format. Memory may include one or more sets of instructions (e.g., software) which, when executed by one or more of the processors of the computer can accomplish some or all of the methods or functions described herein. Preferably, the computer includes a non-transitory memory such as a solid state drive, flash drive, disk drive, hard drive, subscriber identity module (SIM) card, secure digital card (SD card), micro SD card, or solid-state drive (SSD), optical and magnetic media, others, or a combination thereof. In a preferred embodiment, the memory includes task scheduler software. Different task scheduler instructions may be associated with specific unique identifiers. Scanning a unique identifier on the analytical cartridge 201 via a reader or a barcode scanner on or in the instrument 601 may cause processors to execute the task scheduler instructions specific to the unique identifier.

An input/output device 603 is a mechanism or system for transferring data into or out of a computer. Exemplary input/output devices, such as the touch screen, include a video display unit (e.g., a liquid crystal display (LCD)), an alphanumeric input device (e.g., a keyboard), a cursor control device (e.g., a mouse), a barcode scanner, a reader, a disk drive unit, a signal generation device (e.g., a speaker), an accelerometer, a microphone, a cellular radio frequency antenna, and a network interface device, which can be, for example, a network interface card (NIC), Wi-Fi card, or cellular modem. Input/output devices may be used to allow a user to control the instrument 601 and display results and generate a report obtained from the analysis of the cartridge received by the instrument 601.

EXAMPLES

Example A. Identification and Antimicrobial Susceptibility Testing/Minimum Inhibitory Concentration Analysis of Urinary Tract Infections (UTIs) Using Microtiter Plates Analysis of urine specimens was performed to determine presence of a urinary tract infection, if the patient was infected with one of the four most common UTI-causing microbes (i.e., *E. coli, K. pneumoniae, Enterococcus* spp., and *P. aeruginosa*), and which of four primary antimicrobials would be effective in treating a UTI. Urine was added directly to an analytical cartridge of the invention for testing and to growth media for incubation within the cartridge. If positive for one of the four UTI microbes, then an antimicrobial susceptibility testing was performed. Identification results were obtained in thirty minutes and antimicrobial susceptibility testing results were obtained in four hours. Minimum inhibitory concentration (MIC) analysis was performed using exemplary techniques of the invention.

Urine specimens were tested for the presence of *E. coli, K. pneumoniae, Enterococcus* spp., and *P. aeruginosa* with the limit of detection for each being less than or equal to 10,000 CFU/mL (a common threshold for diagnosing a UTI). Species-specific labels were used. In this example, all four target microbes were detected within 30 minutes using isothermal FISH reactions and universal reaction diluent. Detection of all strains (10 *E. coli,* 11 *Klebsiella* spp., 10 *P. aeruginosa*, and 6 *Enterococcus* spp.) of each species was achieved with no off-target detection. Cross reactivity of FISH probes was analyzed for *E. coli, K. pneumoniae, Enterococcus* spp., and *P. aeruginosa* against 15, 10, 10, and 10 different species of bacteria respectfully with no cross-reactivity observed.

Limit of detection (LoD) results using 30% urine spiked with microbes *E. coli, K. pneumoniae, Enterococcus* spp., and *P. aeruginosa* across 4 specimens are shown in Table 1 indicating a high analytical sensitivity for UTI-causing microbes.

Figure 9:
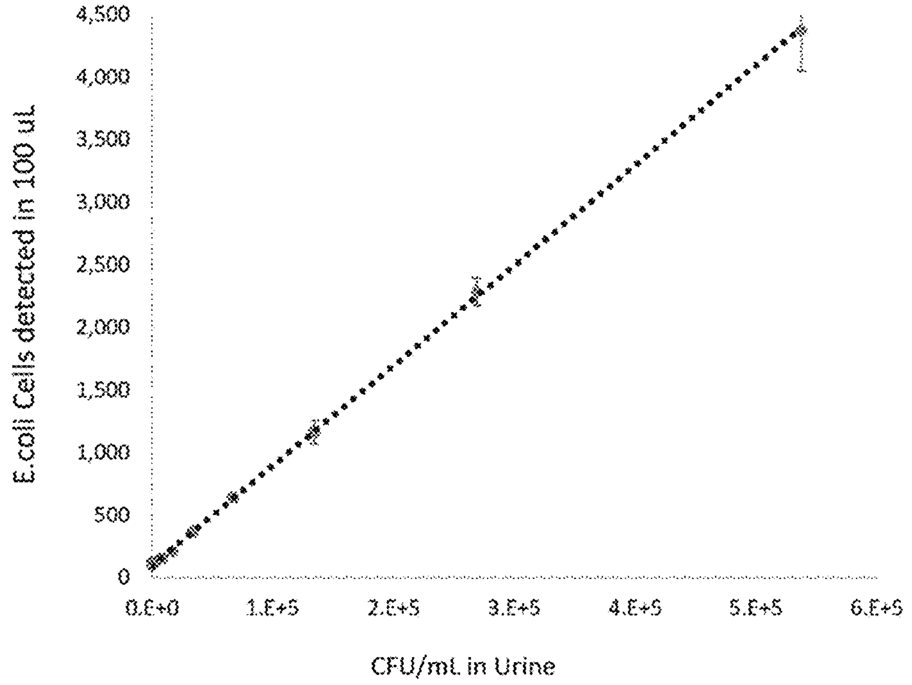
FIG. 9 shows a number of individual *E. coli* cells counted.

FIG. 9 shows a number of *E. coli* cells counted using instruments, methods, and cartridges of the disclosure to analyze samples spiked at different numbers of colony forming unites (CFU) per mL into urine.

Figure 10:
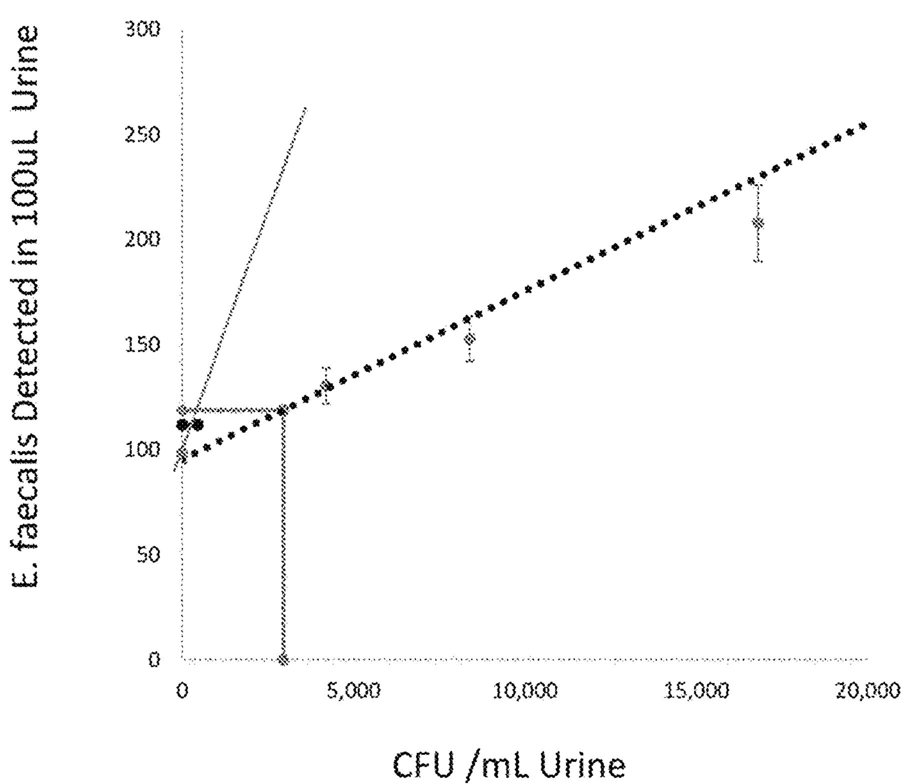
FIG. 10 shows a number of *Enterococcus faecalis* cells counted.

FIG. 10 shows a number of *Enterococcus faecalis* cells counted using instruments, methods, and cartridges of the disclosure to analyze samples spiked at different numbers of colony forming unites (CFU) per mL into urine.

Methods of microbe detection and identification described herein can be used to rapidly detect other species of microbes like *Bacillus antracis* (*B. antracis*) and *Clostridium difficile* (*C. difficile* or C. diff).

TABLE 1

| Target | Range of LoD (CFU/mL) 4 urine specimens |
|---|---|
| *E. coli* | 6E3 to 1E4 |
| *Enterococcus* spp. | 2E3 to 5E3 |
| *Klebsiella* spp. | 6E3 to 1E4 |
| *P. aeruginosa* | 3E3 to 8E3 |

In another experiment, seven to ten strains of each of the four identified microbes were subjected to AST analysis for common antimicrobials using both exemplary methods of the invention and conventional broth microdilution, and the results were then compared.

Figure 11:
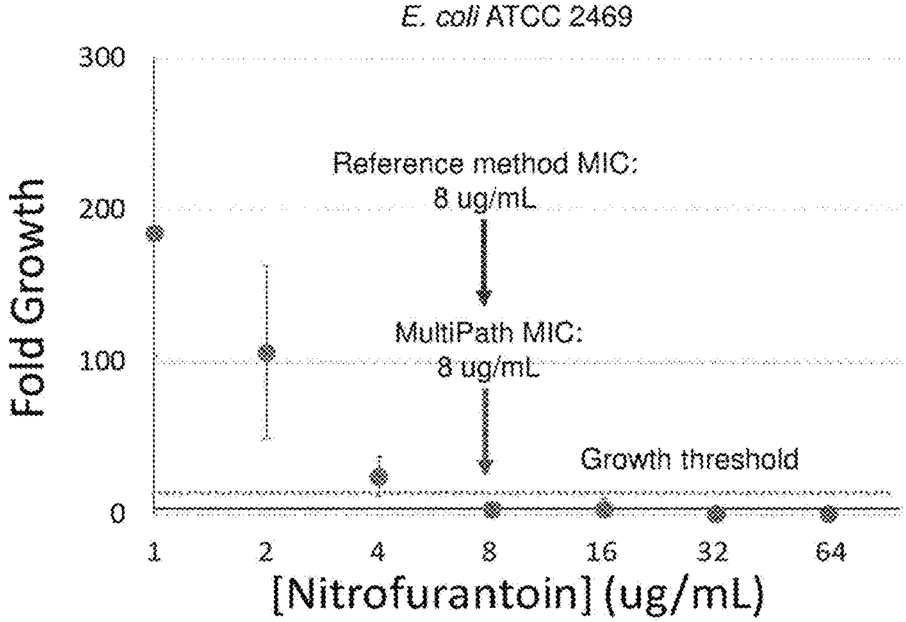
FIG. 11 gives results of a test.

FIG. 11 gives the specific results, for example, for strain ATCC 2469 of *E. coli* for nitrofurantoin. Essential agreement results between conventional and methods of the invention are shown below in Table 2.

TABLE 2

| Target | Antibiotic | Essential Agreement |
|---|---|---|
| *E. coli* | Ciprofloxacin | 100% |
| | Clofazimine | 100% |
| | Nitrofurantoin | 100% |
| | Trimethoprim/ sulfamethoxazole | 100% |
| *P. aeruginosa* | Ciprofloxacin | 100% |
| | Clofazimine | 100% |
| | Nitrofurantoin | 100% |
| *Klebsiella* spp. | Ciprofloxacin | 100% |
| | Clofazimine | 100% |
| | Nitrofurantoin | 100% |
| | Trimethoprim/ sulfamethoxazole | 100% |
| *Enterococcus* spp. | Ciprofloxacin | 93% |
| | Clofazimine | 100% |
| | Nitrofurantoin | 100% |

To test robustness to variable inoculation levels, inoculations covering 4 orders of magnitude were tested using the rapid AST methods and compared to known MIC results. 100% essential agreement was observed for all tested specimens (three species against four different antimicrobials) as shown in Table 3.

TABLE 3

| Target | Antibiotic | Essential Agreement* |
|---|---|---|
| *E. coli* | Ciprofloxacin | 100% |
| | Clofazimine | 100% |
| | Nitrofurantoin | 100% |
| | Trimethoprim/ sulfamethoxazole | 100% |
| *P. aeruginosa* | Ciprofloxacin | 100% |
| | Nitrofurantoin | 100% |
| *Klebsiella* spp. | Ciprofloxacin | 100% |
| | Clofazimine | 100% |
| | Nitrofurantoin | 100% |
| | Trimethoprim/ sulfamethoxazole | 100% |

Figure 12:
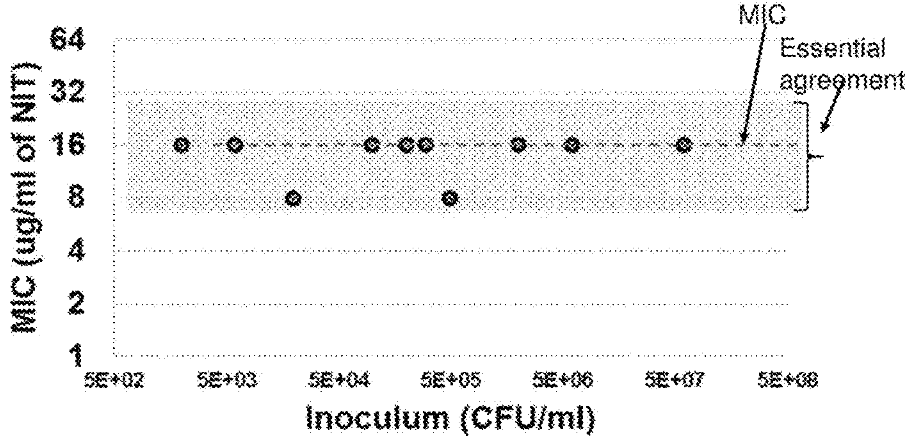
FIG. 12 shows results of another test.

FIG. 12 depicts results across various inoculum concentrations for Nitrofurantoin MIC testing. The impact of polymicrobial specimens was tested by spiking specimens with target *E. coli* along with non-target bacteria including *Staphylococcus epidermidis, Micrococcus luteus, Corynebacterium minutissimum, Staphylococcus aureus, Acinetobacter baumannii, Citrobacter freundii*, and *Klebsiella pneumoniae* secreting NDM1. High concentrations of 1e5, 1e6, and 1e7 CFU/ml of non-target bacteria were used with essential agreement of 100%, 100%, and 96% respectively observed in MIC testing for 5 different antimicrobials. Greater than 98% essential agreement was observed across 84 specimens tested. *E. coli* MIC for imipenem was unaffected in the presence 1E7 CFU/mL of a carbapenemase secreting *K. pneumoniae* NDM1.

Example B. Antimicrobial Susceptibility Testing: *E. coli*

Urine specimens spiked with a strain of *E. coli* sensitive to clofazimine and a strain resistant to clofazimine. The specimens were tested using an exemplary systems described herein (analytical cartridges and instrument). The specimens were incubated for four hours in 32 μg/mL of clofazimine.

Figure 13:
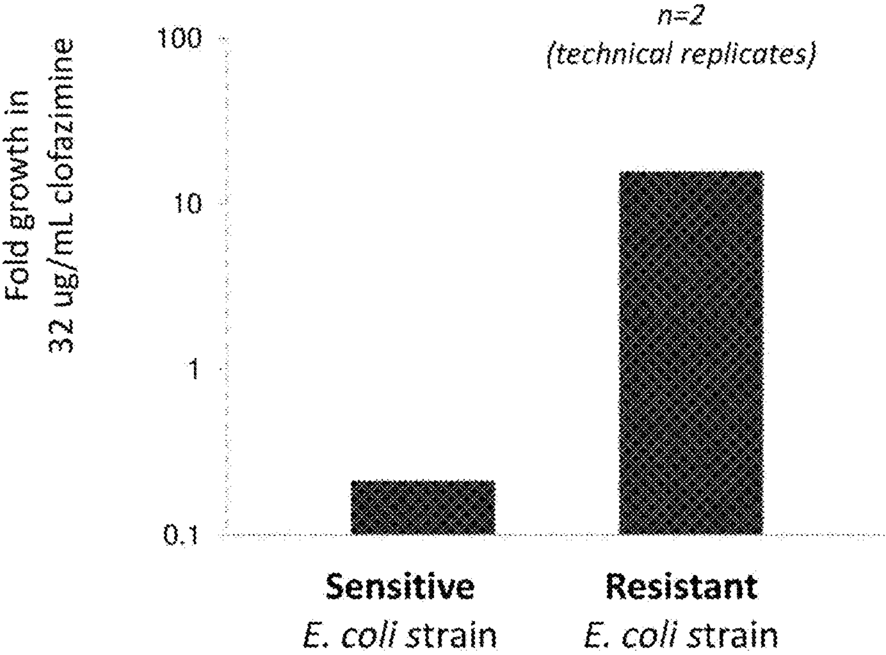
FIG. 13 depicts growth results.

FIG. 13 depicts the growth results, which evidences that the methods and systems of the present disclosure successfully differentiate between the clofazimine-sensitive and clofazimine-resistant strains of *E. coli* as described herein.

Example 1. Limit of Detection (LoD) for Gram-Negative Bacteria Using a Novel, Rapid Fluorescence In Situ Hybridization Assay Overview: The following example demonstrates that very low concentrations of cells can be detected using the novel isothermal fluorescence in situ hybridization method. The limit of detection for three common human urinary tract infection (UTI) pathogens are shown.

Experimental Methods:

Bacterial cell preparation: Bacterial cultures for *E. coli* ATCC 19138, *K. pneumoniae* ATCC 700603 and *P. aeruginosa* ATCC 9721 were obtained by inoculating Trypticase Soy Broth (TSB, Hardy Diagnostics cat. U65) with 3 to 5 colonies from fresh tryptic soy agar plates (TSA, BD cat. 221185) and growing for 1.5 to 3 hours at 35° C. to achieve log-phase growth. After the cells had reached an optical density reading at 600 nm of 0.15-0.30, cells were placed on ice for at least 15 minutes before dilution. After cooling, the cells were diluted in 1× cation-adjusted Mueller-Hinton broth (MHBII, Teknova cat. M5860) to the concentrations to be assayed (approximately 19200, 9600, 4800, 2400, 1200, 600, 300, and 150 colony-forming units (CFU)/reaction). For more accurate cellular concentrations, these estimated bacterial inputs were adjusted using colony counts. Plate counts were determined by diluting the log-phase cultures to about 500 CFU/mL in MHBII, plating 100 μL on TSA plates and counting colonies after growth at 35° C. for 16 to 24 hours. Using the average plate counts, the actual CFU present in each concentration tested was computed.

Preparation of Magnetic Particles: Polyaspartic acid-conjugated magnetic particles (Fluidmag-PAA, Chemicell, cat. 4108) and carboxyl-coated magnetic particles with high iron (Carboxyl Magnetic Particles, Spherotech, cat. CM-025-10H) were used to non-specifically capture bacterial cells. Each particle was diluted 1:40 into 50 mM Epps buffer, pH 8.2, with final concentrations of approximately $1.38\times10^9$ particles per reaction for the polyaspartic acid particles and $3.46\times10^9$ particles per reaction for the carboxyl particles. Fluorescent magnetic microspheres containing a green dye (Dragon Green Fluorescent Microspheres, BANGS Laboratories, cat MEDG001) were added to the suspension at a final concentration of $3\times10^6$ particles/mL. These particles enable the optical system to focus on the correct plane. The magnetic particle mixture was sonicated for 1 minute immediately prior to use to minimize aggregation.

Preparation of FISH probes: Two species-specific DNA oligomer sets for *E. coli* and *K. pnuemoniae* and one for *P. aeruginosa* was heated in a water bath between 80-85° C. for 10 minutes and then placed on ice to reduce aggregation. A DNA oligomer set contained a species-specific DNA oligonucleotide labeled with a fluorescent dye (Alexa647N, Thermo Fischer) on either the 5' end, or on both the 5' and 3' ends of the oligonucleotide, and 2-6 helper oligonucleotides that bind adjacent or near the specific probe and are designed to disrupt the local secondary structure of the ribosomal subunit, and allow the labeled, specific probe greater hybridization efficiency to the target rRNA. Probe sequences used in this example are shown in Table A in FIG. 17.

Preparation of the dried hybridization buffer plates: A mixture of 10×SSC (1.5M NaCl, 0.15M Sodium citrate, Sigma, cat. S6639), 2.6% w/v CHAPSO (Sigma cat. C3649), 2.4% w/v SB3-12 (Sigma cat. D0431), 0.43M Guanidine thiocyanate (Sigma cat. G9277) and 0.6% w/v Cetrimide (Sigma cat. M7365) was prepared. 30 uL of this mixture was added to each well of a 96 well plate. The plates were placed into a convection oven at 50° C. and allowed to dry overnight. When 100 uL of liquid is added to these wells, the correct hybridization buffer concentrations of 3×SSC (0.45M NaCl, 0.045M Sodium citrate), 0.77% w/v CHAPSO (Sigma cat. C3649), 0.72% w/v SB3-12 (Sigma cat. D0431), 0.13M Guanidine thiocyanate (Sigma cat. G9277) and 0.18% w/v Cetrimide (Sigma cat. M7365) are achieved.

Limit of Detection (LoD) Assay procedure: A mixture of DNA oligonucleotide sets appropriate for the bacteria of interest was combined with urine and a concentrated cation-adjusted Mueller Hinton Stock (MHBII) to make a final solution containing 1×MHBII and 30% pooled human urine (Innovative Research, cat. IRHUURE500 ML). Probe concentrations varied between different bacterial species but ranged from 0.2-0.6 μM for the labeled oligonucleotide and 1.5-6 μM for the corresponding helper probes. 90 uL of this mixture was placed into the appropriate dried hybridization buffer plate. 10 uL of the magnetic particle mixture was added, followed by 10 uL of the appropriate cell dilution. Twelve replicates of each cell concentration and 24 replicates of the blank (media containing no bacteria) were assessed for each target bacteria tested. 100 μL of the final reaction mixture was transferred to a microtiter plate containing 50 μL per well (previously dried) of "dye-cushion" (50 mM TRIS pH 7.5 (Sigma cat. T1075), 7.5% v/v Optiprep (Sigma cat. D1556), 50 mg/mL Direct Black 19 (Orient cat. 191L) and incubated at 35° C. for 30 minutes to allow for the simultaneous rehydration of the "dye-cushion", labeling of bacterial cells, and binding of magnetic particles to bacterial cell surfaces. After incubation, microtiter plates were placed onto a magnetic field (Dexter magnetic technologies, cat. 54170260) for 4 minutes to bring magnetic particles, a fraction containing labelled cells, through the "dye-cushion" and into proximity to the imaging surface at the bottom of the wells.

Imaging of labeled cells: The MultiPath™ laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1 MP Sony IMX265 monochrome sensor with 12-bit per pixel quantization. The final image for each well is then formed by summing multiple frames. 16 frames were captured at a 100 msec exposure using 635/25 nm excitation and 680/40 nm emission filters. The focus particles are imaged at 470/40 nm excitation and 520/40 nm excitation filters and captured 2 frames at a 20 msec exposure.

Data analysis: At each cell concentration, the number of fluorescent objects detected was determined. The data from all eight cell concentrations was fit to a linear regression line, and the slope, intercept and standard deviation of the lowest 3 cell inputs was used to determine the limit of the blank (LoB) and limit of detection (LoD) for each bacterium tested.

Results

Figure 14:
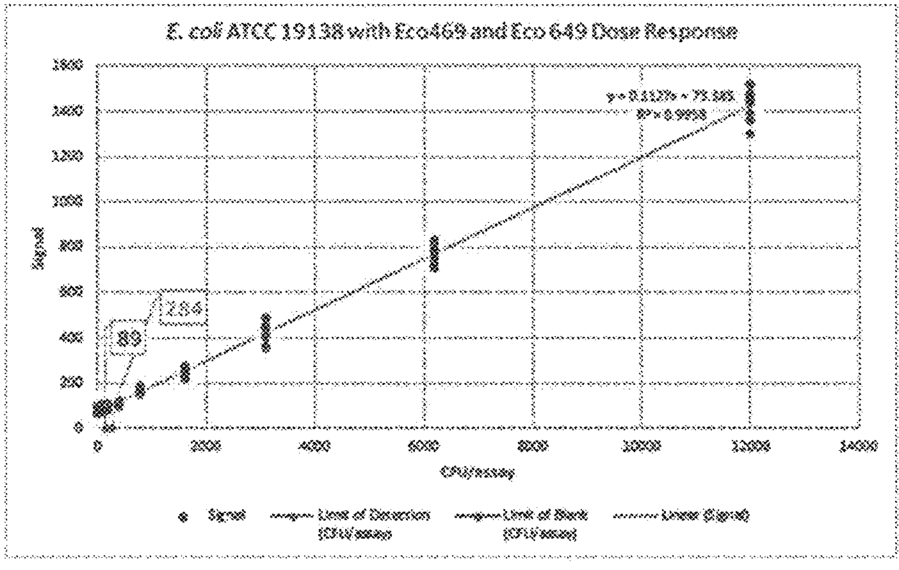
FIG. 14 shows Limit of detection (LoD) of *E. coli* ATCC 19138 is shown. Limit of blank (LoB) was 89 CFU/assay and the LoD was 284 CFU/assay. This corresponds to an LoD of 9,467 CFU/ml of urine.
Figure 15:
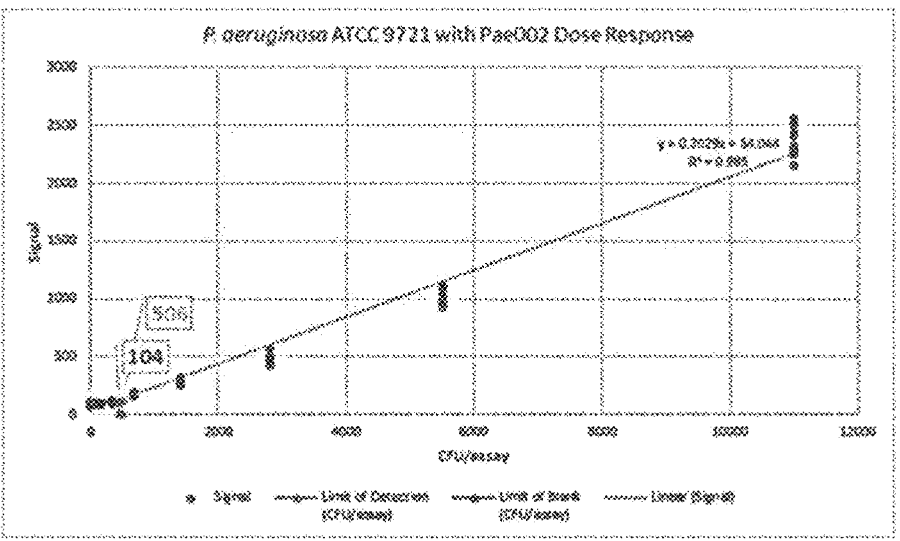
FIG. 15 shows Limit of detection (LoD) of *P. aeruginosa* ATCC 9721 is shown. Limit of blank (LoB) was 104 CFU/assay and the LoD was 506 CFU/assay. This corresponds to an LoD of 16,867 CFU/ml of urine.
Figure 16:
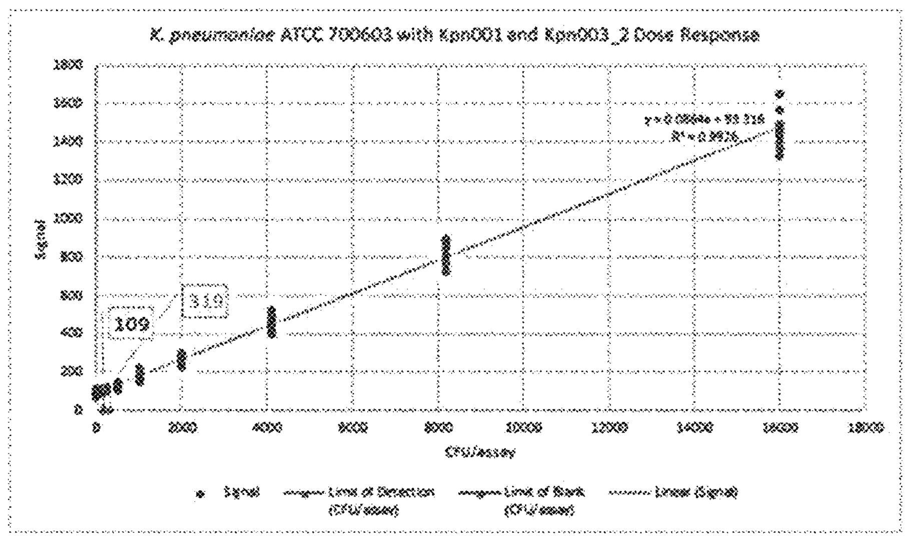
FIG. 16 shows Limit of detection (LoD) of *K. pneumoniae* ATCC 700603 is shown. Limit of blank (LoB) was 109 CFU/assay and the LoD was 319 CFU/assay. This corresponds to an LoD of 10,633 CFU/ml of urine.

All three bacteria tested showed low limits of detection. FIG. 14, FIG. 15, and FIG. 16 show the data generated for *E. coli, K. pneumoniae*, and *P. aeruginosa* with the linear fit used to calculate the LoB and LoD. The LoB and LoD are indicated in CFUs detectable in a single reaction well.

Conclusions. The novel and rapid FISH method described in this example is shown to be a sensitive method with limits of detection of about 500 CFU or less per reaction, using minimally processed urine matrix.

Variations. This example is illustrative of the performance of this novel FISH method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations), concentration of urine and urine processing procedures. This methodology can also clearly be extended to other biological specimens and to other bacterial and non-bacterial pathogens.

Example 2. Inclusivity: Detecting and Identifying Different Strains of a Bacterial Species Using the Inventive Rapid FISH Method Overview. This example demonstrates the use of the invention to detect different strains for a targeted bacterial species. Raw data for 11 different *E. coli* strains are presented and data for *K. pneumoniae, P. aeruginosa, P. mirabilis* and *Enterococcus* spp. are summarized. Bacterial cell targets were labeled in 30 minutes using isothermal fluorescence in situ hybridization (FISH) and detected on the MultiPath™ CCD-camera-based detection system.

Experimental Methods.

Bacterial cell preparation: Bacterial cultures for different strains were obtained by inoculating Trypticase Soy Broth (TSB, Hardy Diagnostics Cat. U65) with 3 to 5 colonies from fresh tryptic soy agar plates (TSA, BD cat. 221185) and growing for 1.5 to 3 hours at 35° C. to achieve log-phase growth. Using optical density at 600 nm to estimate cell concentration, cells were diluted to approximately 600 CFU and 3000 CFU per reaction in 1× cation-adjusted Mueller-Hinton broth (MHBII, Teknova cat. M5860). For more accurate percent cellular detection calculations, these estimated bacterial inputs were adjusted using colony counts. Plate counts were determined by diluting the log-phase cultures to about 500 CFU/mL in MHBII, plating 100 μL on TSA plates and counting colonies after growth at 35° C. for 16 to 24 hours.

Preparation of Magnetic Particles: Polyaspartic acid-conjugated magnetic particles used to non-specifically capture bacterial cells (Fluidmag-PAA, Chemicell, cat. 4108) were diluted 1:20 into 50 mM EPPS buffer, pH 8.2 to $2.75\times10^{12}$ particles/mL. Fluorescent magnetic microspheres containing a green dye (Dragon Green Fluorescent Microspheres, BANGS Laboratories, cat MEDG001) were added to the suspension at a final concentration of $3\times10^{6}$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below.

Labeling of Bacterial Cells: 100 μL labeling reactions were prepared by combining diluted cells, isothermal hybridization buffer (0.9×MHBII, 3×SSC (1.5M NaCl, 0.15M Sodium citrate, Sigma, cat. S6639), 0.77% w/v CHAPSO (Sigma cat. C3649), 0.72% w/v SB3-12 (Sigma cat. D0431), 0.13M Guanidine thiocyanate (Sigma cat. G9277), 0.18% w/v Cetrimide (Sigma cat. M7365)), species-specific Alexa647N-labelled DNA or LNA-containing DNA probes (Integrated DNA Technologies, IDT) targeted to the 16S or 23S bacterial rRNA, helper probes to facilitate effective hybridization (IDT) and 30 μL of pooled human urine (Innovative Research, cat. IRHUURE500ML). Probe sequences are shown in the Table in FIG. 21.

The urine was first processed through a Zeba 7K MWCO spin column (Thermo Fisher, Cat. 89893 or 89892 depending on urine volume) according to the manufacturer's instructions. 10 μL of the magnetic particle preparation was then added to this mixture. The final reaction mixture was transferred to a microtiter plate containing 50 μL (previously dried) "dye cushion" (50 mM TRIS pH 7.5 (Teknova cat. T1075), 7.5% v/v Optiprep (Sigma cat. D1556), 50 mg/mL Direct Black 19 (Orient cat. 191L) incubated at 35° C. for 30 minutes to allow for the simultaneous rehydration of the "dye cushion", labeling of bacterial cells, and binding of magnetic particles to bacterial cell surfaces. After incubation, microtiter plates were placed onto a magnetic field (Dexter magnetic technologies, cat. 54170260) for 4 minutes to bring magnetic particles, a fraction containing labelled cells, through the "dye cushion" and into proximity to the imaging surface at the bottom of the wells.

Imaging of labeled cells: Labeled bacterial cells on the MultiPath laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1 MP Sony IMX265 monochrome sensor with 12-bit per pixel quantization. The final image for each well is then formed by summing multiple frames. 16 frames were captured at a 100 msec exposure using 635/25 nm excitation and 680/40 nm emission filters. The focus particles are imaged at 470/40 nm excitation and 520/40 nm excitation filters and captured 2 frames at a 20 msec exposure.

Data analysis: For each bacterium, the number of fluorescent objects was determined (assay signal). A bacterial strain was considered detected if signal was detected above three standard deviations of the signal in the no cell condition.

Figure 18:
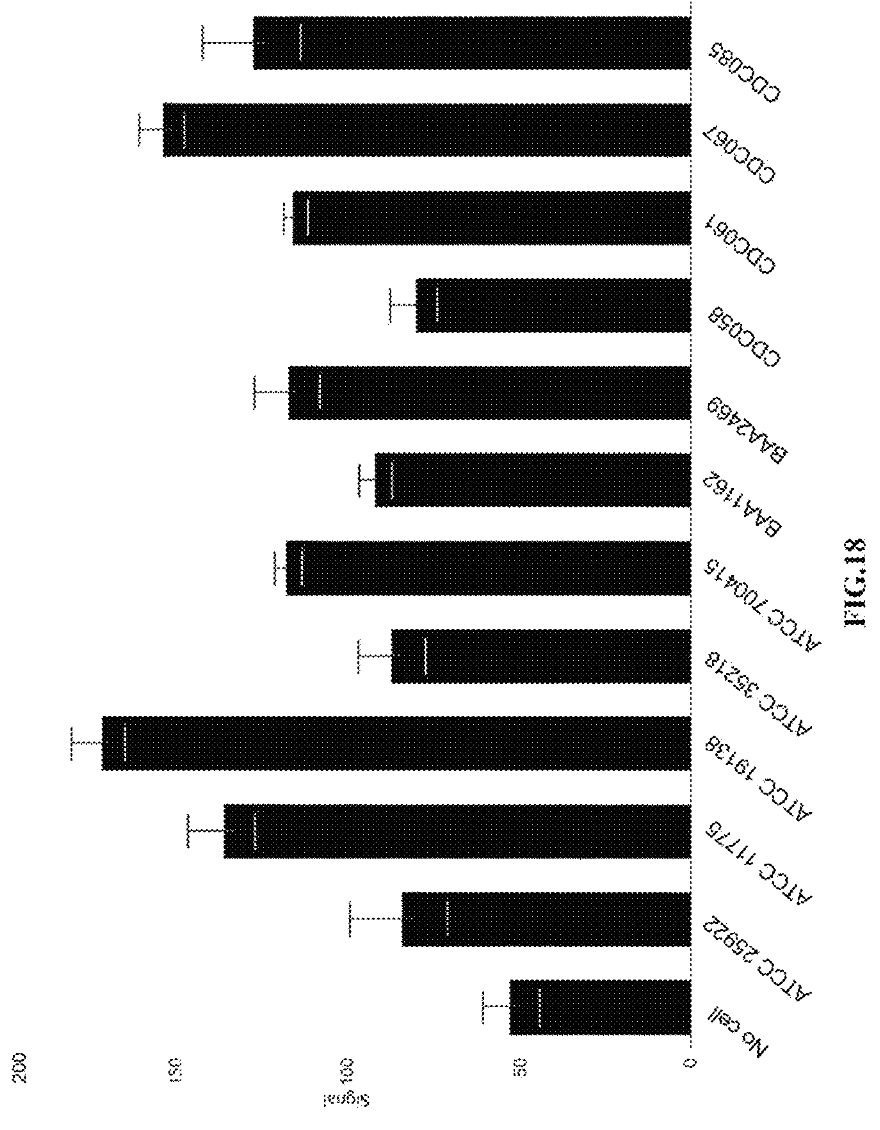
FIG. 18 shows Mean signal (n=3) is plotted for 11 *E. coli* strains for input cell concentrations of approximately 600 CFU/assay (light gray bars) and 3000 CFU/assay (dark gray bars). Signal derived from the no cell control (blank) is shown on left-hand side of the figure. Error bars represent 1 standard deviation.
Figures 19, 20:
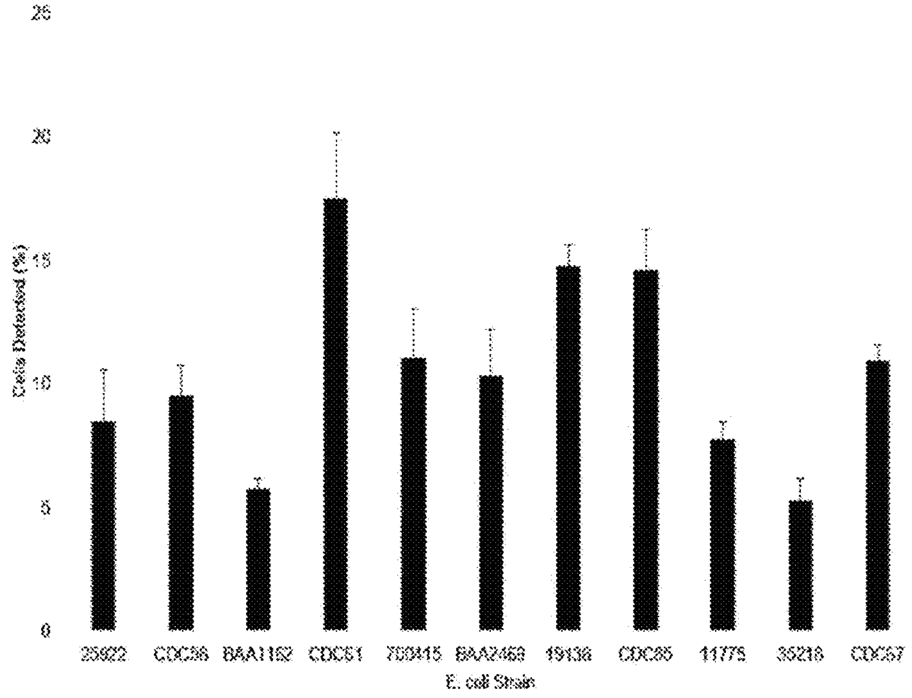
FIG. 19 shows the percentage of input cells (as determined by plate counts) that were detected are shown for each of the 11 *E. coli* strains. Each bar represents the mean of 6 determinations, 3 from each of the two different input cell levels. Percentage cell detection was calculated as [(assay signal−background signal)/input cells]*100.
FIG. 20 is a table giving Inclusivity results for 4 additional bacteria.

Results. FIG. 18 shows assay signal for 11 *E. coli* strains. All 11 strains were detected above the background "no cell" condition for at a cell input of approximately 600 CFU per assay. FIG. 19 shows the data represented as percentage of cells detected (total assay signal in cell input well−background assay signal/total cell input*100). Although the detection efficiency is somewhat variable from strain to strain, this did not inhibit the assay's ability to detect each of the 11 different *E. coli* strains.

The table in FIG. 20 summarizes inclusivity results for *E. coli, K. pneumoniae, P. aeruginosa, P. mirabilis* and *Enterococcus* spp. which were analyzed in the same manner as *E. coli*. Strains tested for *K. pneumoniae* were ATCC 13833, CDC80, CDC44, CDC87, CDC47, CDC43, BAA2470, CDC34, CDC39, ATCC 700603 and BAA-2472. Strains tested for *P. aeruginosa* were CDC263, CDC242, 9721, CDC236, 27853, BAA-2110, CDC233, 15692, CDC234, CDC246 and CDC261. Strains tested for *P. mirabilis* were CDC155, CDC29, CDC159, CDC59, ATCC 7002 and CDC156. Strains tested for *Enterococcus* included ATCC 19433, ATCC 29212, ATCC 33186, ATCC 51575, ATCC 51299 and BAA-2128.

Conclusions. The novel FISH method described in this example detected all strains tested for 5 different bacterial species that are among the major pathogens leading to clinical symptoms in patients with UTI.

Variations. This example is illustrative of the performance of this novel FISH method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations), concentration of urine and urine processing procedures. This methodology can also clearly be extended to other biological specimens and to other bacterial and non-bacterial pathogens.

Example 3. Specific Detection of Target Bacteria Using Rapid Isothermal FISH Overview. This example demonstrates that the novel isothermal FISH method specifically detects a target bacterium while not detecting related non-target bacteria, even at very high concentrations. This example presents assay conditions that specifically detect *E. coli* yet do not detect 16 other bacteria that also cause urinary tract infections (UTI), have similar rRNA sequences or are commensal organisms.

Experimental Methods

Bacterial cell preparation: Bacterial cultures for 16 off-target bacteria (listed in Table 1) and *E. coli* strain ATCC 25922 were grown from a single colony selected from a fresh tryptic soy agar plates (TSA, BD cat. 221185), inoculated into Trypticase Soy Broth (TSB, Hardy Diagnostics cat. U65) and grown with shaking overnight at 35° C. 50-80 μL of the overnight culture was added into fresh TSB and grown for 1.5-2 hours, until the optical density at 600 nm reached 0.15-0.3. Each bacterium was then diluted to approximately $1\times10^8$ cells per mL in cation-adjusted Mueller Hinton (MHBII, Teknova cat. M5860).

Selection of bacterial targets to evaluate: Bacterial pathogens to test for specificity were selected for their rRNA sequence similarity to the target bacteria's rRNA sequence or because they are pathogens that are commonly found in urinary tract infections (the disease target) and therefore, cross-reactivity to these organisms would be most problematic. The table in FIG. 22 shows the bacterial species and strains tested.

Preparation of FISH probes: A DNA probe set for *E. coli* was heated in a water bath between 80-85° C. for 10 minutes and then placed on ice to reduce aggregation. This DNA probe set is shown in Table in FIG. 23. The set contains a species-specific DNA oligonucleotide labeled with a fluorescent dye (Alexa647N, Thermo Fischer) and helper oligonucleotides that bind adjacent or near the specific probe and are designed to disrupt the local secondary structure of the ribosomal subunit, and allow the labeled, specific probe greater hybridization efficiency to the target rRNA.

Preparation of Magnetic Particles: Polyaspartic acid-conjugated magnetic particles used to non-specifically capture bacterial cells (Fluidmag-PAA, Chemicell, cat. 4108) were diluted 1:20 into 50 mM EPPS buffer, pH 8.2 to $2.75\times10^{12}$ particles/mL. Fluorescent magnetic microspheres containing a green dye (Dragon Green Fluorescent Microspheres, BANGS Laboratories, cat MEDG001) were added to the suspension at a final concentration of $3\times10^6$ particles/mL. These particles enable the optical system to focus on the correct plane. The magnetic particle mixture was sonicated for 1 minute immediately prior to use to minimize aggregation.

Labeling of Bacterial Cells: 100 μL labeling reactions were prepared by combining diluted cells, isothermal hybridization buffer (0.9×MHBII (Teknova cat. M5860), 3×SSC (0.45M NaCl, 0.045M Sodium citrate, Sigma, cat. cat. S6639), 0.77% w/v CHAPSO (Sigma cat. C3649), 0.72% w/v SB3-12 (Sigma cat. D0431), 0.13M Guanidine thiocyanate (Sigma cat. G9277), 0.18% w/v Cetrimide (Sigma cat. M7365)), species-specific Alexa647N-labelled probes (Integrated DNA Technologies, IDT) targeted to the 16S or 23S bacterial rRNA, helper probes to facilitate effective hybridization (IDT) and 30 μL of pooled human urine (Innovative Research, cat. IRHUURE500ML). The specific probe sets tested are shown in Table in FIG. 23. The urine was first processed through a Zeba 7K MWCO spin column (Thermo Fisher, Cat. 89893 or 89892 depending on urine volume) according to the manufacturer's instructions. 10 μL of the magnetic particle preparation was then added to this mixture. The final reaction mixture was transferred to a microtiter plate containing 50 μL per well (previously dried) of "dye-cushion" (50 mM TRIS pH 7.5 (Sigma cat. T1075), 7.5% v/v Optiprep (Sigma cat. D1556), 50 mg/mL Direct Black 19 (Orient cat. 191L)) and incubated at 35° C. for 30 minutes to allow for the simultaneous rehydration of the "dye-cushion", labeling of bacterial cells, and binding of magnetic particles to bacterial cell surfaces. Each bacterium was tested at a final concentration of $1\times10^6$ cells per reaction. This concentration is around 3000-fold higher than the determined limit of detection for *E. coli*. After incubation, microtiter plates were placed onto a magnetic field (Dexter magnetic technologies, cat. 54170260) for 4 minutes to bring magnetic particles, a fraction containing labelled cells, through the "dye-cushion" and into proximity to the imaging surface at the bottom of the wells.

Imaging of labeled cells: The MultiPath™ laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1 MP Sony IMX265 monochrome sensor with 12-bit per pixel quantization. The final image for each well is then formed by summing multiple frames. 16 frames were captured at a 100 msec exposure using 635/25 nm excitation and 680/40 nm emission filters. The focus particles are imaged at 470/40 nm excitation and 520/40 nm excitation filters and captured 2 frames at a 20 msec exposure.

Data analysis: For each bacterium, the number of fluorescent objects was determined (assay signal). A bacterium was considered cross-reactive if signal was detected within three standard deviations of the signal in the blank (no bacteria added).

Results

Figure 24:
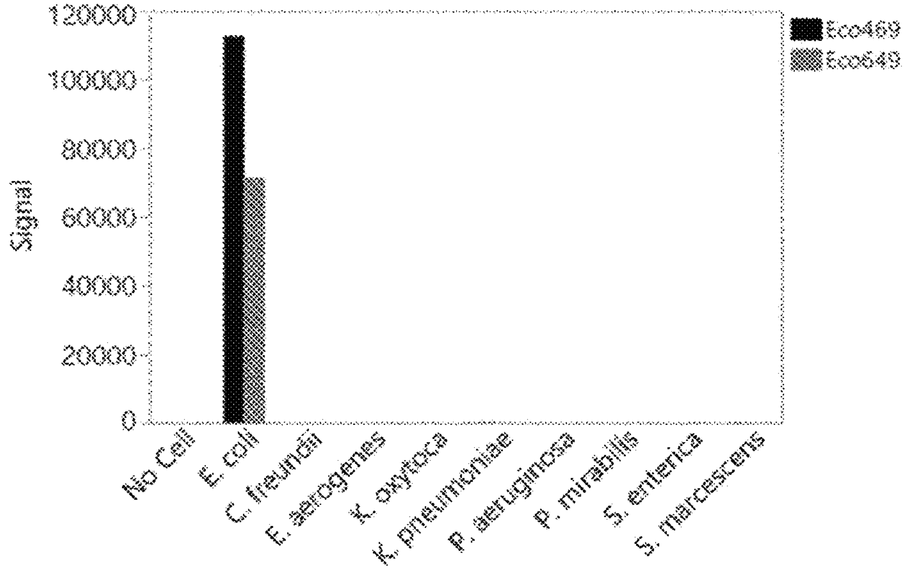
FIG. 24 shows Specific detection of *E. coli* and no detection of 8 challenge bacteria
Figure 25:
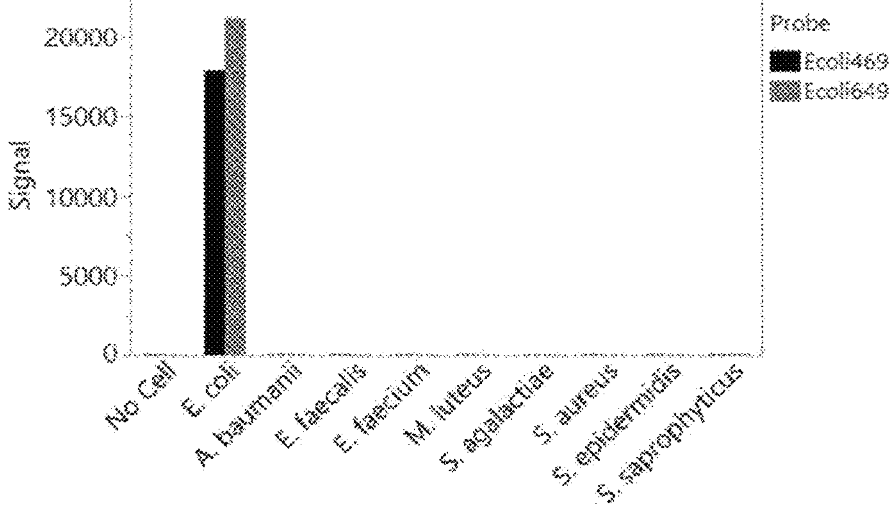
FIG. 25 shows Specific detection of *E. coli* and no detection of 8 additional challenge bacteria

FIG. 24 and FIG. 25 show the rapid novel FISH method only detects *E. coli* and not the other 16 different challenge bacteria. FIG. 24 and FIG. 25 each show that very high concentrations ($1\times10^6$ cells per reaction) of 8 clinically relevant challenge bacteria are not detected under the same assay conditions that generate high assay signal for the *E. coli* targeted bacteria. The two bars represent two different probe sets designed to be specific for *E. coli* (see Table in FIG. 23). The assay signal for each of the 16 challenge bacteria was less than the no-cell control plus three standard deviations (125).

Conclusions. The novel rapid FISH method described in this example specifically, by design, detects *E. coli* but does not detect 16 clinically relevant potential cross-reactive bacteria. This demonstrates the method has high specificity for the identification of a target UTI pathogen which is of critical importance for the clinical treatment of the infection.

Variations. This example is illustrative of the performance of this novel FISH method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations), concentration of urine and urine processing procedures. This methodology can also clearly be extended to other biological specimens and to other bacterial and non-bacterial pathogens. Assays have also been designed that demonstrate high specificity for *K. pneumoniae, K. oxytoca, P. aeruginosa, P. mirabilis* and *E. faecalis.*

Example 4. A Multiplexed FISH Method that Simultaneously Identifies 4 Distinct Microbes Overview. This example demonstrates the use of the invention to simultaneously detect, in a single reaction, *E. coli, K. pneumoniae, P. aeruginosa*, and *K. oxytoca* using fluorescently labeled probes specific for each bacteria's rRNA. Each pathogen was specifically detected in the mixture through the use of 4 distinct fluorophores—one for each bacterial species—that have different excitation/emission spectral properties.

Experimental Method. Bacterial cell growth: Bacterial cultures for *Escherichia coli* ATCC 25922, *Klebsiella pneumoniae* ATCC 13883, *Pseudomonas aeruginosa* ATCC 27853, and *Klebsiella oxytoca* ATCC 8724 were obtained by inoculating Trypticase Soy Broth (TSB, Hardy Diagnostics cat. U65) with 3 to 5 colonies from fresh tryptic soy agar plates (TSA, BD cat. 221185) and growing for 1.5 to 3 hours at 37° C. to achieve log-phase growth. Each culture was then diluted in cation-adjusted Mueller-Hinton Broth (MHBII, Teknova, cat. M5860) to an optical density at 600 nm of 0.15, which is approximately $1.0\times10^8$ colony-forming units (CFUs) per mL.

Preparation of Magnetic Particles: Polyaspartic acid-conjugated magnetic particles (Fluidmag-PAA, Chemicell, cat. 4108) and carboxyl-coated magnetic particles (Carboxyl Magnetic Particles, Spherotech, cat. CM-025-10H) were used to non-specifically capture bacterial cells. Each particle was diluted 1:40 into 50 mM Epps buffer, pH 8.2, with final concentrations of approximately $1.38\times10^9$ particles per reaction for the polyaspartic acid particles and $3.46\times10^9$ for the carboxyl particles.

Labeling of Bacterial Cells: 100 μL labeling reactions were prepared by combining diluted cells of all four bacteria, isothermal hybridization buffer (0.9×MHBII, 3×SSC (1.5M NaCl, 0.15M Sodium citrate, Sigma, cat. S6639), 0.77% w/v CHAPSO (Sigma cat. C3649), 0.72% w/v SB3-12 (Sigma cat. D0431), 0.13M Guanidine thiocyanate (Sigma cat. G9277), 0.18% w/v Cetrimide (Sigma cat. M7365)), species-specific DNA probes (Integrated DNA Technologies, IDT) targeted to the 16S or 23S bacterial rRNA, helper probes to facilitate effective hybridization (IDT) and 30 μL of pooled human urine (Innovative Research, cat. IRHUURE500ML). 10 μL of the magnetic particle preparation was then added to this mixture. Probe sequences and the location of their dye modifications are shown in Table in FIG. 27.

The cells/hybridization mixture (1 mL) was transferred into the cartridge. The cartridge was placed onto the analyzer (as described below) which automated the remaining assay steps and image acquisition and analysis. Briefly, the fluidic system of the analyzer moved the reaction mixture into the optical window containing 46 μL per well (previously dried) of "dye-cushion" (50 mM TRIS pH 7.5 (Sigma cat. T1075), 7.5% v/v Optiprep (Sigma cat. D1556), 50 mg/mL Direct Black 19 (Orient cat. 191L). The cartridge was incubated within the analyzer at 35° C. for 30 minutes. Following this incubation, the cartridge was moved for 4 minutes onto the magnet station (Dexter magnetic technologies, cat. 54170260) to bring magnetic particles, a fraction containing labeled cells, through the rehydrated "dye-cushion" and into proximity to the imaging surface at the bottom of the wells. After the magnet station, the cartridge was moved to the imaging station within the analyzer and a series of images taken in each of the four color channels (red (excitation 635/25 nm, emission 680/40 nm), yellow (excitation 530/20 nm, emission 572/23 nm), green (excitation 470/40 nm, emission 520/40 nm), orange (excitation 569/25 nm, emission 609/34 nm)).

Imaging of labeled cells: The MultiPath Analyzer imaging system is a custom-built instrument and software that is capable of automatically capturing image data from selected wells of a MultiPath Cartridge as part of a fully automated test. It uses a custom designed precision 3 axis positioning system to locate each well over a fluorescence-based image acquisition subsystem. The Analyzer can image in 4 separate color channels and uses an objective lens, illumination LEDs, fluorescent filter sets, and camera. The objective lens has a field of view designed to capture the image of an entire Cartridge Imaging Well. The illumination module light source consists of 2 high power LEDs per color channel. A series of fluorescent image frames are captured with a camera using a 3.1 MP Sony IMX265 monochrome sensor with 12-bit per pixel quantization. The final image for each well is then formed by summing multiple frames. For the red channel, 16 frames were captured at a 100 msec exposure using 635/25 nm excitation and 680/40 nm emission filters. For the orange channel, 24 frames were captured at a 100 msec exposure using 569/25 nm excitation and 609/34 nm emission filters. For the Yellow channel, 48 frames were captured at a 100 msec exposure using 530/20 nm excitation and 572/23 nm emission filters. For the Green channel, 32 frames were captured at a 100 msec exposure using 470/40 nm excitation and 520/40 nm emission filters. The focusing plane for imaging the labeled cells was determined experimentally in this example.

Figure 26:
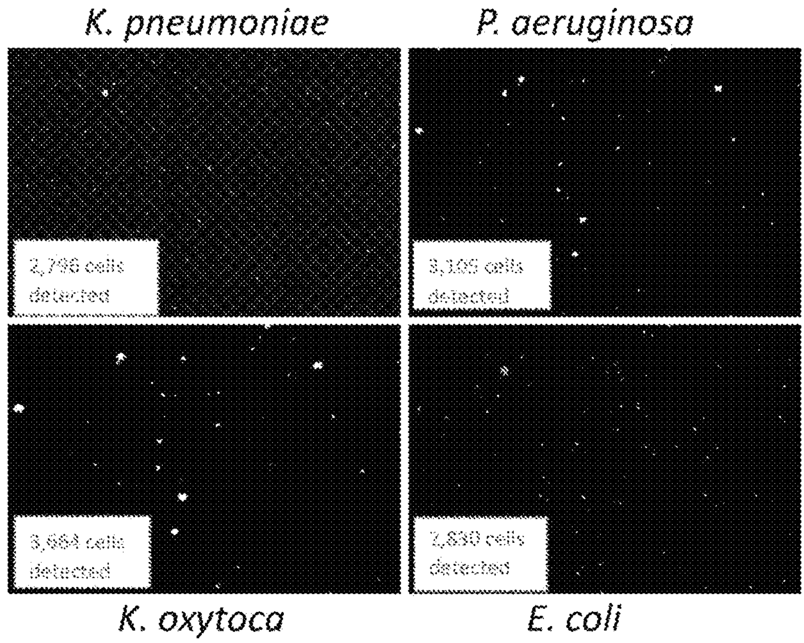
FIG. 26 is Images showing the same field of view taken in 4 different color channels using the CCD imaging method and 4 different fluorophores, one for each bacterium. All four bacteria could be detected in a single well.

Results. FIG. 26 shows a portion of the full acquired image in which the fluorescence was detected in each of the 4 color channels, each specific for one of the 4 input bacteria. Each spot corresponds to a single cell or group of cells. An algorithm is used to identify meaningful objects distinct from artifacts (e.g. debris) and counts those objects as cells. As seen in the inserts for each bacterium, a similar number of cells were detected as expected since the input cell concentrations were approximately the same. When overlaid, these spots do not correspond, indicating that different objects were observed in each channel, as expected with 4 different bacterial targets.

Conclusions. This method allows for a single rapid FISH method to simultaneous detect and quantify four different bacteria in a single well of a cartridge.

Variations

This example is illustrative of the multiplex capability of this novel FISH method and is not limited to the specific details included in the description. One skilled in the art will readily understand that many variations are therefore possible, including using different probe sequences and nucleic acid structures (PNA, LNA, etc.) and alternative assay chemistries (different detergents, chaotropes, fluorophores, buffers, pH, temperatures, reaction times, component concentrations). This methodology can also clearly be extended to other biological specimens and to other bacterial and non-bacterial pathogens for which specific probes can be designed.

Example 6. Automated Rapid AST of *E. coli* in Clinical Urine Specimens in a Cartridge on an Instrument Overview: This example demonstrates the use of the systems, devices, and methods of invention to determine the antimicrobial susceptibility of a targeted bacterial pathogen (*E. coli* in this example) in urine in 4 hours without requiring cell purification. The example using a concerted FISH method for labeling and magnetic selection and quantifies specific target cells after differential growth using non-magnified digital imaging. This new method has comparable performance to the gold standard CLSI broth microdilution (BMD) method.

Experimental Methods

Urine Specimens: 48 remnant de-identified urine specimens collected from patients with a urinary tract infection (UTI) and known to contain *E. coli* were received from Dr. Kirby's lab at Beth Israel Hospital (Boston, MA). Samples were received 1-5 days post collection and contained a urine preservative to limit loss of cell viability. For each sample, color of urine, pH, and presence of particulates were noted. Upon receipt, conventional urine culture was performed to determine the approximate CFU/mL of bacteria present, and to confirm single or mixed bacterial morphology as reported by Dr. Kirby's lab. Briefly, a calibrated 1 μL loop was placed into a well-mixed urine sample and the 1 μL was evenly spread over a Tryptic soy agar (TSA, BD cat. 221185) plate and incubated in a 35° C. incubator for 18-24 hours. The remainder of the urine samples were processed and assayed as described below.

Urine Processing: Prior to testing, urine preservative and other potentially interfering compounds were removed using size exclusion chromatography. 2.5 mL of each clinically positive urine sample was applied to a pre-washed Zeba™ 7K MWCO spin column (ThermoFisher, cat. #89893) and centrifuged according to the manufacturer's instructions. Urine culture was repeated on this processed sample as described above, to examine bacterial loss following processing.

Preparation of Magnetic Particles: Polyaspartic acid-conjugated magnetic particles used to non-specifically capture bacterial cells (Fluidmag-PAA, Chemicell, cat. 4108) were diluted 1:20 into 50 mM EPPS buffer, pH 8.2 to $2.75\times10^{12}$ particles/mL. Fluorescent magnetic microspheres containing a green dye (Dragon Green Fluorescent Microspheres, BANGS Laboratories, cat MEDG001) were added to the suspension at a final concentration of $3\times10^{6}$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below.

Bacterial Cell Labeling at AST Time Zero: Assay signal at time zero (T0) prior to the initiation of bacterial growth in the presence or absence of antibiotics was determined for each clinical urine specimen. 30 μL of each processed urine was added to 70 μL of 1× cation-adjusted Mueller-Hinton Broth (MHBII) containing species-specific Alexa647N-labeled DNA oligonucleotide FISH probes and unlabeled DNA helper probes. Probe sequences used are shown in Table A. The 100 μL mixture was then added to a well of a microtiter plate containing dehydrated hybridization buffer (3×SSC (0.45 M NaCl, 0.045 M Na citrate) buffer (Sigma, cat. #S6639), 0.18% cetrimide (Sigma, cat. #H9151), 0.77% CHAPSO (Sigma cat. #C3649), 0.72% SB3-12 (Sigma cat. #D0431) 0.13M guanidine thiocyanate (Sigma, cat. #G9277)). 104, of the prepared magnetic particle mixture was then added to the well. 100 μL of this reaction mixture was transferred to a microtiter plate containing 50 μL per well (previously dried) of "dye-cushion" (50 mM TRIS pH 7.5 (Sigma cat. T1075), 7.5% v/v Optiprep (Sigma cat. D1556), 50 mg/mL Direct Black 19 (Orient cat. 191L) and incubated at 35° C. for 30 minutes. After incubation, microtiter plates were placed onto a magnetic field (Dexter magnetic technologies, cat. 54170260) for 4 minutes to bring magnetic particles, a fraction containing labeled cells, through the "dye-cushion" and into proximity to the imaging surface at the bottom of the wells.

Imaging of labeled cells: The MultiPath™ laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1 MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Preparation of Antibiotic Plates: Microtiter plates containing six concentrations of each antibiotic in a 2-fold serial dilution series were prepared, starting at a 10-fold higher concentration than the expected minimum inhibitory concentration (MIC). Antibiotics used were Cefazolin, Ciprofloxacin, Nitrofurantoin, and Trimethoprim-Sulfamethoxazole. Antibiotic dilutions were verified to be within the appropriate tolerance by confirming that the MIC for at least two CLSI QC strains fell within the QC range reported in CLSI document M100Ed29E-2019. The concentrations selected for testing of each antibiotic straddled the CLSI-reported breakpoints for the antibiotic for *E. coli*. In addition to the wells containing the antimicrobial dilution series, eight wells containing water or diluent were included in the plates to allow for a no antibiotic positive and negative growth control.

Four Hour Growth: While the time zero cell quantification was occurring, 32.4 μL of processed clinical urine and 75.6 μL of 1.43×MHB II (Teknova, cat. #M5860) was added to each well of the antibiotic plate (already containing 12 μL of antibiotics). The samples were allowed to grow in a standard incubator at 35° C. for 4 hours.

Bacterial Cell Labeling at AST time four-hour growth: After samples had incubated in the presence and absence of antibiotics for four hours (T4), cells were labeled and quantified to determine how much growth, if any, occurred. 100 μL of each well of the incubated sample-antibiotic plate was transferred to a corresponding well of a dehydrated buffer plate and combined with FISH probes, helper probes, magnetic particles, and focus particles in the same manner as described above for assay time zero.

Comparison Method: Results for the MulitPath™ Assay were compared to broth microdilutions (BMD) performed according to the CLSI method M07-Ed13E 2018.

Data Analysis and Threshold Generation: Using the image captured by the CCD camera, detected cells were estimated by an algorithm that looked at both number of objects in the field of view and the intensity of the objects. Number of cells based on this detection algorithm were generated at time zero, and at time four hours without antibiotic and with all 6 concentrations of each antibiotic. For each urine sample/drug concentration, fold growth was calculated as the signal in the well containing antibiotic after growth (time four) to the signal in the urine sample prior to growth (time zero). Using fold growth and the observation of growth in the corresponding well in the CLSI-compliant broth microdilution, a logistic regression model was used to generate thresholds for determining the fold growth cutoff above which cells are growing in the presence of the antibiotic (and thus, resistant at that concentration) and below which, cells are in the process of dying (and thus, sensitive at that concentration). The point where the fold growth number falls below the determined threshold is the MIC value generated by the assay. Results were correspondingly assigned to categories of susceptible, intermediate, or resistant to each antibiotic. All data was then compared to CLSI standard BMD. Four-hour growth in the absence of antibiotic is a control condition to ensure viable bacterial are present in the processed urine sample.

Results

Figure 28:
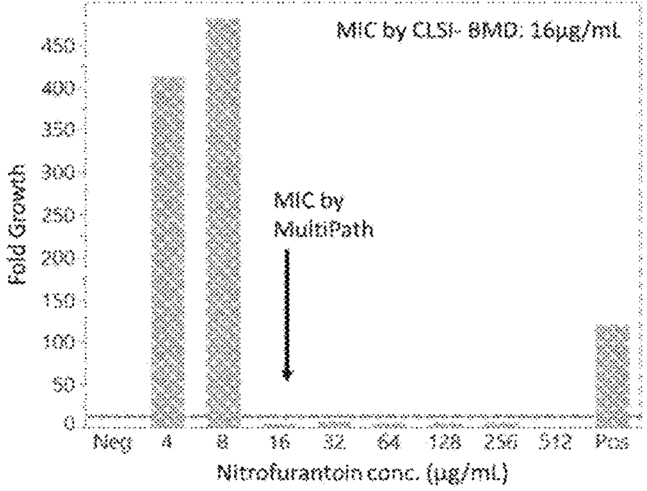
FIG. 28 shows BIUR0017 with Nitrofurantoin
Figure 29:
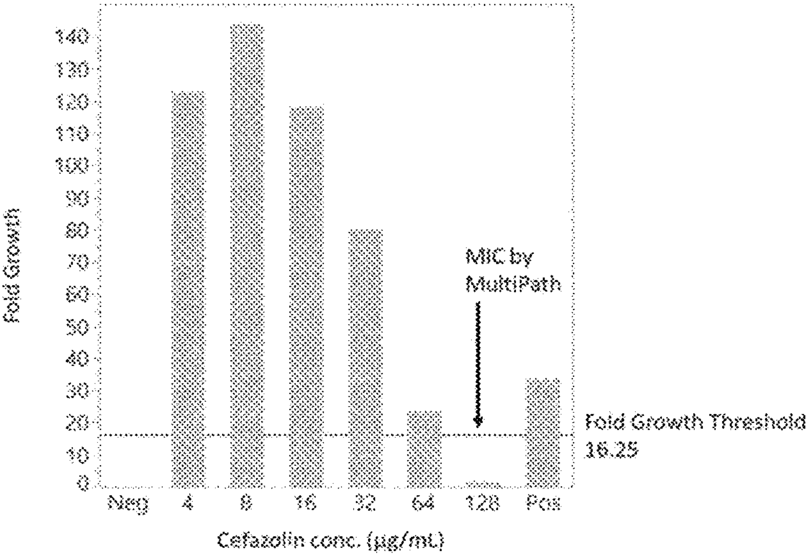
FIG. 29 shows BIUR047 with Cefazolin
Figure 30:
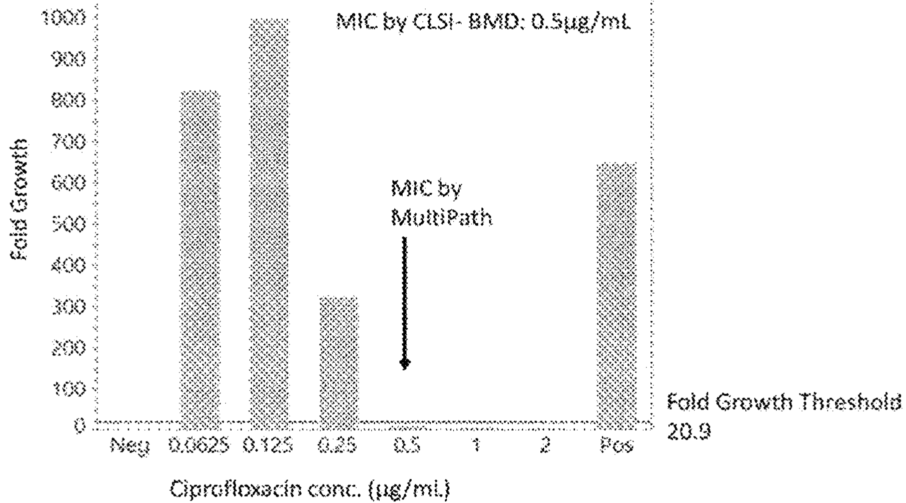
FIG. 30 shows BIUR057 with Ciprofloxacin
Figure 31:
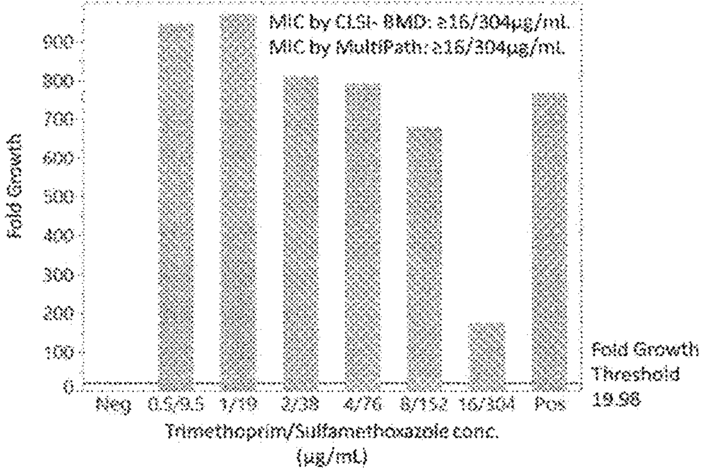
FIG. 31 shows BIUR052 with Trimethoprim/Sulfamethoxazole

FIG. 28 through FIG. 31 shows three examples from our larger data set that demonstrate how this method can be used to generate MICs on three individual urines that match the gold-standard broth microdilution method. FIG. 28 shows the fold growth numbers at different antibiotic concentrations results for a single clinical urine sample (BIUR0017) against a single drug (Nitrofurantoin). The MIC for the broth microdilution matches exactly with the MIC determined by the fold-growth threshold. FIG. 29 shows the fold growth numbers at different antibiotic concentrations results for a single clinical urine sample (BIUR0047) against a single drug (Cefazolin). The MIC for the broth microdilution matches exactly with the MIC determined by the fold-growth threshold. FIG. 30 shows the fold growth numbers at different antibiotic concentrations results for a single clinical urine sample (BIUR0057) against a single drug (Ciprofloxacin). The MIC for the broth microdilution matches exactly with the MIC determined by the fold-growth threshold. FIG. 31 shows the fold growth numbers at different antibiotic concentrations results for a single clinical urine sample (BIUR0052) against a single drug (Trimethoprim/Sulfmethoxazole). The MIC for the broth microdilution matches exactly with the MIC determined by the fold-growth threshold.

Conclusions. This novel method shows that accurate AST results (MIC determinations) may be made with only 4 hours of differential growth of minimally processed urine clinical specimens, notably without lengthy colony purification steps. The AST results, whether reported as MIC categorical antibiotic susceptibility results, compare favorably to the gold standard, broth microdilution method.

Variations. This example is illustrative of the performance of this novel AST method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations, etc.), concentration of urine and urine processing procedures. This methodology can also clearly be extended to other antibiotics, biological specimens and to other bacterial and non-bacterial pathogens.

Example 7. Rapid and Accurate Antimicrobial Susceptibility Testing for Bacteria in Urine Samples Overview. This example demonstrates the use of the invention to accurately determine the antimicrobial susceptibility of pathogens with known antibiotic susceptibility profiles added into bacteria-free urine. Differential growth in microbiological media containing antimicrobial agents followed by assessment of growth using the inventive concerted FISH method for target specific cell quantification required just 4.5 hours. This new method has comparable performance to the gold standard CLSI broth microdilution (BMD) method.

Experimental Methods

Bacterial cell preparation: 50 bacterial strains with known resistance profiles were collected from either the ATCC or from the CDC antibiotic resistance bank (AR bank) and are shown in Table A. Bacterial cultures for each of these were obtained by inoculating Trypticase Soy Broth (TSB, Hardy Diagnostics cat. U65) with 3 to 5 colonies from fresh tryptic soy agar plates (TSA, BD cat. 221185) and growing for 1.5 to 3 hours at 35° C. to achieve log-phase growth. Using optical density at 600 nm to estimate cell concentration, each culture was diluted to approximately $5\times10^6$ colony-forming units (CFU)/mL in cation-adjusted Mueller Hinton II (MHBII, Teknova cat. M5860).

Urine Processing: Prior to testing, pooled human urine (Innovative Research, cat. IRHUURE500ML) was applied to a pre-washed Zeba™ 7K MWCO spin column in a ratio of 4 mL urine to one pre-washed 10 mL spin column (ThermoFisher, cat. #89893) and centrifuged according to the manufacturer's instructions.

Preparation of Magnetic Particles: Polyaspartic acid-conjugated magnetic particles used to non-specifically capture bacterial cells (Fluidmag-PAA, Chemicell, cat. 4108) were diluted 1:20 into 50 mM EPPS buffer, pH 8.2 to $2.75\times10^{12}$ particles/mL. Fluorescent magnetic microspheres containing a green dye (Dragon Green Fluorescent Microspheres, BANGS Laboratories, cat MEDG001) were added to the suspension at a final concentration of $3\times10^6$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below.

Bacterial Cell Labeling at AST Time Zero: Assay signal at time zero (T0) prior to the initiation of bacterial growth in the presence or absence of antibiotics was determined for each bacterium. A reaction mixture was prepared consisting of 30 μL processed urine, 10 μL of the $5\times10^6$ CFU/mL bacterial dilution, 60 μL MHBII (1× final concentration in 100 μL) and the appropriate species-specific Alexa647N-labeled DNA oligonucleotide FISH probe and its associated unlabeled DNA helper probes for the target bacterial species. Probe sequences used are shown in Table in FIG. 36. The 100 μL mixture was then added to a well of a microtiter plate containing dehydrated hybridization buffer (3×SSC (0.45 M NaCl, 0.045 M Na citrate) buffer (Sigma, cat. #S6639), 0.18% cetrimide (Sigma, cat. #H9151), 0.77% CHAPSO (Sigma cat. #C3649), 0.72% SB3-12 (Sigma cat. #D0431), 0.13M guanidine thiocyanate (Sigma, cat. #G9277)). 10 μL of the prepared magnetic particle mixture was then added to the well. 100 μL of this reaction mixture was transferred to a microtiter plate containing 50 μL per well (previously dried) of "dye-cushion" (50 mM TRIS pH 7.5 (Sigma cat. T1075), 7.5% v/v Optiprep (Sigma cat. D1556), 50 mg/mL Direct Black 19 (Orient cat. 191L) and incubated at 35° C. for 30 minutes. After incubation, microtiter plates were placed onto a magnetic field (Dexter magnetic technologies, cat. 54170260) for 4 minutes to bring magnetic particles, a fraction containing labeled cells, through the "dye cushion" and into proximity to the imaging surface at the bottom of the wells.

Imaging of labeled cells: The MultiPath laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1 MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Preparation of Antibiotic Plates: Microtiter plates containing six concentrations of each antibiotic in a 2-fold serial dilution series were prepared. The 2-fold dilution series was prepared at a 10-fold higher concentration than the desired concentration in the final broth microdilution, such that addition cells/urine/media mixture would yield the correct antibiotic range. 12 uL of each antibiotic dilution was then aliquoted into the appropriate wells of a 96 well plate. Different antibiotics were tested for different bacteria. Antibiotic dilutions were verified to be within the appropriate tolerance by confirming that the MIC for at least two CLSI QC strains fell within the QC range reported in CLSI document M100Ed29E-2019. The concentrations selected for testing of each antibiotic straddled the CLSI-reported breakpoints for the antibiotic for the appropriate bacterial species such that categorical determinations (sensitive/intermediate/resistant) could be made from this data. In addition to the wells containing the antimicrobial dilution series, several wells containing water or other diluent were included for a no antibiotic positive growth and negative growth (no cell) control. Antibiotic plates were frozen at −80° C. and thawed completely before use.

Four Hour Growth: While the time zero cell quantification was occurring, 12 μL of prepared bacterial culture, 36 uL pooled human urine processed as done for the assay time zero, 60 uL of 2×MHB II (Teknova, cat. #M5860) and 2 uL water was added to each well of the prepared antibiotic plate. The samples were allowed to grow in a standard incubator at 35° C. for 4 hours.

Bacterial Cell Labeling at AST time four-hour growth: After samples had incubated in the presence and absence of antibiotics for four hours (T4), cells were labeled and quantified to determine how much growth, if any, occurred. 100 μL of each well of the incubated sample-antibiotic plate was transferred to a corresponding well of a dehydrated buffer plate and combined with FISH probes, helper probes, magnetic particles, and focus particles in the same manner as described above for assay time zero.

Comparison Method: Results for the MulitPath™ Assay were compared to broth microdilutions (BMD) performed according to the CLSI method M07-Ed13E 2018.

Data Analysis and Threshold Generation: Using the image captured by the CCD camera, detected cells were estimated by an algorithm that looked at both number of objects in the field of view and the intensity of the objects. Number of cells based on this detection algorithm were generated at time zero, and at time four hours without antibiotic and with all concentrations of each antibiotic. For each bacteria sample/drug concentration, fold growth was calculated as the signal in the well containing antibiotic after growth (time four) to the signal in the urine sample prior to growth (time zero). Using fold growth and the observation of growth in the corresponding well in the CLSI-compliant broth microdilution, a logistic regression model was used to generate thresholds for determining the fold growth cutoff above which cells are growing in the presence of the antibiotic (and thus, resistant at that concentration) and below which, cells are in the process of dying (and thus, sensitive at that concentration). The point where the fold growth number falls below the determined threshold is the MIC value generated by the assay. Results were correspondingly assigned to categories of susceptible, intermediate, or resistant to each antibiotic. Results were then compared to the MIC values and categorical calls reported by ATCC or the CDC. Four-hour growth in the absence of antibiotic is a control condition to ensure viable bacterium were added to each sample or for use when calculating fold inhibition.

Figure 33:
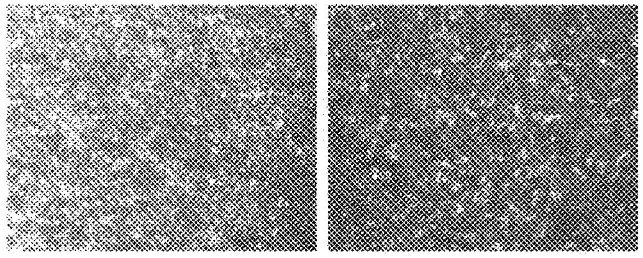
FIG. 33 is a Visual comparison of normal bacteria (left panel) to filamentous bacteria (right panel).

In addition, for the bacteria tested against Ceftazidime (CAZ), the presence of exclusively filamentous bacteria (as can be easily distinguished by eye, FIG. 33, compare left (normal bacteria) to right (filamentous bacteria)) was taken as an indication of impending cell death in that antibiotic concentration and the MIC concentration was adjusted accordingly where appropriate. In the case of bacteria tested for Trimethoprim/Sulfamethoxazole (TMP/SXT), thresholds were generated based on fold inhibition (assay signal in the well containing bacteria but no antibiotic divided by the well containing both antibiotic and bacteria).

Figure 34:
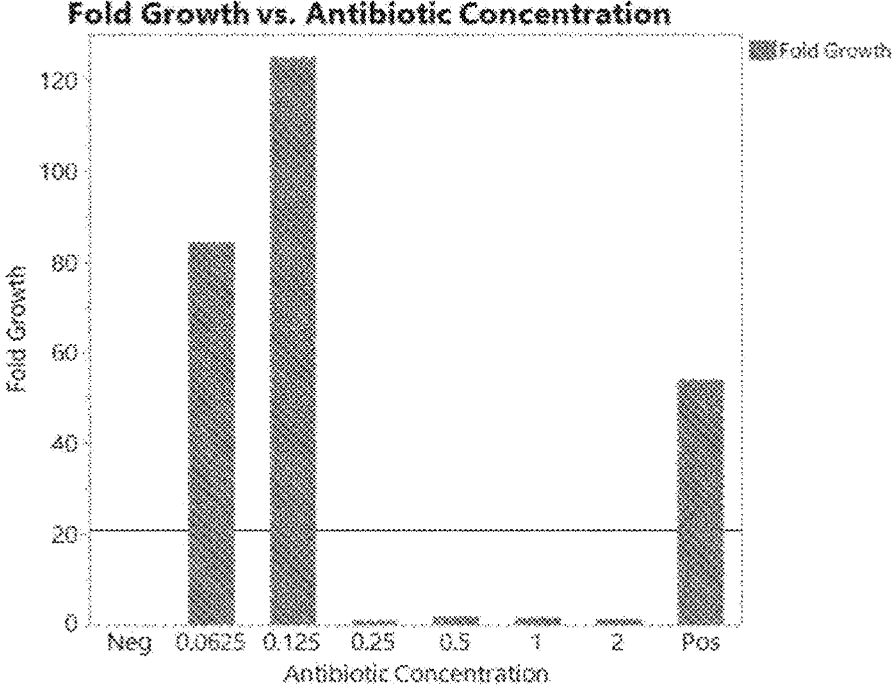
FIG. 34 shows MIC generated by novel rapid AST method described in this invention is called at 0.25 μg/mL

Results. FIG. 34 shows how this method can be used to generate MICs on individual bacteria in the presence of urine matrix that match the CDC or CLSI-published MIC. The example shows the fold growth numbers at different antibiotic concentrations for a single bacterium, (*K. pneumoniae* CDC0126) against a single drug (Ciprofloxacin). The published MIC (≥0.25 μg/mL) matches exactly with the MIC determined by the novel rapid AST method described in this invention. The threshold for fold-growth (20 in this example) is shown by the horizontal grey line.

The table in FIG. 35 shows the overall performance across all strains tested. A tested MIC is within essential agreement if the MIC determined by the novel AST method matches exactly or is within one 2-fold dilution of the published value. Except for two cases, all bacteria/antibiotic combinations had 100% essential agreement.

Conclusions. This novel method shows that MIC determinations that match the published values for highly characterized strains of bacteria with multiple drug resistance mechanism may be made with only 4 hours of growth in the context of sample matrix.

Variations. This example is illustrative of the performance of this novel AST method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations, etc.), concentration of urine and urine processing procedures. This methodology can also clearly be extended to other antibiotics, biological specimens and to other bacteria for which specific probes can be designed.

TABLE A

Bacteria used in this example and their previously determined antibiotic resistance (shown with "X")

| Organism | Number | Ceftazidime | Ciprofloxacin | Meropenem | Trimethoprim/ Sulfamethoxazole | Nitrofurantoin |
|---|---|---|---|---|---|---|
| *E. coli* | CDC0001 | | | X | | |
| *E. coli* | CDC0006 | | | X | | |
| *K. pneumoniae* | CDC0010 | X | | X | X | |
| *K. pneumoniae* | CDC0016 | X | X | X | X | |
| *E. coli* | CDC0017 | | X | | X | |
| *E. coli* | CDC0019 | | X | | X | |
| *E. coli* | CDC0020 | X | | X | | |
| *K. oxytoca* | CDC0028 | X | X | X | X | |
| *P. mirabilis* | CDC0029 | X | X | X | X | Intrinsically resistant |
| *K. pneumoniae* | CDC0034 | | X | X | | |
| *K. pneumoniae* | CDC0041 | X | | | | |
| *K. pneumoniae* | CDC0043 | | | X | | |
| *P. mirabilis* | CDC0059 | X | X | X | X | Intrinsically resistant |
| *E. coli* | CDC0067 | X | | | | |
| *K. oxytoca* | CDC0071 | X | X | X | X | |
| *K. pneumoniae* | CDC0076 | | X | X | | |
| *K. pneumoniae* | CDC0080 | | | X | | |
| *E. coli* | CDC0084 | X | | | X | |
| *E. coli* | CDC0085 | | | X | | |
| *E. coli* | CDC0086 | X | | | | |
| *P. aeruginosa* | CDC0105 | X | | X | Intrinsically resistant | Intrinsically resistant |
| *K. pneumoniae* | CDC0107 | X | | | X | |
| *P. aeruginosa* | CDC0111 | X | | X | Intrinsically resistant | Intrinsically resistant |
| *E. coli* | CDC0114 | | | X | | |
| *K. pneumoniae* | CDC0117 | | X | | X | |
| *K. pneumoniae* | CDC0126 | X | X | | X | |
| *K. oxytoca* | CDC0147 | X | X | X | X | |
| *P. mirabilis* | CDC0155 | X | X | X | X | Intrinsically resistant |
| *P. mirabilis* | CDC0156 | X | X | X | X | Intrinsically resistant |

TABLE A-continued

Bacteria used in this example and their previously determined antibiotic resistance (shown with "X")

| Organism | Number | Ceftazidime | Ciprofloxacin | Meropenem | Trimethoprim/ Sulfamethoxazole | Nitrofurantoin |
|---|---|---|---|---|---|---|
| *P. mirabilis* | CDC0159 | X | X | X | X | Intrinsically resistant |
| *K. pneumoniae* | CDC0160 | X | | | | |
| *P. aeruginosa* | CDC0232 | | | X | Intrinsically resistant | Intrinsically resistant |
| *P. aeruginosa* | CDC0242 | X | | X | Intrinsically resistant | Intrinsically resistant |
| *P. aeruginosa* | CDC0247 | | | X | Intrinsically resistant | Intrinsically resistant |
| *P. aeruginosa* | CDC0251 | X | X | | Intrinsically resistant | Intrinsically resistant |
| *P. aeruginosa* | CDC0253 | X | X | | Intrinsically resistant | Intrinsically resistant |
| *P. aeruginosa* | CDC0259 | | X | | Intrinsically resistant | Intrinsically resistant |
| *P. aeruginosa* | CDC0261 | | X | | Intrinsically resistant | Intrinsically resistant |
| *P. aeruginosa* | CDC0262 | | X | | Intrinsically resistant | Intrinsically resistant |
| *E. coli* | CDC0350 | X | | | | |
| *P. mirabilis* | ATCC7002 | X | X | X | X | Intrinsically resistant |
| *K. pneumoniae* | ATCC13883 | X | X | X | X | |
| *E. coli* | ATCC25922 | X | X | X | X | X |
| *P. aeruginosa* | ATCC27853 | X | X | | Intrinsically resistant | X |
| *K. pneumoniae* | BAA-1904 | | | | | X |
| *E. coli* | BAA-2340 | | | | | X |
| *E. coli* | BAA-2452 | | X | | | X |
| *E. coli* | BAA-2469 | | X | | X | X |
| *E. coli* | BAA-2471 | | X | | X | X |
| *K. pneumoniae* | BAA-2472 | | | | | X |

Example 8. Rapid and Accurate Automatic AST Results for Clinical Urine Specimens without Using Cell Purification Overview. This example demonstrates the use of the systems and methods of the invention to automatically determine AST results for a pathogen in a clinical urine sample in 4 hours without requiring lengthy cell purification steps. The automated instrument performs the steps required in the reagent-containing cartridge to determine antimicrobial susceptibility at a constant physiological temperature. The temperature is compatible with both microbial growth and the inventive method for detecting and quantifying target cells. The latter method is performed on the inventive system using FISH-based labeling, magnetic selection, and non-magnified digital imaging.

The instrument's pneumatics subsystem is used to automatically distribute the specimen in the cartridge into portions or aliquots containing various antimicrobial agents in various concentrations plus microbiological medium. One of the portions is used to quantify the pathogen cells before growth incubation. The system incubates the cartridge for 4 hours and then quantifies the number of target cells in the wells containing antimicrobial agents. Comparison of the number of cells in the incubated portions containing antimicrobial agents to the number of cells measured before incubation is used to determine the antimicrobial susceptibility of the pathogen in the various antibiotics.

The example shows the results using the inventive automated systems, devices, and methods for rapid and automated antimicrobial susceptibility testing directly in clinical specimens from hospital patients that had *E. coli* in their urine. The invention delivered in just 4 hours accurate performance compared to the gold standard CLSI broth microdilution (BMD) method.

Experimental Methods

Urine Specimens: Remnant de-identified urine specimens collected from patients with a urinary tract infection (UTI) and known to contain *E. coli* were received from Dr. Kirby's lab at Beth Israel Hospital (Boston, MA). Samples were received 1-5 days post collection and contained a urine preservative to limit loss of cell viability. For each sample, color of urine, pH, and presence of particulates were noted. Upon receipt, conventional urine culture was performed to determine the approximate CFU/mL of bacteria present, and to confirm single or mixed bacterial morphology as reported by Dr. Kirby's lab. Briefly, a calibrated 1 μL loop was placed into a well-mixed urine sample and the 1 μL was evenly spread over a Tryptic soy agar (TSA) plate and incubated in a 35° C. incubator for 18-24 hours. The remainder of the urine samples were processed and assayed as described below.

Preparation of the AST Cartridge—Media and Antimicrobials

Figures 37, 38:
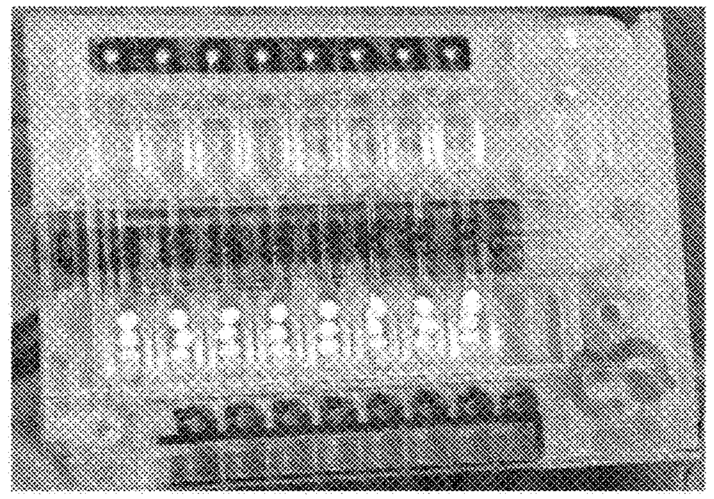
FIG. 37 shows the Multipath™ UTI-AST cartridge
FIG. 38 is a table showing Antibiotic concentrations tested.

Days prior the cartridge was prepared by distributing 25 uL of 4×MHB II (Teknova, Cat. #101320-356) into each of the 8 individual growth wells (see FIG. 37 for a diagram of the cartridge) Growth wells 1 and 2 are for the time zero measurement (see description below), so only growth media is contained in the growth wells. Growth wells 3 and 4 also only contained media. These wells serve as a positive control to make sure growth is observed over four hours. Into growth wells 5 and 6, and 7 and 8, 2 concentrations antibiotic was added. To do this 4.54, of a 22.2-fold more concentrated antibiotic than the target concentration in micrograms per mL was deposited into appropriate growth wells. Cartridges either contained 2 concentrations of both Ciprofloxacin (CIP) and Nitrofurantoin (NIT) or Cefazolin (CFZ) and Trimethoprim/Sulfamethoxazole (TMP/SXT). For final concentrations of each antibiotic in the cartridge, see FIG. 38. The media and antibiotics were then dried for 16-20 hours in a 40° C. convection oven.

Preparation of the AST Cartridge—Hybridization Reagents.

Hybridization buffer containing 3×SSC (0.45 M NaCl, 0.045 M sodium citrate, pH 7.5) (Sigma, cat. #S6639), 0.18% w/v cetrimide, 0.77% CHAPSO (Sigma cat. #C3649), 0.72% SB3-12 (Sigma cat. #D0431), and 0.13M guanidine thiocyanate (Sigma, cat. #G9277) was prepared. Trehalose (Sigma, cat. #T9449) was dissolved in this mixture to a final concentration of 10% w/v. This hybridization buffer-trehalose mixture was lyophilized in 8.3 μL volume beads. Two 8.3 uL beads were placed into each of 8 reagent wells (see FIG. 37, for location on cartridges)

Preparation of the AST Cartridge—Magnetic Particles

Poly-aspartic acid-conjugated magnetic particles (Fluidmag-PAA, Chemicell, cat. 4108) were diluted 1:20 into 50 mM Epps buffer, pH 8.2 to a concentration of $2.75\times10^{14}$ particles/mL with a final concentration of 10% w/v Trehalose (Sigma, cat. #T9449). To this dilution, fluorescent magnetic microspheres containing a green dye (Dragon Green Fluorescent Microspheres, BANGS Laboratories, cat. MEDG001) were added were added to the suspension at a final concentration of $3\times10^{6}$ particles/mL. The magnetic particle mixture was sonicated for 1 minute prior to immediately use to minimize aggregation. The mixture was then lyophilized in 10 μL volume beads ($2.64\times10^{12}$ particles per reaction). One magnetic particle lyophilized bead was placed in each of the 8 reagent wells along with the 2 hybridization mix beads.

Procedure for Placing Samples into the Cartridge—Urine Processing

Prior to testing, urine preservative and other potentially interfering compounds were removed using size exclusion chromatography. 2.5 mL of each clinically positive urine sample was applied to a pre-washed Zeba™ 7K MWCO spin column (ThermoFisher, cat. #89893) and centrifuged according to the manufacturer's instructions. Urine culture was repeated on this processed sample as described above, to examine bacterial loss following processing.

Procedure for Placing Samples into the Cartridge—Putting Samples on Cartridges

750 μL of each processed urine sample was combine with 1705 μL of water and 45 μL of species-specific DNA oligonucleotide fluorescence in situ hybridization (FISH) probes and unlabeled DNA helper probes to make solution containing 30% urine v/v final concentration. Oligonucleotides used for each bacterium, their concentrations and dye labels can be found in FIG. 39. 1 mL of the mixture was added to the sample pot of the cartridge and the cartridge placed onto the analyzer.

Running the AST Cartridges on an Automated Analyzer

After the cartridge was then placed on the instrument, all subsequent actions other than data analysis were automatically performed. The Urine/water/FISH probe mixture (sample) was first directed under vacuum into the 8 growth wells at the top of the cartridge. Sample in the first two growth wells was then immediately relocated to reaction wells, rehydrating the hybridization buffer/FISH probe mix and lyophilized magnetic particles. Sample then continued to the imaging windows containing 46 μL of dehydrated "dye-cushion" (50 mM TRIS pH 7.5 (Teknova, cat. T5075), 7.5% v/v Optiprep (Sigma, cat. D1556), 5 mg/mL Direct Black-19 (Orient, cat. #3222), dried for 60° C. for 3 hours in a convection oven) and incubated at 35° C. for 30 minutes on the analyzer. After this incubation, the cartridges were then relocated to the magnet station, and placed atop a strong permanent magnet (Dexter magnetic technologies, cat. 54170260) for 4 minutes to bring the labeled and magnetic-particle-interacting bacterial cells into close proximity to the imaging surface. Finally, the cartridge was moved to the imaging station and imaging taken using non-magnified CCD imager described below.

Sample in the remaining six growth wells were held in that location, and the bacteria allowed to grow for 4 hours at 35° C. in the rehydrated media, either in the presence or absence of antibiotics. Following growth, the cell suspensions were relocated to the reagent wells as was done for the time zero assay, and the exact same hybridization reaction, magnetic pull-down, and imaging was performed as described above.

The Analyzer Imaging System and Imaging Process

The MultiPath Analyzer imaging system is a custom-built instrument and software that is capable of automatically capturing image data from selected wells of a MultiPath Cartridge as part of a fully automated test. It uses a custom designed precision 3 axis positioning system to locate each well over a fluorescence-based image acquisition subsystem. The Analyzer can image in 4 separate color channels and uses an objective lens, illumination LEDs, fluorescent filter sets, and camera. The objective lens has a field of view designed to capture the image of an entire Cartridge Imaging Well. The illumination module light source consists of 2 high power LEDs per color channel. A series of fluorescent image frames are captured with a camera using a 3.1 MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Data analysis: Using the image captured by the CCD camera, detected cells were estimated by an algorithm that looked at both number of objects in the field of view and the intensity of the objects. Number of cells based on this detection algorithm were generated at time zero, and at time four hours without antibiotic and with both concentrations of each antibiotic. For each urine sample/drug concentration, fold growth was calculated as the signal in the well containing antibiotic after growth (time four) to the signal in the urine sample prior to growth (time zero). Comparison of fold growth and the observation of growth in the corresponding well in the CLSI-compliant broth microdilution, thresholds were selected for the fold growth cutoff to maximize agreement with the broth microdilution results. In conditions where cells are growing in the presence of the antibiotic (and thus, resistant at that concentration), the fold growth will be high and in conditions where cells are in the process of dying (and thus, sensitive at that concentration), the fold growth number will be low. In these cartridges, if both concentrations of antibiotic show no growth based on their fold growth numbers, the bacteria in that urine sample is called sensitive. If there is growth in the lower concentration but not the higher concentration, the bacteria in the urine sample is intermediate in the case of Ciprofloxacin, Nitrofurantoin and Trimethoprim/Sulfamethoxazole and resistant in the case of Cefazolin. If both concentrations of antibiotic show growth based on their fold growth thresholds, the bacteria in that urine sample is called resistant. All sensitive/resistant calls data compared to the sensitive/resistance call made by the MIC determination in a CLSI-compliant standard BMD. Four-hour growth in the absence of antibiotic is a control condition to ensure viable bacterial are present in the processed urine sample.

Figure 40:
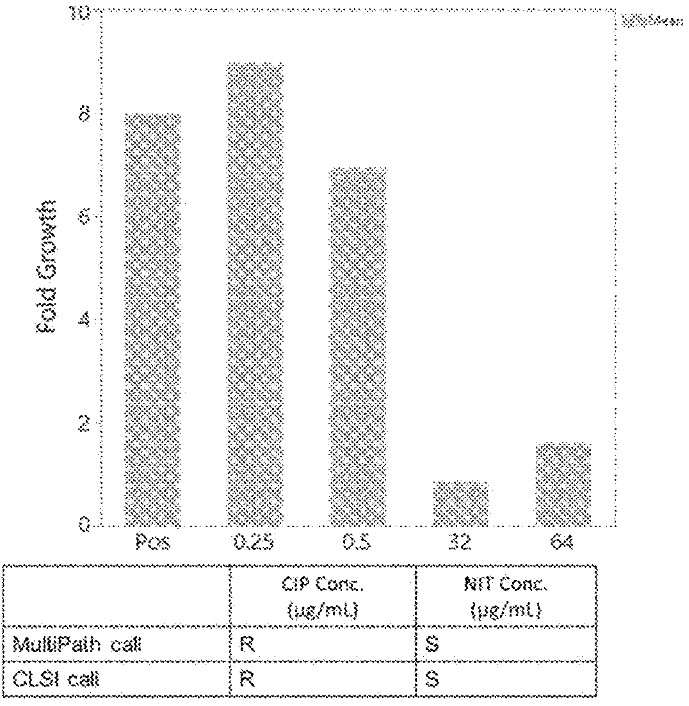
FIG. 40 shows BIUR0067 Results.

Results. FIG. 40 shows the average fold growth of four replicates in two cartridges containing clinical urine sample BIUR0067, which contained an *E. coli* strain. The graph shows the mean fold growth in each of the 2 concentrations each of Ciprofloxacin and Nitrofurantoin across 4 replicates in 2 different cartridges. Using a fold-growth value of 2 for both antibiotics, the MulitPath assay calls both Ciprofloxacin (CIP) concentrations as growth and both the Nitrofurantoin (NIT) concentrations as no growth. Therefore, by MulitPath, BIUR0067 is resistant to ciprofloxacin and sensitive to Nitrofurantoin. The *E. coli* strain isolated from this urine and tested in a CLSI-standard broth microdilution matched these sensitive/resistant calls.

Figure 41:
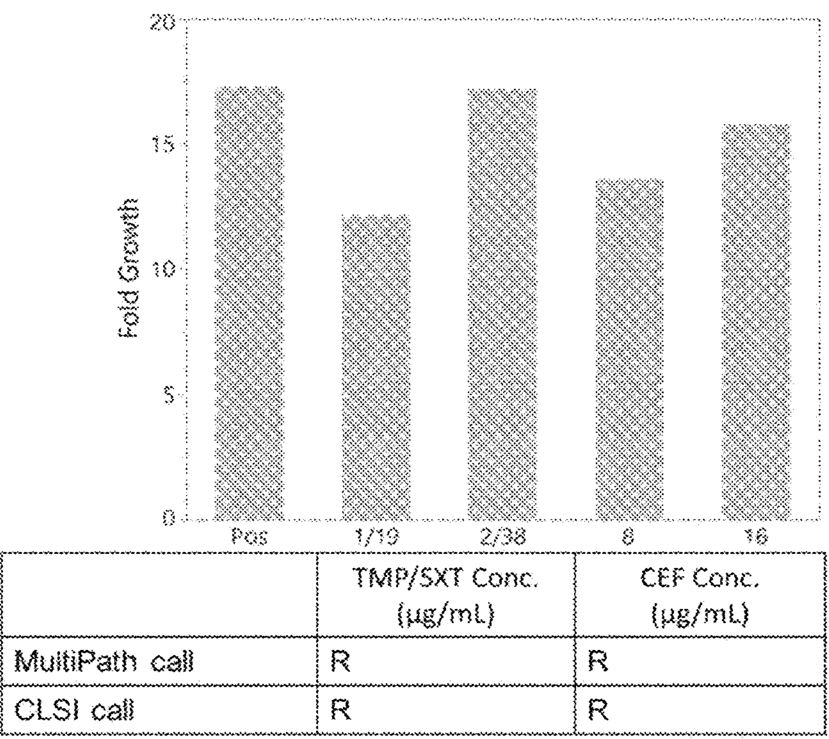
FIG. 41 shows BIUR0084 Results

FIG. 41 shows the average fold growth of four replicates in two cartridges containing clinical urine sample BIUR0084, which contained a *K. pneumonaie* strain. The graph shows the mean fold growth in each of the 2 concentrations each of Cefazolin and Trimethoprim/Sulfamethoxazole across 4 replicates in 2 different cartridges. Using a fold growth value of 2 for both antibiotics, the MulitPath assay calls all the antibiotic concentrations of both Cefazolin and Trimethoprim/Sulfamethoxazole as growth. Therefore, this strain of *K. pneumoniae* is resistant to both antibiotics. This matches both the CLSI-standard broth microdilution done in house.

Conclusions. The example shows the results using the inventive automated systems, devices, and methods for rapid and automated antimicrobial susceptibility testing directly in clinical specimens from hospital patients that had *E. coli* in their urine. The invention delivered in just 4 hours accurate performance compared to the gold standard CLSI broth microdilution (BMD) method.

Variations. This example is illustrative of the performance of this novel AST method on a cartridge and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations), concentration of urine and urine processing procedures and alterations to reactant and antimicrobial stabilization, different bacterial targets, different antimicrobial agents etc. This methodology can also clearly be extended to other biological specimens and to other bacterial and non-bacterial pathogens.

Example 9. Rapid AST Method Directly in Urine Specimens is Robust to Variation Pathogen Concentration Overview. Robustness to variable inoculum concentrations is important for the rapid AST method because when testing specimens directly from specimens the target cell concentration is unknown. This example demonstrates the use of the invention to provide accurate and consistent results directly from a urine specimen when for contrived specimens covering a wide range of target cell concentrations. This example demonstrates that variable cell inputs of *E. coli* BAA-2469, *P. aeruginosa* ATCC 27853, *K. pneumoniae* ATCC 700603 and *K. pneumoniae* CDC-0043 in the presence of 10% urine deliver accurate AST results compared to the Broth Microdilution (BMD) gold standard for AST.

Experimental Procedure

Preparation of Antibiotic Plates: Antibiotic plates containing either concentrations of three to five antibiotics in a 2-fold serial dilution series were prepared by distributing 10 μL of 10-fold higher concentration than the desired final concentration into the wells of a 96 well plate. The concentrations selected for testing of each antibiotic straddled the CLSI-reported MICs for the bacterial strains tested. Plates were prepared with all or a subset of the following antibiotics: Cefazolin, Ciprofloxacin, Levofloxacin, Nitrofurantoin, and Trimethoprim-Sulfamethoxazole. In addition to the wells containing the antimicrobial dilution series, four wells contained water to allow for positive (bacteria growth in the absence of antibiotic) and negative (no bacterial cells) controls.

Preparation of Cultures: Bacterial cultures for *E. coli* BAA-2469, *P. aeruginosa* ATCC 27853, *K. pneumoniae* ATCC 700603, and *K. pneumoniae* CDC-0043 were obtained by inoculating Trypticase Soy Broth (TSB, Hardy Diagnostics cat. U65) with 3 to 5 colonies from fresh tryptic soy agar plates (TSA, BD cat. 221185) and growing for 1.5 to 3 hours at 35° C. to achieve log-phase growth. The cells were diluted in 1× cation-adjusted Mueller-Hinton broth (MHBII, Teknova cat. M5860) to various inoculum ($2\times10^3$ CFU/mL-$1\times10^7$ CFU/mL). For more accurate cellular concentrations, these estimated bacterial inputs were adjusted using colony counts. Plate counts were determined by diluting the log-phase cultures to about 500 CFU/mL in MHBII, plating 100 μL on TSA plates and counting colonies after growth at 35° C. for 16 to 24 hours. Using the average plate counts, the actual CFU present in each concentration tested was computed.

Preparation of Magnetic Particles: 2 hydroxypropyl trimethylammonium chloride coated silica magnetic particles (SiMag-Q, Chemicell, cat. 1206-5) were diluted 1:20 into 50 mM EPPS buffer, pH 8.2 to $2.75\times10^{12}$ particles/mL. Fluorescent magnetic microspheres containing a green dye (Dragon Green Fluorescent Microspheres, BANGS Laboratories, cat. MEDG001) were added to the suspension at a final concentration of $3\times10^6$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below.

Bacterial Cell Labeling at AST time zero: Assay signal prior to the initiation of bacterial growth in the presence or absence of antibiotics (time zero or T0) was determined for each organism and inoculum. 10 μL of each sample was added to 80 μL of hybridization buffer to final concentrations of 3×SSC (0.45 M NaCl, 0.045 M Na citrate, Sigma, cat. #S6639), 1% CHAPS (Sigma, cat. #C3023), 1% NOG (Sigma cat. #08001), 1× cation-adjusted Mueller-Hinton Broth (MHBII), species-specific DNA oligonucleotide FISH probes and unlabeled DNA helper probe. The oligonucleotide probes used are shown in Table B. A final concentration of 10% urine was obtained by adding 10 μL of pooled urine (in-house collected and filtered) directly to the mixture. 10 μL of the magnetic particle mixture prepared as described above was then added. 100 μL of this reaction mixture was transferred to a microtiter plate containing 50 μL per well (previously dried) of "dye cushion" (50 mM TRIS pH 7.5 (Teknova, cat. T5075), 7.5% v/v Optiprep (Sigma, cat. D1556), 5 mg/mL Direct Black-19 (Orient, cat. #3222) (dry-cushion plate) and incubated at 35° C. for 30 minutes. After incubation, microtiter plates were placed onto a magnetic field (Dexter magnetic technologies, cat. 54170260) for 4 minutes to bring magnetic particles, a fraction containing labeled cells, through the "dye cushion" and into proximity to the imaging surface at the bottom of the wells.

Imaging of labeled cells: The MultiPath™ laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1 MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Four-Hour Growth: While the time zero cell quantification was occurring, 10 μL of each organism inoculum, 10 μL of pooled urine, and 70 μL of 1×MHBII was added to the appropriate wells of the antibiotic plate (already containing 10 μL of antibiotic). The samples were allowed to grow in a standard air incubator at 35° C. for 4 hours.

Bacterial Cell Labeling at AST time four-hour growth: After samples had incubated in the presence and absence of antibiotics for four hours (T4), cells were labeled and quantified to determine how much growth, if any, occurred. 10 μL of the incubated sample-antibiotic plate (10%) was transferred to a microtiter plate and combine with 100 μL hybridization buffer, FISH probes, helper probes, magnetic particles, and focus particles in the same manner as described above for assay time zero.

Comparison Method: Results using the novel AST method described here were compared to broth microdilutions (BMD) performed according to CLSI M07-Ed13E 2018.

Data Analysis and Threshold Generation: Using the image captured by the CCD camera, detected cells were estimated by an algorithm that looked at both number of objects in the field of view and the intensity of the objects. The number of cells based on this detection algorithm were generated at time zero, and at time four hours without antibiotic and with all concentrations of each antibiotic. For each sample inoculum/drug concentration, fold growth was calculated as the signal in the well containing antibiotic after growth (time four) to the signal in the urine sample prior to growth (time zero). Using fold growth and the observation of growth in the corresponding well in the CLSI-compliant broth microdilution, a logistic regression model was used to generate thresholds for determining the fold growth cutoff above which cells are growing in the presence of the antibiotic (and thus, resistant at that concentration) and below which, cells are in the process of dying (and thus, sensitive at that concentration). The point where the fold growth number falls below the determined threshold is the MIC value generated by the assay. Results were correspondingly assigned to categories of susceptible, intermediate, or resistant to each antibiotic. All data was then compared to CLSI standard BMD. Four-hour growth in the absence of antibiotic is a control condition to ensure viable bacterial are present in the processed urine sample.

Results

Figures 43, 44:
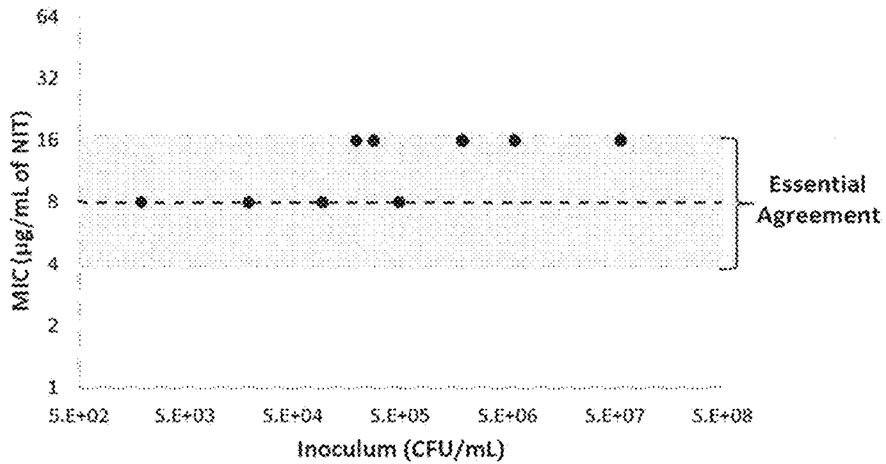
FIG. 43 shows MIC results for various inoculum levels generated using the new methods described here compared to the conventional BMD method.
FIG. 44 is a Summary of MIC results for the various inoculum levels generated.

FIG. 42 through FIG. 45 show how this method is robust to varying inoculum levels while matching the gold-standard broth microdilution method. FIG. 42 compares the results obtained with the novel AST method to results of a standard BMD performed at a single concentration for all drugs tested. Column 3 compared the MICs obtained via the novel AST method and the gold-standard BMD. All MIC calls were within one 2-fold dilution (Essential Agreement) of the CLSI-compliant BMD. Column 4 compared categorical antibiotic susceptibility results (S=susceptible, I=intermediate, R=resistant) based on the MIC (Categorical agreement). Although a subset of *Klebsiella* concentrations gave different categorical calls from the MIC in broth microdilution, all of these were only classified as minor errors by standard AST methodology. FIG. 44 shows MICs generated with the novel 4-hour method described above for all inoculum levels for *E. coli* BAA-2469 (solid circles) compared to the standard broth microdilution method (24 hr BMD, dashed line). All MICs determined with this novel method are within essential agreement (shaded area). FIG. 45 shows the raw data for FIG. 43.

Conclusion. The rapid 4-hour AST method presented here is robust to initial cell concentration over a wide range of target cell concentrations. Robustness to variable inoculum concentrations is important for the rapid AST method because when testing specimens directly from specimens the target cell concentration is unknown.

Variations. This example is illustrative of the performance of this novel AST method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations), concentration of urine and urine processing procedures. This methodology can also clearly be extended to other biological specimens and to other bacterial and non-bacterial pathogens for which specific probes can be designed, and for other antimicrobial or chemical agents.

Example 10. Rapid Antimicrobial Susceptibility Testing for Target Pathogens in Urine Clinical Specimen Containing Multiple Bacterial Species without Cell Purification Overview. Current methods for antimicrobial susceptibility testing require lengthy culture-based colony purification to ensure a pure population of the target pathogen cells free of other microbes. The usual method, colony purification requires, 2-5 days to deliver results. In the interim, patients are treated empirically with powerful broad-spectrum antibiotics that may not be optimal for killing the pathogen causing the infection and can even be completely ineffective. Plus, empiric treatment with broad-spectrum antibiotics causes the spread of antibiotic resistance.

Current methods require the lengthy cell purification process because these methods use non-specific detection methods, such as increase in turbidity, to determine which antimicrobial agents inhibit the growth of the target pathogen in microbiological medium. When using non-specific measurement of cellular replication one can only know that the growth seen is due to the target pathogen if the contains only cells of the target pathogen. Cell purification must be undertaken for current antimicrobial susceptibility testing methods because most medical specimens are non-sterile. Specimens generally contain microbes that make up the human microbiome, the benign normal bacterial population that populate our bodies.

In contrast, the inventive method can deliver accurate antimicrobial susceptibility testing results directly from specimens without the colony purification step. The method differs from current methods in that it assesses growth specifically for the target pathogen in microbiological medium containing antimicrobial agents.

This example demonstrates that the rapid antimicrobial susceptibility testing method accurately determines the minimum inhibitory concentration (MIC) for an *E. coli* strain in contrived samples comprising urine matrix (10%) for 15 different culture-negative urine samples. Here we show that using the new method antimicrobial susceptibility testing results are accurate and not significantly impacted by off-target bacteria in urine samples containing high concentrations of other microbial species.

Experimental Procedure

Preparation of Antibiotic Plates: Prior to initiating experimental procedure, a plate containing five concentrations in a 2-fold serial dilution series were prepared by distributing 10 μL of 10-fold higher concentration than the desired concentration. The concentrations selected for testing of each antibiotic straddled the CLSI-reported breakpoints for the antibiotic for *E. coli*. In addition to the wells containing the antimicrobial dilution series, four wells containing water were included in the plates to allow for a positive and negative control.

Preparation of Cultures: Three to five colonies of *E. coli* BAA-2469 as well as eight other off-target species (*S. aureus* ATCC 25923, *C. freundii* ATCC 43864, *A. baumannii* ATCC 19606, *S. epidermidis* ATCC 12228, *M. luteus* (environmental isolate), *C. minutissmum* ATCC 23348-BAA 949, *K. pneumoniae* CDC 0043, and *K. pneumoniae* CDC 0141) were each inoculated separately into 5 mL of Tryptic Soy Broth (TSB, Hardy Diagnostics cat. U65) and incubated while shaking for 1-2 hours at 35° C. The optical density was measured by a spectrophotometer and the organisms were diluted in 1× cation-adjusted Mueller-Hinton Broth (MHBII, Teknova cat. M5860). *E. coli* was diluted to approximately $5\times10^6$ CFU/mL (final assay concentration is $5\times10^5$ CFU/m) while the other off-target species were diluted to various inoculum (ranging from $1\times10^5$ to $5\times10^8$ CFU/mL).

Preparation of Magnetic Particles: 2 hydroxypropyl trimethylammonium chloride-coated silica magnetic particles (SiMag-Q, Chemicell, cat. 1206-5) were diluted 1:20 into 50 mM EPPS buffer, pH 8.2 to $2.75\times10^{12}$ particles/mL. Fluorescent magnetic microspheres containing a green dye (Dragon Green Fluorescent Microspheres, BANGS Laboratories, cat. MEDG001) were added to the suspension at a final concentration of $3\times10^6$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below.

Bacterial Cell Labeling at AST time zero: Assay signal prior to the initiation of bacterial growth in the presence or absence of antibiotics (time zero or T0) was determined for each species of *E. coli.* 10 μL of each sample was added to 80 μL of hybridization buffer (3×SSC (0.45 M NaCl, 0.045 M sodium citrate) (Sigma, cat. #S6639), 1% CHAPS (Sigma, cat. #C3023), 1% SB3-12 (Sigma cat. #08001), 1× Cation-adjusted Mueller-Hinton Broth (MHBII), *E. coli*-specific DNA oligonucleotide FISH probes and unlabeled DNA helper probe)). Probe sequences are shown in Table in FIG. 51. A final concentration of 9.1% urine was obtained by adding 10 μL of pooled urine (in-house collected and filtered) directly to the mixture. 10 μL of the magnetic particle mixture prepared as described above was added directly to this mixture. 100 μL of the sample, now containing the hybridization mixture, urine, and magnetic particles, was transferred to a microtiter plate containing 50 μL per well (previously dried) of "dye cushion" (50 mM TRIS pH 7.5 (Teknova, cat. T5075), 7.5% v/v Optiprep (Sigma, cat. D1556), 5 mg/mL Direct Black-19 (Orient, cat. #3222) and incubated at 35° C. for 30 minutes. After incubation, microtiter plates were placed onto a magnetic field (Dexter magnetic technologies, cat. 54170260) for 4 minutes to bring magnetic particles, a fraction containing labeled cells, through the "dye cushion" and into proximity to the imaging surface at the bottom of the wells.

Imaging of labeled cells: The MultiPath™ laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1 MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Four-Hour Growth: The *E. coli* BAA 2469, in the presence of *Staphylococcus epidermidis, Micrococcus luteus, Corynebacterium minutissimum, Staphylococcus aureus, Acinetobacter baumannii, Citrobacter freundii*) were tested for their susceptibility against 3 antimicrobial agents: Ciprofloxacin (CIP), Levofloxacin (LVX), and Nitrofurantoin (NIT). *E. coli* BAA 2469, in the presence of *Klebsiella pneumoniae* was tested against 5 antimicrobial agents: Cefazolin (CFZ), Ciprofloxacin (CIP), Levofloxacin (LVX), Nitrofurantoin (NIT), and Trimethoprim-Sulfamethoxazole (TMP/SXT). Antibiotic plates containing these antimicrobial agents were prepared according to the method described above. While the time zero cell quantification was occurring, 10 μL of either *E. coli* species ($5\times10^6$ CFU/mL), 10 μL of an off-target species ($1\times10^5$ to $5\times10^8$ CFU/mL), 10 μL of pooled urine, and 60 μL of MHB II (Teknova, cat. #M5860) was added to each well of the antibiotic plate already containing 10 μL of antibiotics. The samples were allowed to grow in a standing air incubator at 35° C. for 4 hours.

Bacterial Cell Labeling at AST time four-hour growth: After samples had incubated in the presence and absence of antibiotics for four hours (T4), cells were labeled and quantified to determine how much growth, if any, occurred. 10 µL of the incubated sample-antibiotic plate (10%) was transferred to a microtiter plate containing dried "dye cushion" and combined with the 100 µL mixture of hybridization buffer, FISH probes, helper probes, magnetic particles, and focus particles as described above for assay time zero.

Comparison Method: Results for the novel assay method described here were compared to broth microdilutions (BMD) performed according the M07-Ed13E 2018.

Data Analysis and Threshold Generation: Using the image captured by the CCD camera, detected cells were estimated by an algorithm that looked at both number of objects in the field of view and the intensity of the objects. Number of cells based on this detection algorithm were generated at time zero, and at time four hours without antibiotic and with all concentrations of each antibiotic. For each bacteria sample/drug concentration, fold growth was calculated as the signal in the well containing antibiotic after growth (time four) to the signal in the urine sample prior to growth (time zero). Using fold growth and the observation of growth in the corresponding well in the CLSI-compliant broth microdilution, a logistic regression model was used to generate thresholds for determining the fold growth cutoff above which cells are growing in the presence of the antibiotic (and thus, resistant at that concentration) and below which, cells are in the process of dying (and thus, sensitive at that concentration). The point where the fold growth number falls below the determined threshold is the MIC value generated by the assay. Results were correspondingly assigned to categories of susceptible, intermediate, or resistant to each antibiotic.

Results

Figures 46, 47:
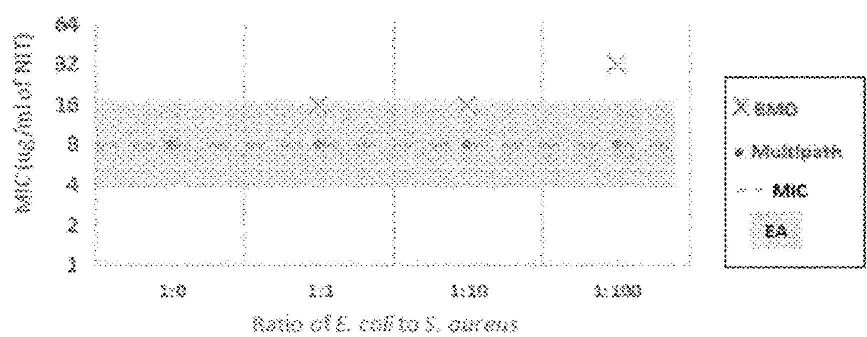
FIG. 46 shows the MIC for *E. coli* stays consistent with the method describe above with varying inoculum of *S. aureus* while the MIC for BMD increases with increasing *S. aureus.*
FIG. 47 shows a summary of agreement for *E. coli* with varying inoculum levels of off-target microbe to standard BMD.

The data shown demonstrate the 4-hour AST method described above is robust to non-sterile samples while a CLSI BMD method where extra bacteria is present is not. FIG. 46 shows the data for *E. coli* BAA-2469 in the presence of Nitrofurantoin and with increasing concentrations of *S. aureus* ATCC 25923 up to an excess of 100-fold. The *E. coli* MIC in the CLSI-like broth microdilution method is affected by the addition of the *S. aureus* strain (marked as X in the figure) where the MIC increases from 8 in the absence of *S. aureus* to 32 with a 100-fold excess of *S. aureus*. In contrast, the novel 4-hour AST assay described in this invention (MultiPath, circles) had the same MIC (8) (dashed line) regardless of the amount of *S. aureus* cells.

FIG. 48 through FIG. 50 show the raw MIC values determined using this novel method (MultiPath) compared to a CLSI broth microdilution where only the *E. coli* BAA-2469 is present. Table in FIG. 47 shows the overall essential agreement of *E. coli* in the presence of increasing off-target bacteria. Only a single condition—1e7 *Citrobacter freundii* with Nitrofurantoin—resulted in a lack of essential agreement but this did not change the categorical sensitive/intermediate/resistant determination which had 100% agreement across all antibiotics and all off-target bacteria.

Conclusions. The example demonstrates that using the invention for antimicrobial susceptibility testing, cell purification is not required for achieving accurate antimicrobial susceptibility testing results for a target pathogen in samples containing even large numbers of other microbes of other species.

Variations: This example is illustrative of the performance of this novel FISH method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations), concentration of urine and urine processing procedures. This methodology can also clearly be extended to other biological specimens and to other bacterial and non-bacterial pathogens.

Example 11. Rapid Antimicrobial Susceptibility Testing is Accurate for Lactam Antibiotics in the Presence of Bacteria Expressing Beta-Lactamase Overview. Current methods for antimicrobial susceptibility testing require lengthy culture-based colony purification to ensure a pure population of the target pathogen cells free of other microbes. The usual method, colony purification requires, 2-5 days to deliver results. In the interim, patients are treated empirically with powerful broad-spectrum antibiotics that may not be optimal for killing the pathogen causing the infection and can even be completely ineffective. Plus, empiric treatment with broad-spectrum antibiotics causes the spread of antibiotic resistance.

One reason that current methods require the lengthy cell purification process because these methods use non-specific detection methods, such as increase in turbidity, to determine which antimicrobial agents inhibit the growth of the target pathogen in microbiological medium. When using non-specific measurement of cellular replication one can only know that the growth seen is due to the target pathogen if the contains only cells of the target pathogen.

In contrast, the inventive method can deliver accurate antimicrobial susceptibility testing results directly from specimens without the colony purification step. The method differs from current methods in that it assesses growth specifically for the target pathogen in microbiological medium containing antimicrobial agents. We demonstrate in another example, that the inventive method is accurate in the presence of large numbers of cells from off-target species.

In this example, we address another challenge that could arise by performing antimicrobial susceptibility testing for a target pathogen in the presence of off-target species. Here we demonstrate that the inventive method delivers accurate antimicrobial susceptibility testing results for a target pathogen in contrived urine specimens containing large numbers of an off-target species that makes an enzyme known to break down the antimicrobial agent being tested. Theoretically this could potentially change the concentration of the antimicrobial agent significantly enough to alter the antimicrobial susceptibility testing result.

In this example, we demonstrate that the rapid antimicrobial susceptibility testing achieves accurate antimicrobial susceptibility testing results for two carbapenem antibiotics (Meropenem and Imipenem) in the presence of large numbers of an off-target pathogen that produces a enzyme that breaks down this type of antimicrobial agent.

Experimental procedure. Preparation of Antibiotic Plates: Antibiotic plates prepared as described in Impact of Non-Sterile Sample on Target MIC example.

Preparation of Cultures: Three to five colonies of *E. coli* ATCC 25922, a strain of bacteria sensitive to most antibiotics and *K. pneumoniae* CDC 0141, a strain that, among many other resistance genes, expresses the beta-lactase OXA-181, were each inoculated separately into 5 mL of Tryptic Soy Broth (TSB, Hardy Diagnostics cat. U65) and incubated while shaking for 1-2 hours at 35° C. The Optical Density was measured by a spectrometer and the organisms were diluted in 1× cation-adjusted Mueller-Hinton Broth (MHBII, Teknova cat. M5860). *E. coli* was diluted to $5\times10^5$ CFU/mL (CLSI standard concentration) while *K. pneumoniae* was diluted to various inoculum (ranging from $1\times10^6$ and $5\times10^8$ CFU/mL).

Preparation of Magnetic Particles: 2 hydroxypropyl trimethylammonium chloride-coated silica magnetic particles (SiMag-Q, Chemicell, cat. 1206-5) were diluted 1:20 into 50 mM EPPS buffer, pH 8.2 to $3.75\times10^6$ particles/mL. Fluorescent magnetic microspheres containing a green dye (Dragon Green Fluorescent Microspheres, BANGS Laboratories, cat. MEDG001) were added to the suspension at a final concentration of $3\times10^6$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below.

Bacterial Cell Labeling at AST time zero: Assay signal at time zero (T0) prior to the initiation of bacterial growth in the presence or absence of antibiotics was determined for each clinical urine specimen. 30 μL of each processed urine was added to 70 μL of 1× cation-adjusted Mueller-Hinton Broth (MHBII) containing species-specific Alexa647N-labeled DNA oligonucleotide FISH probes and unlabeled DNA helper probes. Probe sequences used are shown in FIG. 54. The 100 μL mixture was then added to a well of a microtiter plate containing dehydrated hybridization buffer (3×SSC (0.45 M NaCl, 0.045 M Na citrate) buffer (Sigma, cat. #S6639), 0.18% cetrimide (Sigma, cat. #H9151), 0.77% CHAPSO (Sigma cat. #C3649), 0.72% SB3-12 (Sigma cat. #D0431) 0.13M guanidine thiocyanate (Sigma, cat. #G9277)). 104, of the prepared magnetic particle mixture was then added to the well. 100 μL of this reaction mixture was transferred to a microtiter plate containing 50 μL per well (previously dried) of "dye-cushion" (50 mM TRIS pH 7.5 (Sigma cat. T1075), 7.5% v/v Optiprep (Sigma cat. D1556), 50 mg/mL Direct Black 19 (Orient cat. 191L) and incubated at 35° C. for 30 minutes. After incubation, microtiter plates were placed onto a magnetic field (Dexter magnetic technologies, cat. 54170260) for 4 minutes to bring magnetic particles, a fraction containing labeled cells, through the "dye-cushion" and into proximity to the imaging surface at the bottom of the wells.

Imaging of labeled cells: The MultiPath' laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1 MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Four-Hour Growth: The *E. coli* was tested in the presence of varying inoculum of *K. pneumoniae*-OXA for susceptibility against 2 antimicrobial agents: Imipenem and Meropenem. While the time zero cell quantification was occurring, 10 μL of the *E. coli* species ($5\times10^6$ CFU/mL), 10 μL of the *K. pneumoniae* ($1\times10^6$ to $1\times10^8$ CFU/mL) or 10 uL media (control), 10 μL of pooled urine, and 60 μL of MHB II (Teknova, cat. #M5860) was added to each well of the antibiotic plate already containing 10 μL of antibiotics. The samples were allowed to grow in a standing air incubator at 35° C. for 4 hours.

Bacterial Cell Labeling at AST time four-hour growth: After samples had incubated in the presence and absence of antibiotics for four hours (T4), cells were labeled and quantified to determine how much growth, if any, occurred. 100 μL of each well of the incubated sample-antibiotic plate was transferred to a corresponding well of a dehydrated buffer plate and combined with FISH probes, helper probes, magnetic particles, and focus particles in the same manner as described above for assay time zero.

Comparison Method: Results for the MulitPath™ Assay were compared to broth microdilutions (BMD) performed according to the CLSI method M07-Ed13E 2018.

Data Analysis and Threshold Generation: Using the image captured by the CCD camera, detected cells were estimated by an algorithm that looked at both number of objects in the field of view and the intensity of the objects. Number of cells based on this detection algorithm were generated at time zero, and at time four hours without antibiotic and with all 6 concentrations of each antibiotic. For each urine sample/drug concentration, fold growth was calculated as the signal in the well containing antibiotic after growth (time four) to the signal in the urine sample prior to growth (time zero). Using fold growth and the observation of growth in the corresponding well in the CLSI-compliant broth microdilution, a logistic regression model was used to generate thresholds for determining the fold growth cutoff above which cells are growing in the presence of the antibiotic (and thus, resistant at that concentration) and below which, cells are in the process of dying (and thus, sensitive at that concentration). The point where the fold growth number falls below the determined threshold is the MIC value generated by the assay. Results were correspondingly assigned to categories of susceptible, intermediate, or resistant to each antibiotic. All data was then compared to CLSI standard BMD. Four-hour growth in the absence of antibiotic is a control condition to ensure viable bacterial are present in the processed urine sample.

Figure 52:
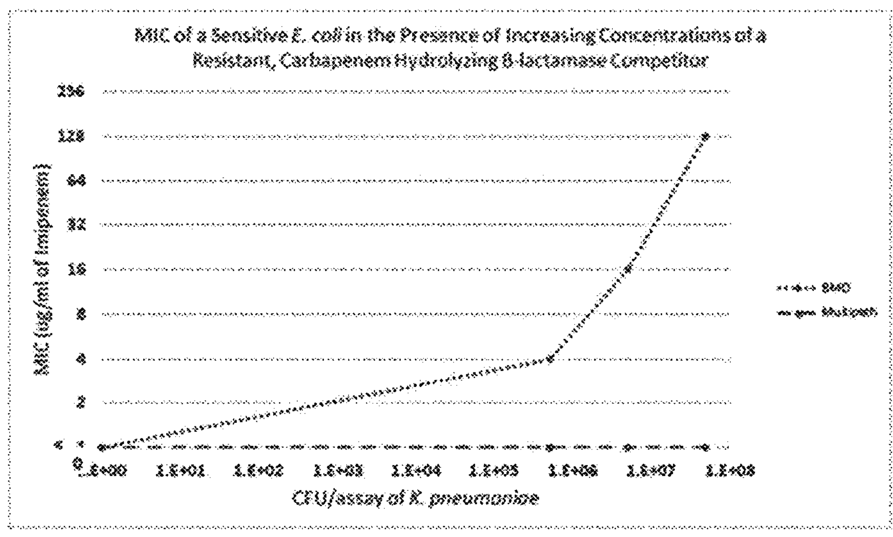
FIG. 52 is a comparison of the novel rapid AST and BMD methods for determining Imipenem MIC for *E. coli* in the presence of a resistant carbapenem hydrolyzing B-lactamase strain of *K. pneumonaie.*
Figure 53:
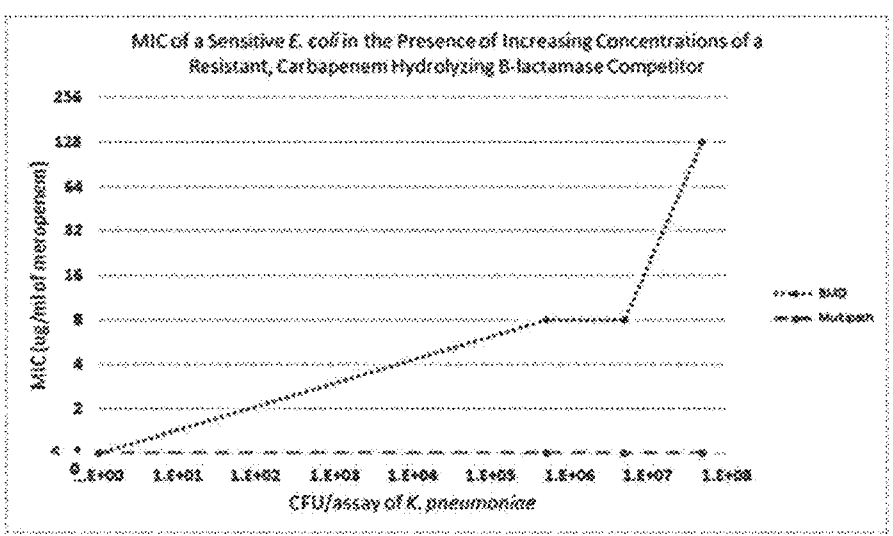
FIG. 53 shows the MIC for *E. coli* stays consistent with the method describe above with varying inoculum of a resistant carbapenem hydrolyzing B-lactamase strain of *K. pneumonaie* while standard BMD does now.

Results. FIG. 52 shows the MIC of a sensitive *E. coli* strain to Imipenem in the presence of increasing amounts of a *K. pneumonaie* strain that is resistant to the Imipenem antibiotic by producing a beta-lactamase that degrades it. The novel rapid AST method of this invention is compared to the BMD method. The novel 4.5-hour AST method is unaffected by the presence of even high concentrations of the beta-lactamase producing *K. pneumonaie* with MICs consistently less than 1 μg/mL Imipenem. In contrast, the BMD method after 16-24 hours of growth shows increasing MIC for the sensitive *E. coli* strain with increasing levels of *K. pneumonaie*, which would be falsely determined to be resistant to this antibiotic. FIG. 53 shows similar results for the lactam antibiotic Meropenem.

Conclusions. The novel 4.5-hour AST method of this invention shows accurate MIC determination of bacteria sensitive to carbapenem antimicrobial agents even in the presence of high concentrations of a resistant bacteria expressing a carbapemase enzyme which degrades the antibiotic.

Variations. This example is illustrative of the performance of this novel AST method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations, etc.), concentration of urine and urine processing procedures. This methodology can also be extended to additional pairings of lactam sensitive and beta-lactamase expressing bacteria.

Example 12. Accurate Rapid Antimicrobial Susceptibility Testing of Bacteria in Urine without Culture-Based Cell Purification Overview: Current methods for antimicrobial susceptibility testing require lengthy culture-based colony purification to ensure a pure population of just pathogen cells free of the specimen itself. Consequently, antimicrobial susceptibility testing results that indicate which antibiotics are optimal for killing the pathogen causing the infection are not available for 2-5 days. In the interim, patients are treated empirically with powerful broad-spectrum antibiotics that may not be optimal for killing the pathogen causing the infection and can even be completely ineffective. Plus, empiric treatment with broad-spectrum antibiotics causes the spread of antibiotic resistance.

In contrast, the inventive method can deliver accurate antimicrobial susceptibility testing results directly from specimens without the lengthy colony purification step. Here we show that the new antimicrobial susceptibility testing results are not significantly impacted when bacteria in urine samples are tested without colony purification. This example demonstrates that the rapid antimicrobial susceptibility testing method accurately determines the minimum inhibitory concentration (MIC) for an *E. coli* strain in contrived samples comprising urine matrix (10%) for 15 different culture-negative urine samples.

Experimental procedure. Urine specimens: Fifteen culture negative clinical urine samples (remnants) were purchased from Discovery Life Sciences. Samples were received >7 days post collection and stored at −80° C. until use. For each sample, color of urine, pH, and presence of particulates were noted. Upon receipt, conventional urine culture was performed on the urines to determine samples were culture negative. Briefly, a calibrated 1 uL loop was placed into a well-mixed urine sample and evenly spread over a Tryptic soy agar (TSA) plate and incubated in a 35° C. air incubator for 18-24 hours. The remainder of the urine samples were assayed as described below.

Preparation of Antibiotic Plates: Microtiter plates containing six concentrations of each antibiotic in a 2-fold serial dilution series were prepared, starting at a 10-fold higher concentration than the expected minimum inhibitory concentration (MIC). Antibiotics used were Cefazolin, Ciprofloxacin, Nitrofurantoin, and Trimethoprim-Sulfamethoxazole. Antibiotic dilutions were verified to be within the appropriate tolerance by confirming that the MIC for at least two CLSI QC strains fell within the QC range reported in CLSI document M100Ed29E-2019. The concentrations selected for testing of each antibiotic straddled the CLSI-reported breakpoints for the antibiotic for *E. coli*. In addition to the wells containing the antimicrobial dilution series, eight wells containing water or diluent were included in the plates to allow for a no antibiotic positive and negative growth control.

Preparation of Cultures: A log culture for *E. coli* (BAA-2469) was grown using three to five colonies inoculated into 5 mL of Tryptic Soy Broth (TSB, Hardy Diagnostics cat. U65) and incubated while shaking for 1-2 hours at 35° C. The Optical Density was measured by a spectrophotometer and the organisms were diluted to $5\times10^6$ CFU/mL (for a final concentration of $5\times10^5$ CFU/mL in each 100 μL reaction) in 1× Cation-adjusted Mueller-Hinton Broth (MHBII, Teknova cat. M5860).

Preparation of Magnetic Particles: 2 hydroxypropyl trimethylammonium chloride-coated silica magnetic particles (SiMag-Q, Chemicell, cat. 1206-5) were diluted 1:20 into 50 mM EPPS buffer, pH 8.2 to $2.75\times10^{12}$ particles/mL. Fluorescent magnetic microspheres containing a green dye (Dragon Green Fluorescent Microspheres, BANGS Laboratories, cat. MEDG001) were added to the suspension at a final concentration of $3\times10^6$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below.

Bacterial Cell Labeling at AST time zero: Assay signal prior to the initiation of bacterial growth in the presence or absence of antibiotics (time zero or T0) was determined for each urine sample. 10 μL of diluted *E. coli* was added to 70 μL of hybridization buffer: final concentration: 3×SSC (0.45 M NaCl, 0.045 M Na citrate) buffer (Sigma, cat. #S6639), 1% CHAPS (Sigma, cat. #C3023), 1% NOG (Sigma cat. #08001), 1× Cation-adjusted Mueller-Hinton Broth (MHBII) (from a 2× stock) (Teknova, cat. M5866), and non-specific DNA oligonucleotide FISH probes and unlabeled DNA helper probe (see FIG. 58 for probe labels, sequences, and concentrations). A final concentration of 10% urine was obtained by adding 10 μL of each individual urine directly to the mixture. 10 μL of the magnetic particle mixture prepared as described above was added directly to this mixture. 100 μL of the sample, now containing the hybridization mixture, urine, and magnetic particles, was transferred to a microtiter plate containing 50 μL per well (previously dried) of "dye cushion" (50 mM TRIS pH 7.5 (Teknova, cat. T5075), 7.5% v/v Optiprep (Sigma, cat. D1556), 5 mg/mL Direct Black-19 (Orient, cat. #3222), dried at 60° C. in a convection oven for 3 hours) and incubated at 35° C. for 30 minutes. After incubation, microtiter plates were placed onto a magnetic field (Dexter magnetic technologies, cat. 54170260) for 4 minutes to bring magnetic particles, a fraction containing labeled cells, through the "dye cushion" and into proximity to the imaging surface at the bottom of the wells.

Imaging of labeled cells: The MultiPath™ laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1 MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Four-Hour Growth: Spiked culture negative clinical UTI urine samples were tested for their susceptibility against 5 antimicrobial agents: Cefazolin, Ciprofloxacin, Levofloxacin, Nitrofurantoin, and Trimethoprim-Sulfamethoxazole. Antibiotic plates containing these antimicrobial agents were prepared according to the method described above. At the same time as the time zero cell quantification was occurring, 10 μL of *E. coli,* 10 μL of urine, and 70 μL of 1×MHB II (Teknova, cat. M5860) were added to each well of the antibiotic plate. The samples were allowed to grow in a standing air incubator at 35° C. for 4 hours.

Bacterial Cell Labeling at AST time four-hour growth: After samples had incubated in the presence and absence of antibiotics for four hours (T4), cells were labeled and quantified to determine how much growth, if any, occurred. 100 μL of each well of the incubated sample-antibiotic plate was transferred to a corresponding well of a dehydrated buffer plate and combined with FISH probes, helper probes, magnetic particles, and focus particles in the same manner as described above for assay time zero.

Comparison Method: Results for the MulitPath™ Assay were compared to broth microdilutions (BMD) performed according to the CLSI method M07-Ed13E 2018.

Data Analysis and Threshold Generation: Using the image captured by the CCD camera, detected cells were estimated by an algorithm that looked at both number of objects in the field of view and the intensity of the objects. Number of cells based on this detection algorithm were generated at time zero, and at time four hours without antibiotic and with all 6 concentrations of each antibiotic. For each urine sample/drug concentration, fold growth was calculated as the signal in the well containing antibiotic after growth (time four) to the signal in the urine sample prior to growth (time zero). Using fold growth and the observation of growth in the corresponding well in the CLSI-compliant broth microdilution, a logistic regression model was used to generate thresholds for determining the fold growth cutoff above which cells are growing in the presence of the antibiotic (and thus, resistant at that concentration) and below which, cells are in the process of dying (and thus, sensitive at that concentration). The point where the fold growth number falls below the determined threshold is the MIC value generated by the assay. Results were correspondingly assigned to categories of susceptible, intermediate, or resistant to each antibiotic. All data was then compared to CLSI standard BMD. Four-hour growth in the absence of antibiotic is a control condition to ensure viable bacterial are present in the processed urine sample.

Figure 55:
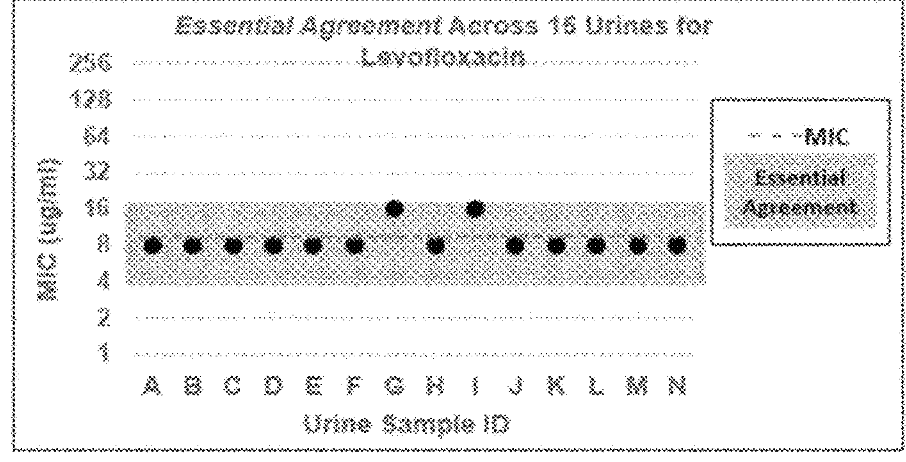
FIG. 55 shows essential agreement across 15 urines.

Results. FIG. 55 to FIG. 57 show there is little to no matrix effect on AST results. FIG. 55 shows the MIC of *E. coli* BAA-2469 determined via the novel AST method (black circles) as compared to the MIC determined by the gold-standard CLSI BMD method without urine present (dashed line) for Levofloxacin. The shaded area is the essential agreement area, which is generally considered to be within acceptable error for the CLSI-compliant BMD process. Most of the MICs for Levofloxacin determined for *E. coli* BAA-2469 using the novel AST method matched the CLSI method exactly and the remaining two fall within the 2-fold essential agreement zone. FIG. 56 summarizes the results obtained for all 5 antibiotics. 100% essential and 100% categorical agreement to standard BMD was observed across 15 culture negative clinical urine samples using the novel AST method. FIG. 57 shows the MIC determined for the 15 culture negative clinical urine samples spiked with *E. coli* using the novel AST method in comparison to the MIC observed in the CLSI-compliant BMD process across the 5 antibiotics tested.

FIG. 56 shows 100% Essential agreement for Levofloxacin with each of the 15 spiked culture negative clinical UTI urine samples to standard BMD.

Conclusion. The inventive method accurately determined the MIC (within the essential agreement zone relative to the gold standard BMD method) for a UTI pathogen (*E. coli*) for all 5 antibiotics tested in all 15 distinct urine matrices. Thus, this novel 4-hour antimicrobial susceptibility test has the capability to provide accurate results directly from urine specimens without the requirement of lengthy growth-based colony purification, saving substantial time. Rapid AST results can improve patient care by allowing the correct, effective antibiotic treatment to be initiated quickly and avoid adding to the spread of antibiotic resistance.

Variations. This example is illustrative of the performance of this novel AST method and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations) and concentration of urine. This methodology can also clearly be applied to other bacterial and non-bacterial pathogens and to minimally processed clinical matrices other than urine.

Example 13. Rapid and Accurate AST for Multiple Targets in Polymicrobial

Overview. Polymicrobial infections are common in many types of infections including wounds. For such infections, which can be life-threatening it is critical to determine which antimicrobial agents can be effective for each infectious pathogen. Current antimicrobial susceptibility testing methods require 2-5 days to purify large numbers of each infectious pathogen in a polymicrobial infection before they can be analyzed.

This example demonstrates the potential for the inventive systems and methods to generate rapid AST in results in just 4.5 hours directly from a patient specimen without the need for lengthy colony purification. The method achieves accurate AST results (MIC values) for each target species in contrived 2-target polymicrobial mixtures compared to the broth microdilution reference standard result.

Experimental Procedure

Preparation of Antibiotic Plates: Microtiter plates containing 6 Ciprofloxacin concentrations 2-fold serial dilution series were prepared. The 2-fold dilution series was prepared at a 10-fold higher concentration the desired concentration in the final broth microdilution, such that addition cells/urine/media mixture would yield the correct antibiotic range. 10 uL of each antibiotic dilution was then aliquoted into the appropriate wells of a 96 well plate. Antibiotic dilutions were verified to be within the appropriate tolerance by confirming that the MIC for at least two CLSI QC strains fell within the QC range reported in CLSI document M100Ed29E-2019. In addition to the wells containing the antimicrobial dilution series, enough wells containing water or other diluent were included for a no antibiotic positive growth control. Antibiotic plates were frozen at −80° C. and thawed completely before use.

Preparation of Cultures: Both a susceptible and resistant strain were chosen for four different organisms (*E. coli* ATCC 25922, *E. coli* BAA-2469, *K. pneumoniae* CDC 0076, *K. pneumoniae* CDC 0043, *P. aeruginosa* CDC 0233, *P. aeruginosa* CDC 0236, *E. faecalis* ATCC 29212, and *E. faecium* ATCC 19434). The strains and their resistances to each antibiotic tested are shown in Table A. Each strain was grown separately with three to five colonies inoculated into 5 mL of Tryptic Soy Broth (TSB) and incubated while shaking for 1-2 hours at 35° C. The Optical Density was measured by a spectrometer and the organisms were diluted to $1\times10^7$ CFU/mL in 1× Cation-adjusted Mueller-Hinton Broth (MHB II) (Teknova, cat. #M5860).

Preparation of Magnetic Particles: A solution of Poly-aspartic acid-conjugated magnetic particles (Fluidmag-PAA, Chemicell, cat. 4108) were diluted 1:20 into 50 mM EPPS buffer, pH 8.2 to $2.75\times10^{12}$ particles/mL. Fluorescent magnetic microspheres containing a green dye (Dragon Green Fluorescent Microspheres, BANGS Laboratories, cat MEDG001) were added to the suspension at a final concentration of $3\times10^6$ particles/mL. These particles enable the optical system to focus on the correct plane. The magnetic particle mixture was sonicated for 1 minute immediately prior to use to minimize aggregation. Separate magnetic particle suspensions were prepared for the time zero and time four-hour assays described below). An identical procedure was done with the 2 hydroxypropyl trimethylammonium chloride-coated silica magnetic particles (SiMag-Q, Chemicell, cat. 1206-5).

Bacterial Cell Labeling at AST time zero: Assay signal prior to the initiation of bacterial growth in the presence or absence of antibiotics (time zero or T0) was determined for each species and strain. 5 μL of target A was combined with either 5 μL target B or 5 μL of MHB II for a final concentration of $5\times10^6$ CFU/mL per organism was added to 80 μL of hybridization buffer (final concentration: 3×SSC (0.45 M NaCl, 0.045 M sodium citrate pH 7) (Sigma, cat. #S6639), 0.25M Guanidine Thiocyanate (Sigma, cat. #503-84-0), 5% PEG MW 3350 (Sigma, cat. #P-3640), 7.5% Igepal CA-630 (Sigma, cat. #13021), 0.2% cetrimide (Sigma, cat. #H9151), 1× Cation-adjusted Mueller-Hinton Broth (MHBII), species-specific DNA oligonucleotide FISH probes and unlabeled DNA helper probe (sequences and concentrations found in Table B)). A final concentration of 10% urine was obtained by adding 10 μL of pooled urine (Innovative Research, cat. IR100007P-24203) directly to the mixture for a 100 μL total reaction. 10 μL of the either the SiMag-Q magnetic particle mixture (for conditions where *E. coli, K. pneumoniae* and *P. aeruginosa* strains were being labeled) or the Fluidmag-PAA magnetic particle mixture (for conditions where *Enterococcus* spp. were labeled), prepared as described above, was added directly to this mixture. 100 μL of the sample, now containing the hybridization mixture, urine, and magnetic particles, was transferred to a microtiter plate containing 50 μL of dye-cushion (50 mM TRIS pH 7.5 (Teknova, cat. T5075), 7.5% v/v Optiprep (Sigma, cat. D1556), 5 mg/mL Direct Black-19 (Orient, cat. #3222), dried down at 60° C.) (dry-cushion plate) and incubated at 35° C. for 30 minutes. After this incubation, the microtiter plates were placed onto a strong permanent magnet (Dexter magnetic technologies, cat. 54170260) for 4 minutes to bring the labeled and magnetic-particle-interacting bacterial cells into close proximity to the imaging surface.

Imaging of labeled cells: The MultiPath™ laboratory imaging system is a custom-built instrument and software that is capable of automatically capturing image data from selected wells of a microtiter plate. It uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1 MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Four-Hour Growth: A polymicrobial sample, containing two species, was tested for susceptibility against 1 antimicrobial agent: Ciprofloxacin. Antibiotic plates containing these antimicrobial agents were prepared according to the method described above. At the same time as the time zero cell quantification was occurring, 5 μL of either the species to be labeled and detected and 5 μL of either a bacterial species the might be present in a polymicrobial UTI infection (but will not label) or MHB II as control, 10 μL of pooled urine, and 70 μL of MHB II were added to each well of the antibiotic plate. The samples were allowed to grow in a standing air incubator at 35° C. for 4 hours. Each strain in this example served in once instance as the labeled target species, and in another instance as the unlabeled member of the polymicrobial pair.

Bacterial Cell Labeling at AST time four-hour growth: After samples had incubated in the presence and absence of antibiotics for four hours (T4), cells were labeled and quantified to determine how much growth, if any, occurred. 10 μL of the incubated sample-antibiotic plate (10%) was transferred to a microtiter plate and combine with 100 μL hybridization buffer, FISH probes, helper probes, magnetic particles, and focus particles in the same manner as described above for assay time zero.

Comparison Method: Results using the novel AST method described here were compared to broth microdilutions (BMD) performed according to CLSI M07-Ed13E 2018.

Data Analysis and Threshold Generation: Using the image captured by the CCD camera, detected cells were estimated by an algorithm that looked at both number of objects in the field of view and the intensity of the objects. The number of cells based on this detection algorithm were generated at time zero, and at time four hours without antibiotic and with all 6 concentrations of Ciprofloxacin. For each sample inoculum/drug concentration, fold growth was calculated as the signal in the well containing antibiotic after growth (time four) to the signal in the urine sample prior to growth (time zero). Using fold growth and the observation of growth in the corresponding well in the CLSI-compliant broth microdilution, a logistic regression model was used to generate thresholds for determining the fold growth cutoff above which cells are growing in the presence of the antibiotic (and thus, resistant at that concentration) and below which, cells are in the process of dying (and thus, sensitive at that concentration). The point where the fold growth number falls below the determined threshold is the MIC value generated by the assay. MIC results were correspondingly assigned to categories of susceptible, intermediate, or resistant based on the CLSI M100Ed28 2018 guidelines. All data was then compared to CLSI standard BMD.

Results. FIG. 59, FIG. 60, and FIG. 61 summarize the results of all 48 different pairwise combinations with the antibiotic Ciprofloxacin. FIG. 59 shows all MICs determined for the target bacteria by the novel 4.5 hour AST method—regardless of the presence of a second susceptible or resistant bacteria—were within the 2-fold tolerance range accepted for the gold-standard BMD method (termed essential agreement) for each target bacteria (determined in the absence of a second bacteria). FIG. 62 and FIG. 63 show that the sensitive and resistance categorical determinations for each target bacteria by the new AST method were also not impacted by these pair-wise combinations and were 100% consistent with the BMD determinations.

Conclusions. The inventive AST method can accurately determine antibiotic susceptibility for each species in a polymicrobial sample in 4.5 hours without requiring the time consuming colony purification needed by current methods. The results show the potential for the invention to determine the antimicrobial agents that can effectively treat life-threatening polymicrobial infections in just hours rather than the days required by today's methods.

Variations. This example is illustrative of the performance of this novel AST method and is not limited to the specific details included in the description. One skilled in the art will readily understand that many variations are therefore possible, including using different probe sequences and nucleic acid structures (PNA, LNA, etc.) and alternative assay chemistries (different detergents, chaotropes, fluorophores, buffers, pH, temperatures, reaction times, component concentrations). This methodology can also clearly be extended to other biological specimens, to other bacteria and to other antibiotics.

Example 14. Rapid and Accurate Detection of Multiple Target Pathogens in a Single Specimen in a Cartridge on an Automated Instrument Overview. Polymicrobial infections, that is infections caused by more than one bacterial species, are common. Current, culture-based and MALDI-TOF based methods for identifying pathogens, require lengthy colony purification steps for separately purifying large number of cells each target species. This example demonstrates the use of the inventive FISH method to detect and identify multiple species of target pathogens present in contrived urine samples in 30 minutes on an automated analyzer inside a single-use consumable cartridge containing all assay reagents. The example shows the potential of the systems and methods of the invention to rapidly and specifically identify multiple target pathogens in polymicrobial infections.

Experimental Procedure

Urine specimens: Ten culture negative clinical urine samples (remnant) were purchased from Discovery Life Sciences. Samples were received >7 days post collection and stored at −80° C. until use. For each sample, color of urine, pH, and presence of particulates were noted. Upon receipt, conventional urine culture was performed on the urines to determine samples were culture negative. Briefly, a calibrated 1 uL loop was placed into a well-mixed urine sample and evenly spread over a Tryptic soy agar (TSA, BD cat. 221185) plate and incubated in a 35° C. air incubator for 18-24 hours. The remainder of the urine samples were processed and assayed as described below.

Urine processing: Prior to performing identification (ID), urine preservative and other potentially interfering compounds were removed using size exclusion chromatography. 2.5 mL of each clinically negative urine sample was applied to a pre-washed Zeba™ Spin Desalting column, 7K MWCO (ThermoFisher, cat. #89893). The sample was passed through the column via centrifugation as described by the manufacturer.

Preparation of Dehydrated Reagents in Cartridge: Prior to performing identification (ID), 45 μL of 2.2× concentrated hybridization buffer (6.7×SSC (1 M NaCl, 0.1 M sodium citrate, (Sigma, cat. #S6639), 0.4% w/v cetrimide (Sigma, cat. #H9151), 1.71% w/v CHAPSO (Sigma cat. #C3649), 1.6% SB3-12 w/v (Sigma cat. #D0431), and 0.29M guanidine thiocyanate (Sigma, cat. #G9277)) was distributed into 6 of the reagent wells of the cartridge. Once rehydrated in the final 100 uL volume after processing by the analyzer, the normal 1× hybridization buffer (3×SSC (0.45 M NaCl, 0.045 M Na citrate), 0.18% cetrimide, 0.77% CHAPSO, 0.72% SB3-12, and 0.13M guanidine thiocyanate) will be achieved. 1.8 μL of each target species-specific DNA oligonucleotide FISH probe and unlabeled DNA helper probe mixture was added to 2 out of 8 of the reagent wells (N=2 for each target in 1 cartridge). *E. coli* FISH oligonucleotide probe sets were added to reagents wells corresponding to cartridge location A1 and A2, *K. pneumoniae* probe sets were added to reagents wells corresponding to cartridge location A3 and A4 and *P. aeruginosa* probe sets were added to reagents wells corresponding to cartridge location A5 and A6. These cartridge wells containing hybridization buffer and specific probes were then incubated in a 50° C. convection oven for 16-20 hours to dehydrate the materials.

Preparation of Magnetic Particles: Poly-aspartic acid-conjugated magnetic particles (Fluidmag-PAA, Chemicell, cat. 4108) were diluted 1:20 into 50 mM Epps buffer, pH 8.2 to a concentration of $2.75\times10^{12}$ particles/mL with a final concentration of 10% w/v Trehalose (Sigma, cat. #T9449). To this dilution, fluorescent magnetic microspheres containing a green dye (Dragon Green Fluorescent Microspheres, BANGS Laboratories, cat. MEDG001) were added to the suspension at a final concentration of $3\times10^{6}$ particles/mL. The magnetic particle mixture was sonicated for 1 minute prior to immediately use to minimize aggregation. The mixture was then lyophilized in 10 μL volume beads ($2.64\times10^{12}$ PAA particles per reaction) and 1 bead was placed in each of the 6 reagent wells.

Preparation of Cultures: Log cultures of three different target pathogens (*E. coli* ATCC 25922, *K. pneumoniae* ATCC 13883, and *P. aeruginosa* ATCC 27853) were grown separately with three to five colonies inoculated into 5 mL of Tryptic Soy Broth (TSB, Hardy Diagnostics cat. U65) and incubated while shaking for 1-2 hours at 35° C. The Optical Density was measured by a spectrometer and the organisms were diluted to about $5\times10^{6}$ CFU/mL in 1× Cation-adjusted Mueller-Hinton Broth (MHBII, Teknova cat. M5860).

Bacterial Cell Labeling and imaging for Identification: Assay signal was determined for each target pathogen in contrived polymicrobial mixture containing two bacteria of interest (3 total 2-bacteria combinations) in a final concentration of 30% processed urine. Each polymicrobial bacterial combination was tested in 10 unique different culture negative clinical samples (30 urines tested in total). 103.5 μL of bacterial target A (~$5\times10^{5}$ CFU/mL per reaction) 103.5 μL of bacterial target B (~$5\times10^5$ CFU/mL per reaction), 360 μL urine, and 633 μL were combined for a total volume of 1.2 mL; 1 mL of that mixture was transferred to the cartridge sample addition port. The cartridge was then placed on the instrument and all subsequent actions were automatically performed. The sample was first directed under vacuum into the 6 growth wells at the top of the cartridge. Sample was then immediately moved to reaction wells, rehydrating the hybridization buffer/FISH probe mix and lyophilized magnetic particles. Sample then continued to the optical windows containing 45 μL of dehydrated "dye cushion" (50 mM TRIS pH 7.5 (Teknova, cat. T5075), 7.5% v/v Optiprep (Sigma, cat. D1556), 5 mg/mL Direct Black-19 (Orient, cat. #3222), dried for 60° C. for 3 hours in a convection oven) and incubated at 35° C. for 30 minutes on the analyzer. After this incubation, the cartridges were relocated to the magnet station, and placed atop a strong permanent magnet (Dexter magnetic technologies, cat. 54170260) for 4 minutes to bring the labeled and magnetic-particle-interacting bacterial cells into proximity to the imaging surface at the bottom of the wells. Finally, the cartridge was moved to the imaging station and imaging taken using non-magnified CCD imager as described below. In brief, focusing on each individual well was performed by taking successive images of the fluorescent magnetic microspheres in the green channel, the plane of focus determined, and a corresponding image at that location taken in the red color channel to image labeled bacterial cells.

Imaging of labeled cells: The MultiPath™ Analyzer imaging system is a custom-built instrument and software that is capable of automatically capturing image data from selected wells of a MultiPath Cartridge as part of a fully automated test. It uses a custom designed precision 3 axis positioning system to locate each well over a fluorescence-based image acquisition subsystem. The Analyzer can image in 4 separate color channels and uses an objective lens, illumination LEDs, fluorescent filter sets, and camera. The objective lens has a field of view designed to capture the image of an entire Cartridge Imaging Well. The illumination module light source consists of 2 high power LEDs per color channel. A series of fluorescent image frames are captured with a camera using a 3.1 MP Sony IMX265 monochrome sensor with 12-bit per pixel quantization. The final image for each well is then formed by summing multiple frames. 16 frames were captured at a 100 msec exposure using 635/25 nm excitation and 667/30 nm emission filters. The focus particles are imaged at 470/40 nm excitation and 520/40 nm excitation filters and captured 2 frames at a 20 msec exposure.

Data Analysis: Using the image captured by the CCD camera, detected cells were estimated by an algorithm that looked at both number of objects in the field of view and the intensity of the objects. Signal in a channel was considered detected if assay signal was above 130.

Figure 64:
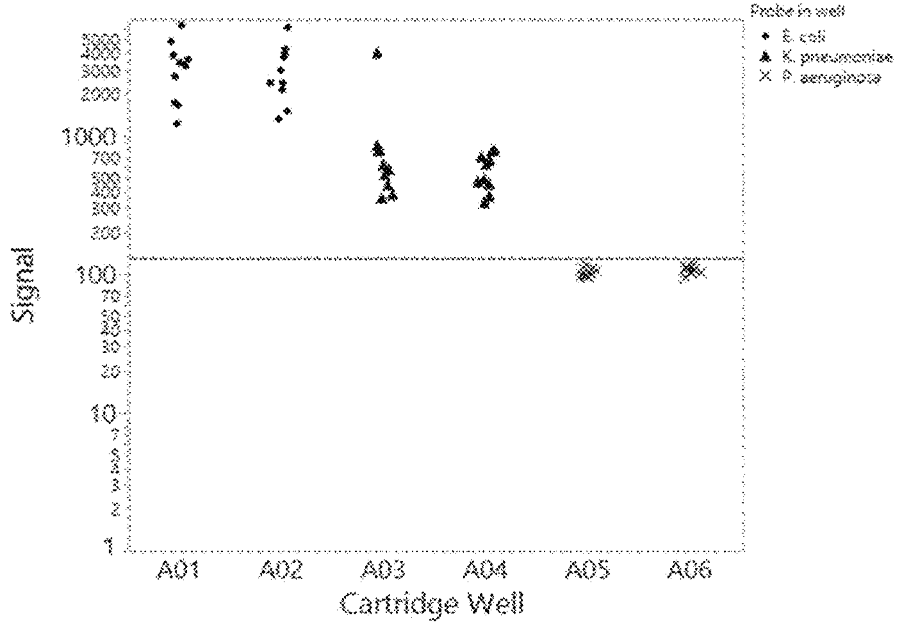
FIG. 64 shows target pathogens are detected only in the wells containing their species-specific DNA oligonucleotide FISH probes.
Figure 65:
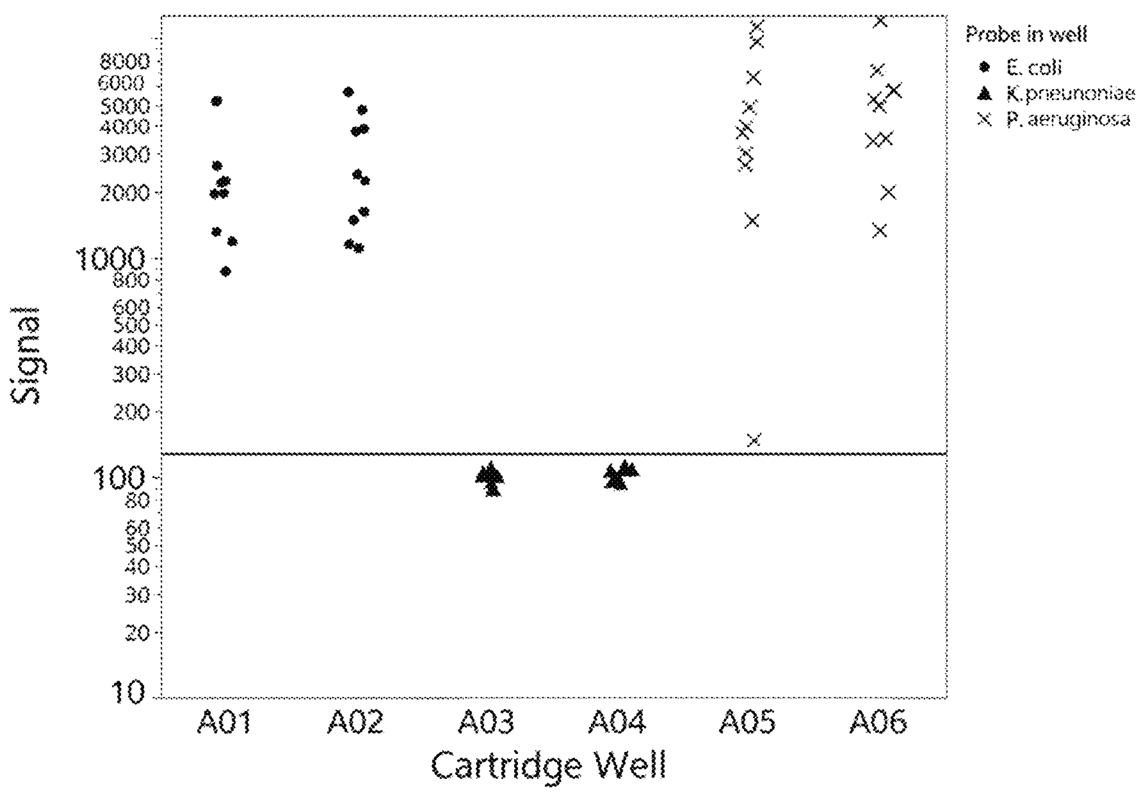
FIG. 65 shows target pathogens are detected only in the wells containing their species-specific DNA oligonucleotide FISH probes.
Figure 66:
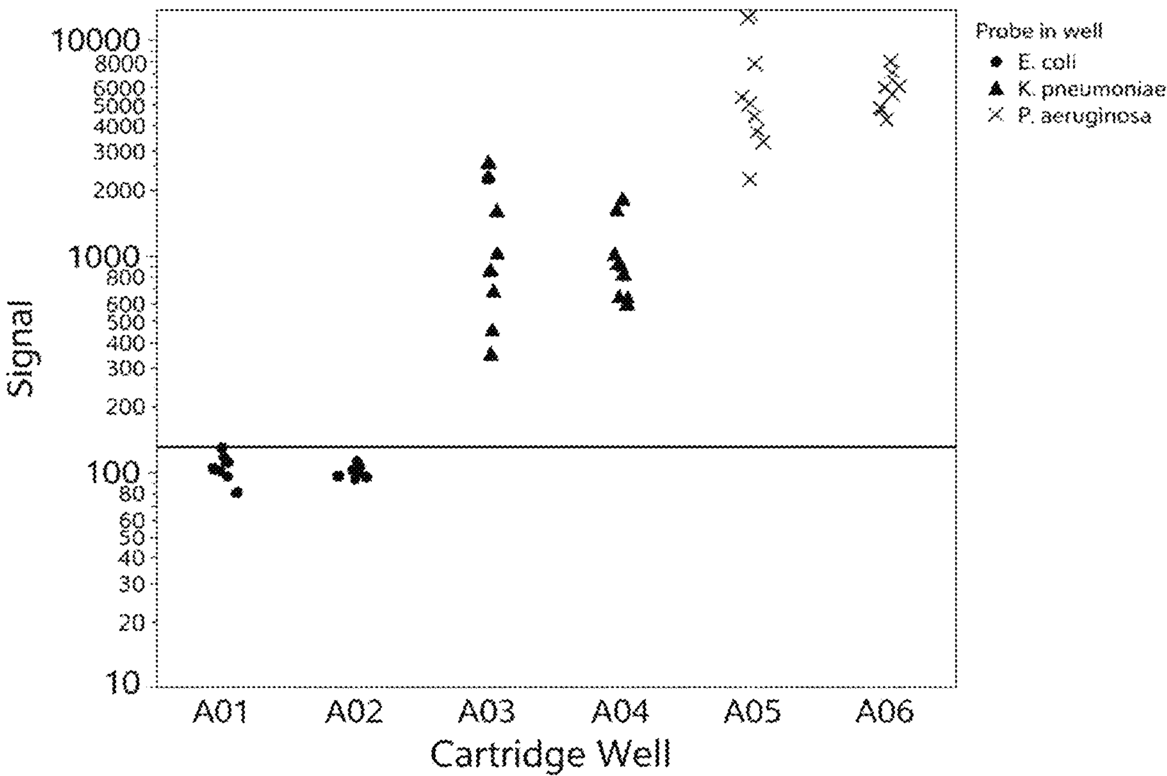
FIG. 66 shows target pathogens are detected only in the wells containing their species-specific DNA oligonucleotide FISH probes.

Results. The data demonstrate successful identification of 2 target pathogens in a single sample with no detection of the pathogen that is absent (i.e. no cross reactivity of the FISH probes to the non-target bacteria). FIG. 64 shows the cartridges run where the *E. coli/K. pneumoniae*-mixed samples were tested (N=10). FIG. 65 shows the cartridges run where the *E. coli/P. aeruginosa*-mixed samples were tested (N=10). FIG. 66 shows the cartridges where the *K. pneumoniae/P. aeruginosa*-mixed samples were tested (N=10). *K. pneumoniae/P. aeruginosa* cartridge #6 was removed from the analysis due to failure of that cartridge to produce a valid result. In addition, an artifact was observed in A3 of *E. coli/P. aeruginosa* cartridge #9, which caused the signal in the well to appear abnormally high, so this single replicate was eliminated. The replicate of this excluded point (well A4) did not have this artifact, so *K. pneumoniae* was still categorized as not detected. Although assay signal varied across the different cartridges, in all cases other than those already described, the two bacteria added to the culture negative urine was detected while very low signal is observed in the wells containing the probe for the bacteria that was not added.

Conclusions. This example demonstrates the inventive isothermal FISH method performed on an automated analyzer with stabilized reagents inside a consumable cartridge can specifically identify multiple target bacterial species in a contrived urine sample. This shows the potential of the method to identify multiple pathogens in polymicrobial infections. The example also demonstrates the specificity of the method, as no cross-species detection was observed.

Variations. This example is illustrative of the performance of this novel FISH method on a cartridge and is not limited to the specific details included in the description. One skilled in the art will readily understand that many variations are therefore possible, including using different probe sequences and nucleic acid structures (PNA, LNA, etc.), alternative assay chemistries (different detergents, chaotropes, fluorophores, buffers, pH, temperatures, reaction times, component concentrations), concentration of urine and urine processing procedures and alterations to reactant stabilization (lyophilization of components). This methodology can also clearly be extended to other biological specimens and to other bacterial and non-bacterial pathogens.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for antimicrobial susceptibility testing, the method comprising:

obtaining a polymicrobial specimen;

dividing the specimen into division wells wherein at least some of the division wells comprise different antimicrobial agents or concentrations of one or more agents;

incubating the specimen in the wells to allow differential growth in response to the different antimicrobial agents or concentrations of antimicrobial agents;

labeling specific target cells in the specimen with photonically fluorescently labeled nucleic acid probes wherein said fluorescently labeled nucleic acid probes bind to target specific sequences on ribosomal RNA;

incubating said labeled target cells with magnetic particles thus forming complexes of fluorescently labeled target cells bound to magnetic particles, wherein said photonic fluorescent labeling of said target cells and said incubating of said target cells with magnetic particles occur in a concerted reaction;

depositing said complexes on a detection surface of each imaging well using magnetic force; and counting individual target cells of the complexes in each imaging well using digital imaging to identify the antimicrobial agent or concentration of an antimicrobial agent that inhibits growth of the target cells.

2. The method of claim 1, in which one of said division wells is a no antibiotic control division well, wherein the no antibiotic control division well contains specimen, growth medium, and no antimicrobial agent.

3. The method of claim 2, further comprising comparing a number of cells obtained from the no-antibiotic control division well to the number of cells obtained from the division wells containing specimen, growth medium and said antimicrobial agents to identify the antimicrobial agent or concentration of antimicrobial agent that inhibits growth of the target cells.

4. The method of claim 1, wherein the incubating step includes fluorescently labeling the microbes in a target cell specific manner, and the counting step includes imaging each well and counting fluorescent spots in an image.

5. The method of claim 1, wherein the method does not comprise nucleic acid amplification.

6. The method of claim 1, wherein the labeling step lasts less than an hour and is performed at a temperature lower than 40 degrees C. in a growth medium.

7. The method of claim 1, wherein the dividing, incubating, and counting steps are performed within a single cartridge.

8. The method of claim 7, further comprising:

loading the cartridge into an analyzer, wherein the analyzer uses a one or more magnet to separate the target cell from other parts of the specimen and uses an imaging subsystem to perform the counting step.

9. The method of claim 8, wherein the analyzer uses a pneumatic subsystem to perform the dividing step within the cartridge, wherein the division wells are within the cartridge and are preloaded with the different agents or concentrations of antimicrobial agents, wherein, after the dividing and the incubating steps, the analyzer transfers contents of the division wells to corresponding reagent wells to therein expose the incubated specimen to the target cell binding magnetic beads and to target cell specific detectable labels.

10. The method of claim 8, wherein the analyzer uses a magnet to pull complexes of photonically labeled target cells bound to magnetic particles through a dye cushion so that they are deposited on the detection surfaces of each imaging well within the cartridge, wherein said dye cushion attenuates the imaging background arising from photonically labeled probe molecules not bound to said deposited complexes.

11. The method of claim 10, wherein the magnet pulls the microbe binding magnetic beads through a dye cushion that excludes unbound detectable labels from the detection surface.

12. The method of claim 8, wherein the analyzer uses a carousel and/or a mechanical cartridge conveyance to transfer the cartridge to an imaging subsystem to perform the counting step.

13. The method of claim 1, wherein the incubating and counting steps accomplish fluorescent in situ hybridization (FISH) analysis substantially at physiological temperature within the analyzer.

14. The method of claim 1, wherein identifying the antimicrobial agent that inhibits growth of the microbe comprises comparing the number of complexes in the incubated specimen to the number of complexes in an unincubated specimen.

15. The method of claim 8, wherein the analyzer uses the cartridge to perform target cell specific counting of the individual microbes after the differential growth.

16. The method of claim 8, wherein the analyzer manipulates the cartridge to perform the dividing, incubating, and counting steps.

17. The method of claim 1, wherein the specimen does not require any chemical or molecular sample preparation techniques by a user before dividing the specimen into division wells.

18. The method of claim 1, wherein the specimen is selected from the group consisting of: whole blood, plasma, serum, urine, sputum, stool, wound, peritoneal fluid, pus, lymph, vaginal secretions, nasal secretions, and tissue specimens.

* * * * *